United States Patent
Seo et al.

(10) Patent No.: US 9,168,111 B2
(45) Date of Patent: Oct. 27, 2015

(54) ABUTMENT DEVICES AND METHODS FOR NATURAL TEETH

(75) Inventors: Young Seo, Sunnyvale, CA (US); Jianhua Yang, Saratoga, CA (US); Victor Chechelski, Mountain View, CA (US); Jong Gil Park, Sunnyvale, CA (US)

(73) Assignee: Rodo Medical, Inc., San Jose, CA (US)

( * ) Notice: Subject to any disclaimer, the term of this patent is extended or adjusted under 35 U.S.C. 154(b) by 397 days.

(21) Appl. No.: 13/021,616

(22) Filed: Feb. 4, 2011

(65) Prior Publication Data

US 2012/0202173 A1  Aug. 9, 2012

(51) Int. Cl.
| | | |
|---|---|---|
| *A61C 13/12* | (2006.01) | |
| *A61C 8/00* | (2006.01) | |
| *A61C 5/08* | (2006.01) | |
| *A61C 13/265* | (2006.01) | |

(Continued)

(52) U.S. Cl.
CPC .............. *A61C 8/0065* (2013.01); *A61C 5/08* (2013.01); *A61C 8/005* (2013.01); *A61C 8/0025* (2013.01); *A61C 8/0048* (2013.01); *A61C 8/0053* (2013.01); *A61C 8/0056* (2013.01); *A61C 8/0059* (2013.01); *A61C 8/0062* (2013.01); *A61C 8/0068* (2013.01); *A61C 8/0081* (2013.01); *A61C 8/0089* (2013.01); *A61C 13/2656* (2013.01); *A61C 13/30* (2013.01); *A61C 19/06* (2013.01); *A61C 3/16* (2013.01); *A61C 2201/007* (2013.01)

(58) Field of Classification Search
CPC ..................... A61C 13/2656; A61C 2201/007; A61C 8/0048–8/0078
USPC .......................... 433/169, 171–174, 218, 219
See application file for complete search history.

(56) References Cited

U.S. PATENT DOCUMENTS

| | | | |
|---|---|---|---|
| 3,328,879 A | * | 7/1967 | Bax ............................... 433/218 |
| 4,144,882 A | | 3/1979 | Takemoto et al. |

(Continued)

FOREIGN PATENT DOCUMENTS

| | | |
|---|---|---|
| JP | 2008-212586 | 9/2008 |
| WO | WO 2008/125852 | 10/2008 |

(Continued)

OTHER PUBLICATIONS

PCT Patent Application No. PCT/US2010/041227 filed Jul. 7, 2010 in the name of Seo, International Search Report and Written Opinion mailed Sep. 23, 2010.

*Primary Examiner* — Cris L Rodriguez
*Assistant Examiner* — Matthew Saunders
(74) *Attorney, Agent, or Firm* — Levine Bagade Han LLP

(57) ABSTRACT

Root canal abutment devices and methods which facilitate the adjustment or removal of an oral appliance, e.g., a crown or bridge, from a reconfigurable abutment assembly are described. The adjustable abutment assembly may be secured within a pulp chamber of a pre-existing tooth. The abutment assembly has a projecting abutment portion with one or more shape memory alloy sleeves or plates or elements extending along the abutment. Each of the sleeves has a length with at least one curved or arcuate portion. Energy may be applied to the elements such that the arcuate portion flattens to allow for the oral appliance to be placed thereupon while removal of the energy allows the elements to reconfigure into its curved configuration thereby locking the oral appliance to the abutment. Removal of the oral appliance may be effected by reapplication of energy to the elements.

8 Claims, 43 Drawing Sheets

(51) Int. Cl.
*A61C 13/30* (2006.01)
*A61C 19/06* (2006.01)
*A61C 3/16* (2006.01)

(56) References Cited

U.S. PATENT DOCUMENTS

| | | | |
|---|---|---|---|
| 4,153,060 A | 5/1979 | Korostoff et al. | |
| 4,681,542 A * | 7/1987 | Baum | 433/172 |
| 4,728,330 A | 3/1988 | Comparetto | |
| 5,061,285 A | 10/1991 | Koch | |
| 5,106,299 A | 4/1992 | Ghalili | |
| 5,232,364 A | 8/1993 | Rosen | |
| 5,470,230 A | 11/1995 | Daftary et al. | |
| 5,507,826 A | 4/1996 | Besselink et al. | |
| 5,516,288 A | 5/1996 | Sichler et al. | |
| 5,697,779 A | 12/1997 | Sachdeva et al. | |
| 5,791,899 A | 8/1998 | Sachdeva et al. | |
| 5,876,434 A | 3/1999 | Flomenblit et al. | |
| 5,951,288 A | 9/1999 | Sawa | |
| 5,979,456 A | 11/1999 | Magovern | |
| 6,710,314 B2 | 3/2004 | Reiss et al. | |
| 8,047,844 B2 | 11/2011 | Seo | |
| 8,109,764 B2 | 2/2012 | Seo | |
| 8,221,118 B2 | 7/2012 | Seo | |
| 8,317,515 B2 | 11/2012 | Seo et al. | |
| 8,403,668 B2 | 3/2013 | Seo | |
| 8,491,303 B2 | 7/2013 | Seo et al. | |
| 8,651,864 B2 | 2/2014 | Seo et al. | |
| 2003/0124480 A1 | 7/2003 | Peacock | |
| 2004/0193261 A1 | 9/2004 | Berreklouw | |
| 2006/0154195 A1 | 7/2006 | Mather et al. | |
| 2006/0246396 A1 | 11/2006 | Suttin et al. | |
| 2007/0191879 A1 | 8/2007 | Gandhi et al. | |
| 2008/0090207 A1 | 4/2008 | Rubbert | |
| 2008/0090209 A1 | 4/2008 | Snaper | |
| 2011/0014585 A1 * | 1/2011 | Seo | 433/173 |
| 2011/0123945 A1 | 5/2011 | Seo | |
| 2011/0151397 A1 | 6/2011 | Seo et al. | |
| 2011/0171599 A1 | 7/2011 | Seo et al. | |
| 2012/0064479 A1 | 3/2012 | Seo | |
| 2012/0211119 A1 * | 8/2012 | Rule et al. | 138/155 |
| 2013/0011812 A1 | 1/2013 | Seo | |
| 2013/0177873 A1 | 7/2013 | Seo et al. | |
| 2013/0224686 A1 | 8/2013 | Seo | |

FOREIGN PATENT DOCUMENTS

| | | |
|---|---|---|
| WO | WO 2008/147097 | 12/2008 |
| WO | WO 2011/008605 | 1/2011 |
| WO | WO 2012/106672 | 8/2012 |
| WO | WO 2012/106676 | 8/2012 |

* cited by examiner

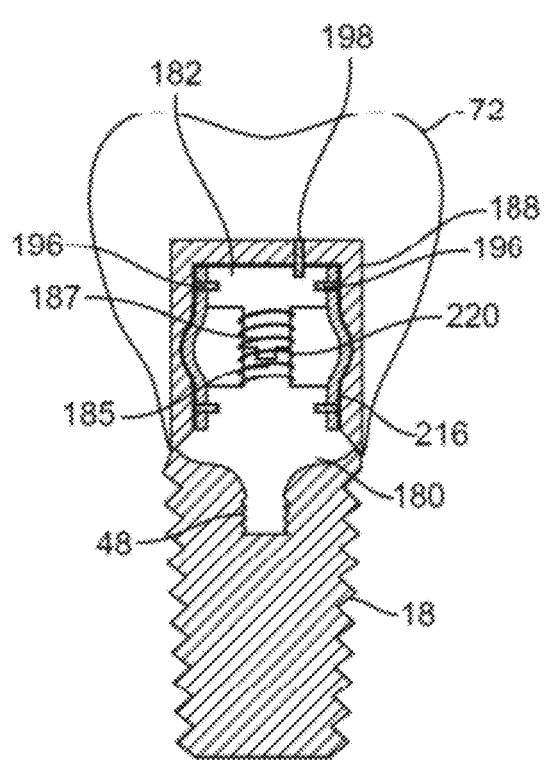
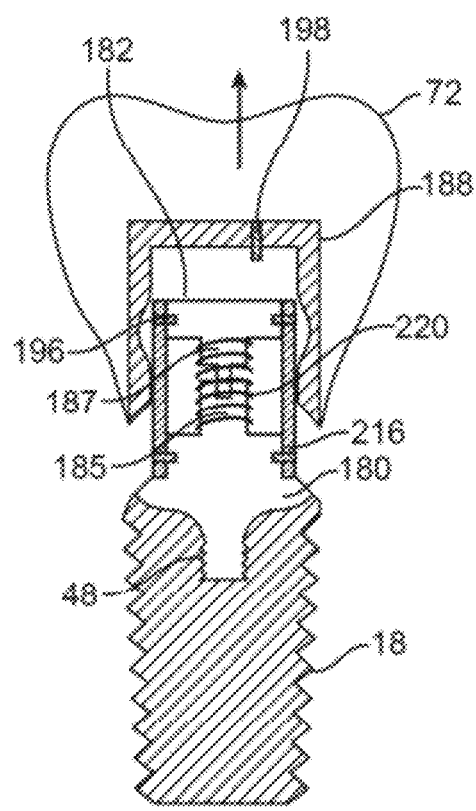
FIG. 18A
FIG. 18B
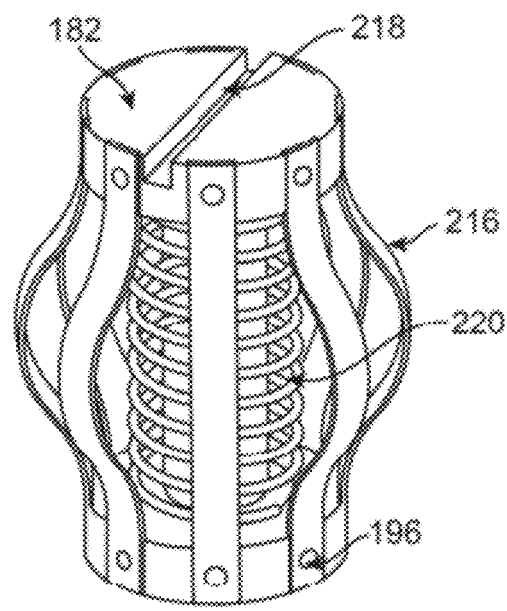
FIG. 18C

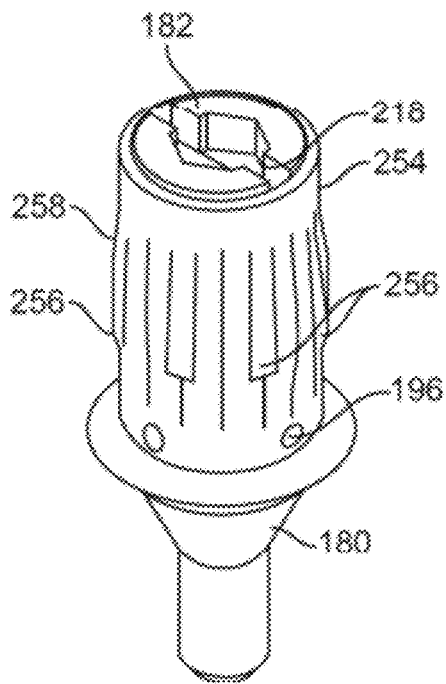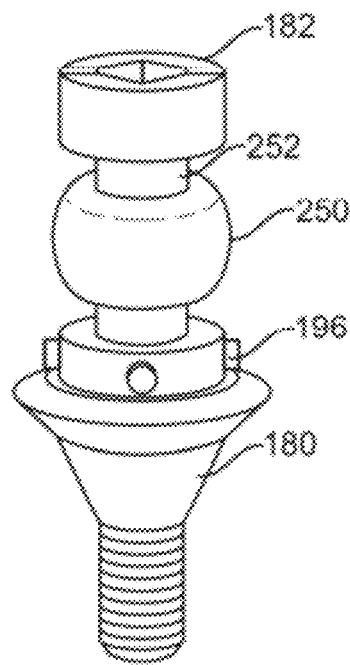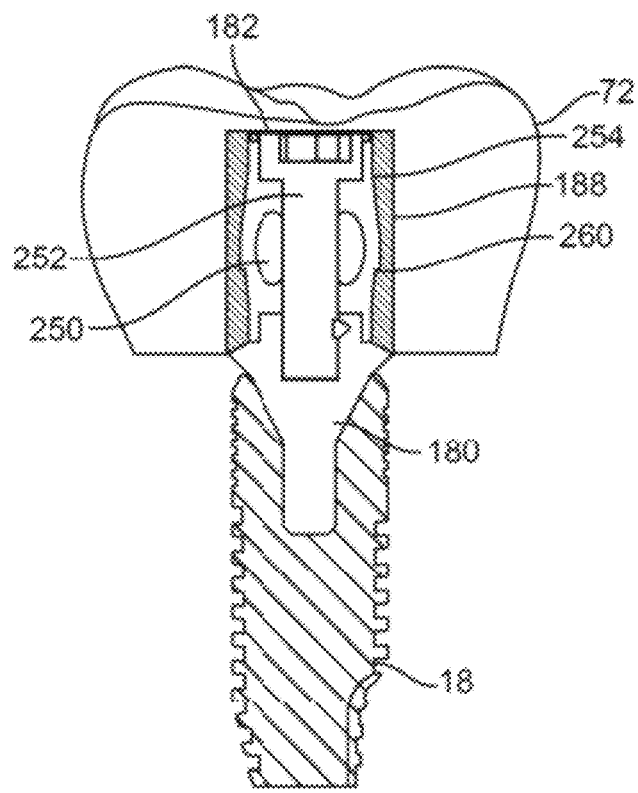
FIG. 22A
FIG. 22B
FIG. 22C

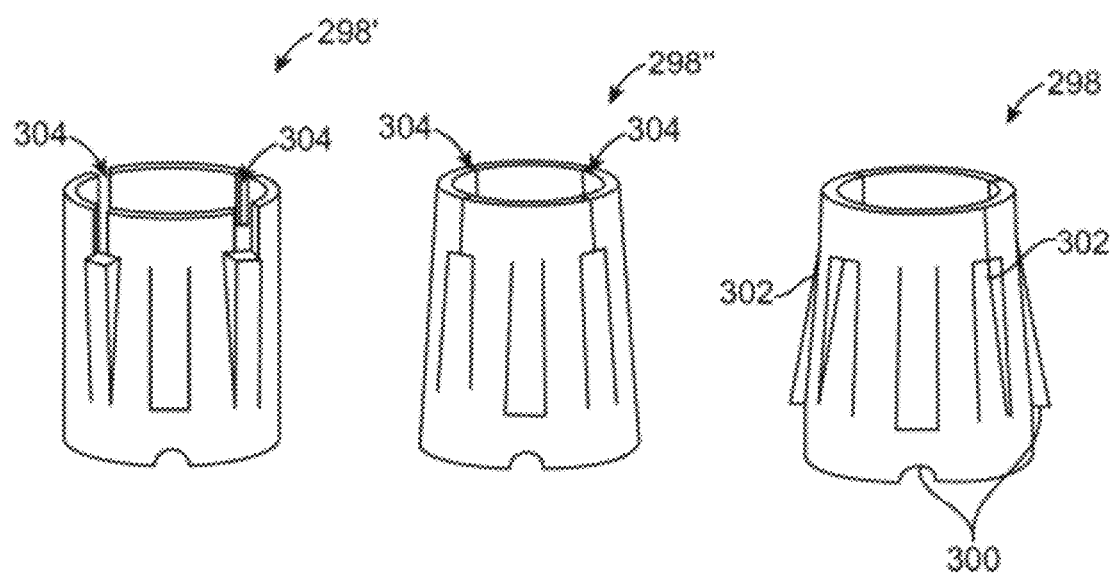
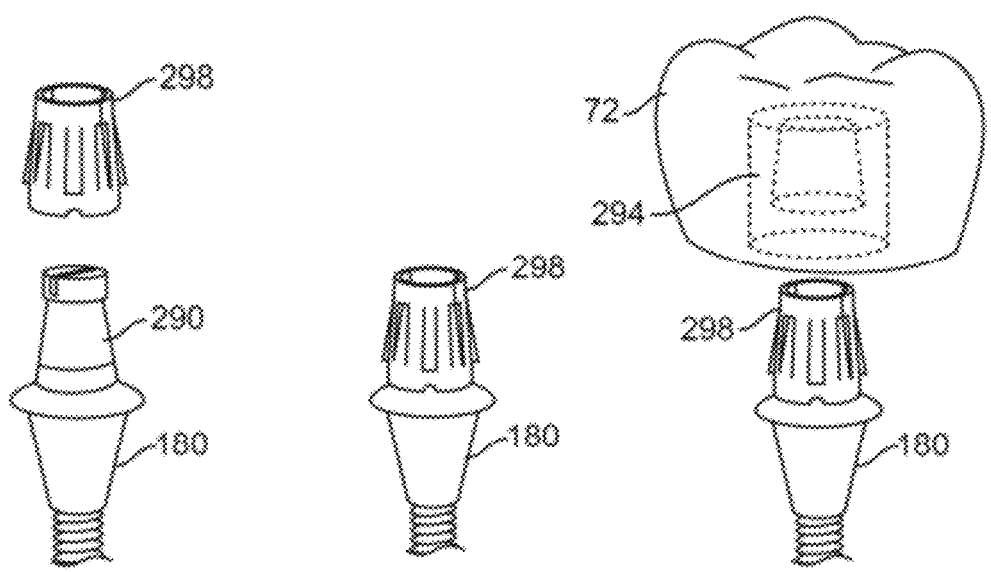
FIG. 27A  FIG. 27B  FIG. 27C

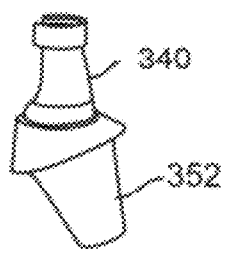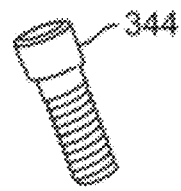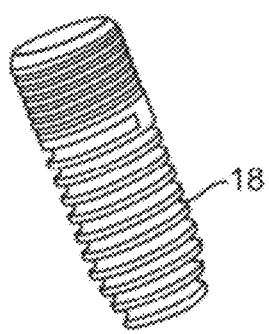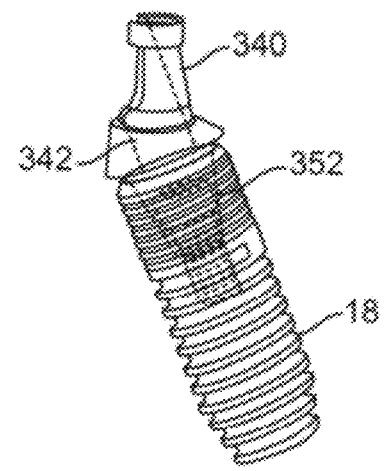
FIG. 32A
FIG. 32B
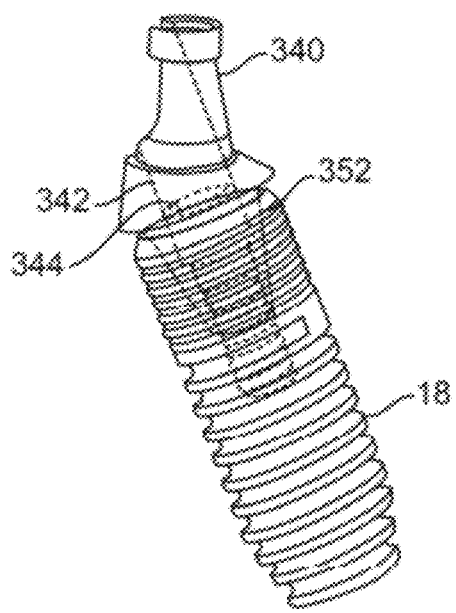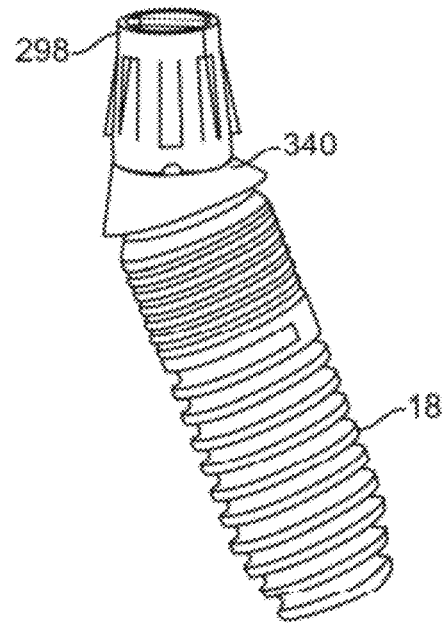
FIG. 32C
FIG. 32D

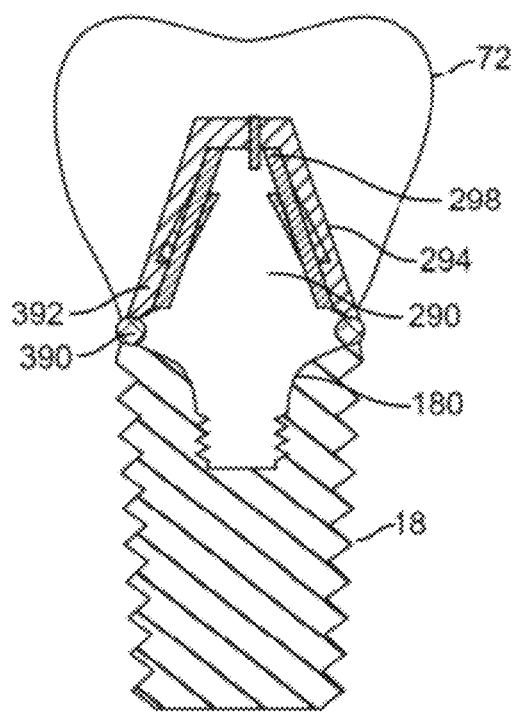
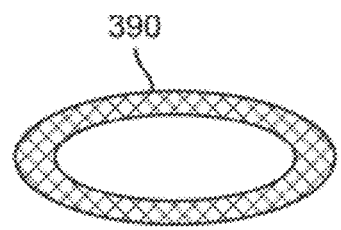
FIG. 36A
FIG. 36B
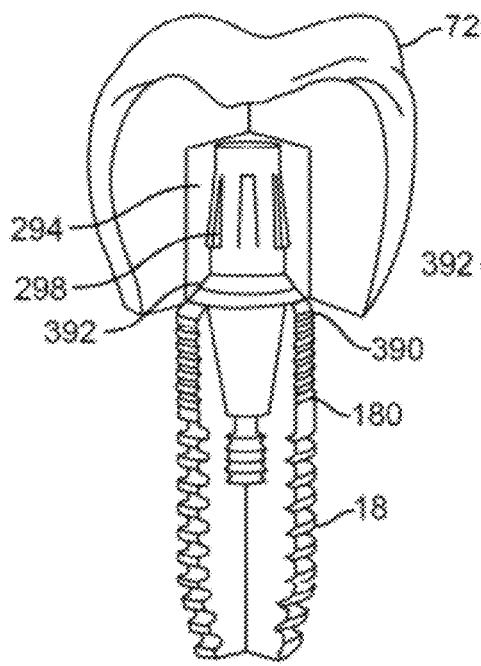
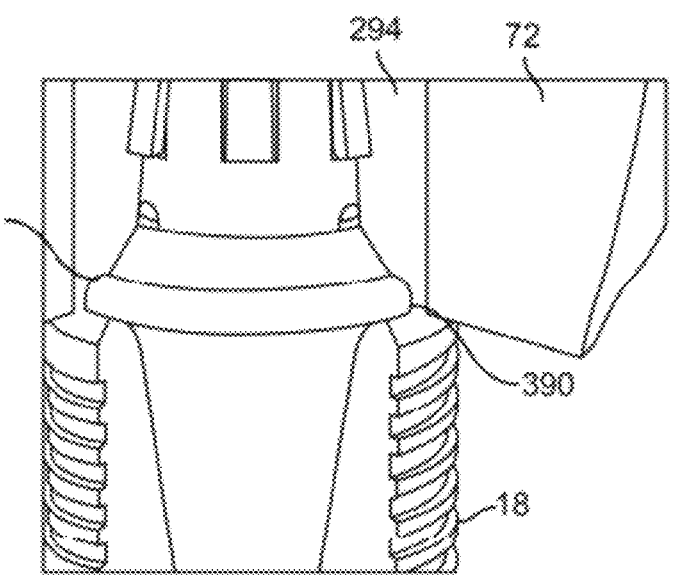
FIG. 36C
FIG. 36D

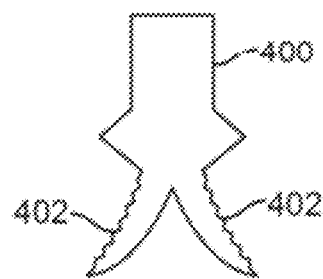
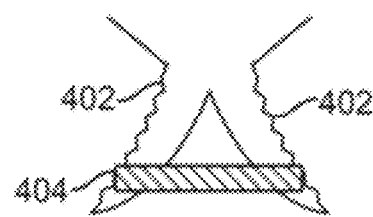
FIG. 37A    FIG. 37B
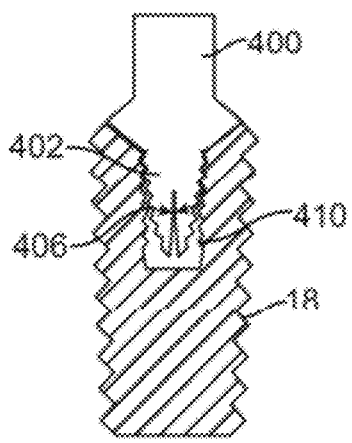
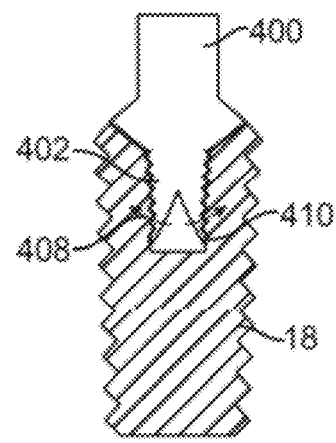
FIG. 38A    FIG. 38B
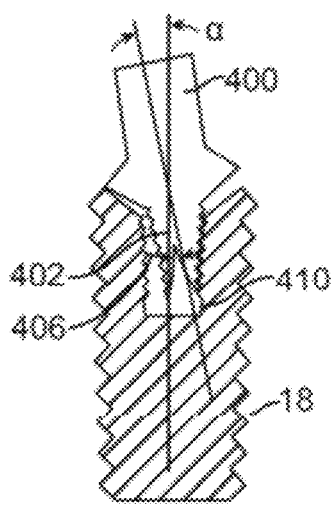
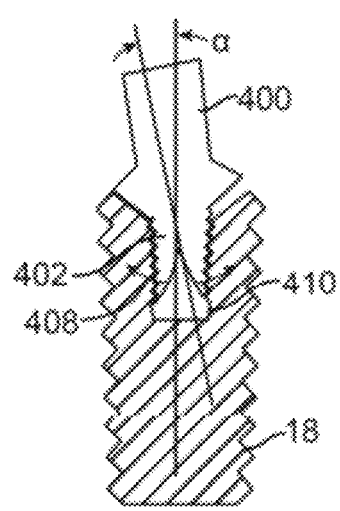
FIG. 39A    FIG. 39B

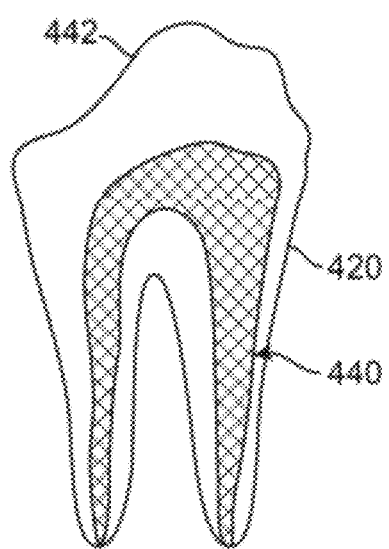
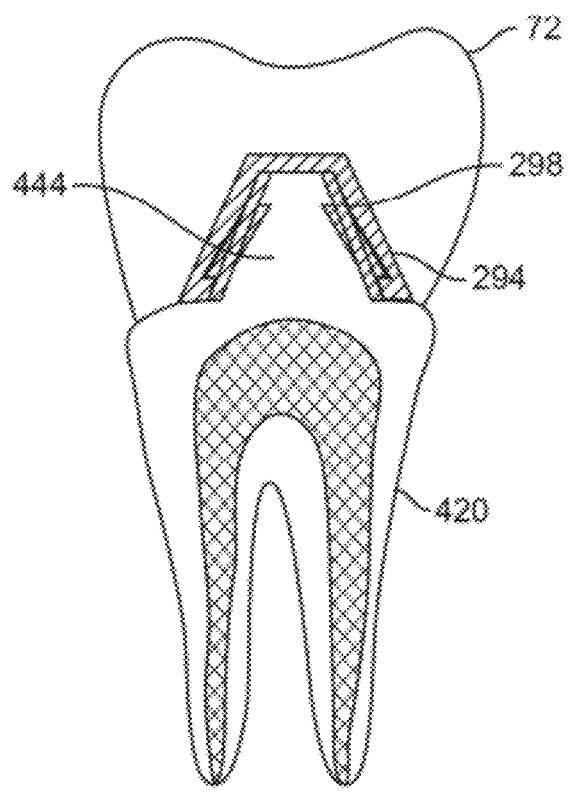
FIG. 42A
FIG. 42B

ABUTMENT DEVICES AND METHODS FOR NATURAL TEETH

FIELD OF THE INVENTION

The present invention relates to methods and apparatus for retaining one or more dental prostheses in a mouth of a user. More particularly, the present invention relates to methods and apparatus for retaining one or more dental prostheses in a manner which facilitates placement and removal via an actuation mechanism such as a shape memory material from an anchoring implant and/or abutment.

BACKGROUND OF THE INVENTION

The use of dental prostheses to replace missing or damaged teeth is commonplace. Typically, artificial roots, or implants, are implanted into the bone of the patient's jaw and are used to provide structural support to an intermediate abutment. One or more artificial replacement teeth or crowns are then fastened to the abutment typically by cements or screws.

FIGS. 1A to 1D illustrate partial cross-sectional side views of one example for implanting a typical crown within the mouth of a patient. Depending upon the number of teeth to be replaced, one or more holes may be bored within the bone of the jaw. As shown in FIG. 1A, a portion of the gums or gingiva 14 may be cut open to expose the underlying bone 10, e.g., maxilla or mandible, into which a drill bit 16 may be used to bore open a hole 12. An anchoring dental implant 18, optionally threaded, may be implanted within hole 12 and covered by gingival 14 to allow for healing and for the implant 18 to take hold within bone 10, as shown in FIG. 1B.

Once the implant 18 has been desirably positioned within bone 10, an abutment assembly 20 may be securely attached to implant 18, e.g., by a threaded pin 22 coupling to an implant receiving well 26 defined within implant 18 such that abutment 24, which defines a portion projecting through gingival 14 from implant 18 once coupled to implant 18, as shown in FIG. 1C. With abutment 24 secured to implant 18, crown 28 which defines crown opening 30 may be secured upon abutment 24 by utilizing a number of securement mechanisms, such as cement or a fastener such as a screw. Other securement mechanisms have also included interference fitting, such as with a cross-bar or O-ring type attachment, magnets, etc.

Because the implants, abutments, and crowns are subjected to high compressive and shear forces, initial positioning of the crowns is important not only to provide adequate structural support but also to ensure patient comfort. However, while utilizing cement to attach the crown to the abutment initially allows for aligning the crown more naturally with the dentition of the patient, the tolerance for mistakes is low once the cement has set because of the difficulty and expense in removing a cemented crown from the abutment. Screw-type retention devices may also provide for good securement of the crown to the abutment, but occlusal contact within the patient dentition is often misaligned resulting in a variety of complications. For instance, misaligned crowns result in a compromised occlusal table which in turn may lead to chipping of the crowns as well as poor aesthetic appearance of the patient's dentition.

Previous devices have attempted to create removable denture retention devices, such as that disclosed in U.S. Pat. No. 5,516,288, which is incorporated herein by reference in its entirety. Such systems are described which implant a screw within the jawbone of the patient while utilizing an abutment structure coupled to the implant portion via a ball joint made of shape memory materials. A restorative crown or dental replacement member is then attached to the abutment via conventional retention methods. However, such a device fails to disclose the use of shape memory materials utilized in the interaction between the abutment and the crown or bridge itself, as described in further detail below, as such an interaction facilitates the retention and retrieval of the crown or bridge from the abutment and/or implant.

Accordingly, there exists a need for methods and devices which are efficacious in facilitating not only the retention of oral appliances or prostheses, such as crowns or bridges, along the dentition of a patient but also the removal and/or repositioning of the crown or bridge.

SUMMARY OF THE INVENTION

The assemblies described provide for mechanisms and methods to facilitate the adjustment or removal of an oral appliance or prosthesis, such as a crown or bridge, from a reconfigurable abutment assembly. In utilizing the abutment assemblies described herein, an anchoring implant may be bored into the bones within the mouth of the patient to provide for the structural support of the abutment assembly. Moreover, the implants and abutment assemblies described herein may be utilized in any number of locations within the mouth of the patient, for instance, along the maxilla or mandible or other locations within the body which may benefit from an adjustable abutment assembly as described herein. Additionally, although some of the examples illustrate the placement and/or removal of crowns, various other prostheses for placement within or along the patient dentition may be utilized with the retention devices described herein and are not intended to be limited to use with crowns.

One example of an abutment retaining assembly may have a projecting abutment portion which extends from a first or upper abutment portion to a second or lower abutment portion. A threaded pin may extend from the lower abutment portion for attachment to the implant, which may be bored into the underlying bone to serve as an anchor. Portions of the abutment retaining assembly may be fabricated from any number of biocompatible materials, e.g., gold alloys, stainless steel, nickel-titanium alloys, etc., and may be sized for positioning along the patient's dentition.

With the projecting abutment portion extending from the upper abutment portion, an upper retaining plate may be positioned atop the projecting abutment portion to which one or more compression plates or elements are attached. The compression plates or elements may extend along the projection abutment portion while secured between upper retaining plate and lower retaining portions along the upper abutment portion. The upper retaining plate, as well as the projecting abutment portion, may define an opening for receiving an engagement instrument which may be inserted temporarily within the opening and used to secure the abutment assembly to the anchored implant.

The compression plates or elements may be sized to extend longitudinally along the projecting abutment portion and may number from one element to as many as practicable depending upon their size, e.g., six elements, which are spaced circumferentially about the portion in a uniform manner. Each of the plates has a length with one or more straightened portions with at least one curved or arcuate portion along the length of the element which projects radially when each of the one or more elements are positioned adjacent to one another over portion.

The one or more compression plates or elements may be fabricated from various shape memory materials, e.g., nickel-titanium alloys such as Nitinol, such that the curved or arcuate portion may be preformed along the element. A phase change may be initiated in the element upon the application of energy, such as heat or electrical energy, to transition the element between its martensitic and austenitic phase such that the arcuate portion may self-flatten with respect to the length of the element. A current or energy, such as an electrical current may be applied to the one or more elements via an input lead contact and return lead contact. If more than a single element is utilized, each of the elements may be electrically coupled to one another to allow for each of the elements to be energized or heated. As the energy is applied to the one or more elements, the phase change may be initiated such that the arcuate portions of elements reconfigure from their curved shape to a straightened shape.

The crown may define a crown opening which is slightly larger in diameter than the abutment assembly in its straightened configuration so that as the crown is lowered upon the abutment assembly, the crown may be tightly fitted thereupon. A portion of the crown opening may further define a widened diameter formed by, e.g., an undercut, which is correspondingly sized to receive the arcuate portions of the elements in their widened diameter. Moreover, the crown may further define corresponding input lead contact and corresponding return lead contact which are positioned along the crown such that the corresponding contacts come into electrical communication with their respective contacts to allow for the transfer of energy directly through the crown and into the elements when the crown is secured to the abutment.

Once the crown has been desirably positioned upon the abutment assembly, the energy may be removed or ceased such that straightened arcuate portions of the elements reconfigure into their arcuate shape. As the arcuate portions reform, the elements may shorten in length thus retracting the upper retaining plate and radially expanding the arcuate portions into the widened diameter of the crown. The reconfigured arcuate portions compress the elements against the widened diameter thereby effectively preventing relative movement between the crown and the elements and locking the crown into position along the abutment.

In the event that the crown requires removal, replacement, or repositioning upon the abutment, energy may again be applied to the elements positioned within the crown through corresponding contacts. As the arcuate portions are reconfigured back into their straightened low-profile configurations, the compression against the interior of the widened diameter may be released and the crown may be adjusted or repositioned upon the abutment or simply pulled entirely off the abutment assembly. A substitute crown may be replaced upon the abutment, if so desired.

A power source may be electrically coupled to a controller, e.g., resistance heating controller, to control the current flow to the one or more elements either directly through the contacts or through the corresponding contacts. As the controller is utilized to control the amount of current, the one or more elements may rise in temperature due to resistance heating. The power source may comprise any number of power supplies, e.g., an AC outlet or batteries, and the power source and controller may be configured into various form factors. The power supplied may range from between, e.g., about 10 to 150 Watts, while the heating time for applying the power may range from, e.g., 0.1 to 2 seconds or longer.

Yet another example for a power source for reconfiguring the one or more elements may utilize inductive heating where the elements may be heated without any direct contact between the power source and the elements. An inductive heating assembly may be regulated with a controller-like variable output oscillator circuit which sends an alternating current through a conductor to one or more coils which then generates an alternating magnetic field between the coils which may be set apart in apposition and at a distance from one another. The distance between the coils may define a receiving channel which is sized to be positioned adjacent to or in proximity to the crown and/or one or more elements.

With the abutment assembly and/or crown positioned within the receiving channel, the alternating magnetic field may be created between the coils to form eddy currents in the one or more elements which causes the material to heat up due to electrical resistance and thus activates the shape memory material to initiate their shape change. The frequency of the alternating current and the magnetic field can be set between, e.g., 1 kHz and 1 MHz, depending on the size and configuration of the one or more elements and the targeted activation time. Moreover, the power consumption may range between about, e.g., 10 W to 5 kW.

In yet another variation of a dental retaining assembly, a ferromagnetic shape memory alloy (FSMA) may be configured to have a tapered circumferential edge but when exposed to a magnetic field, the plate may become reconfigured such that the FSMA plate maintains a straightened cylindrical shape from its tapered configuration. As the magnetic field is maintained, the crown defining a crown opening with a widened diameter formed by, e.g., an undercut, may be positioned upon the actuated FSMA plate such that a position of the FSMA plate corresponds to the position of widened diameter. With the crown desirably positioned upon the abutment, the magnetic field may be removed or terminated such that the plate reconfigures into its tapered configuration within the widened diameter and compresses crown into securement upon the abutment.

In yet another alternative, multiple implanted anchoring assemblies may be secured to the patient to allow for the securement of one or more partial bridges utilizing the mechanisms and methods described herein. Accordingly, one or more anchoring assemblies may be used to secure one or more partial bridges. In another example, an overdenture may be secured to the patient utilizing an implanted cross-bar configuration which incorporates one or more anchoring assemblies. The anchoring assemblies may similarly utilize the one or more elements to secure the overdenture within the patient mouth.

Alternatively, crown retention mechanisms which utilize various shape memory elements or sleeves may be utilized to secure one or more crowns and/or allow for selective removal or readjustment of the crowns, relative to the implant. Such retention mechanisms may utilize one or more shape memory materials as further described herein.

In one variation, the abutment may be comprised of a two-piece assembly having a first portion formed as a lower abutment which may be secured to the implant via a threaded pin. A portion of the lower abutment may protrude into a lower abutment shaft which defines a receiving cavity. The second portion of the abutment assembly may be formed as an upper abutment which extends in an upper abutment shaft towards the lower abutment. Portions of both lower and upper abutment may be fabricated from any number of biocompatible materials, e.g., gold alloys, stainless steel, nickel-titanium alloys, etc.

A guide shaft extending from the upper abutment shaft may be matingly received within the receiving cavity such that as the upper abutment is translated relative to the lower abutment, the guide shaft may be guided within the receiving cavity to ensure a controlled translation between the abutment portions.

In this example, the abutment assembly may have a sleeve which comprises one or more segments which extend between an upper and lower portion which are secured to respective portions of the lower and upper abutment via, e.g., one or more pins. The internal sleeve may be comprised of individual segments or from a slotted sleeve made from, e.g., stainless steel, plastic, nickel-titanium alloy, etc. Each of the segments which extend between the lower and upper abutment may have a radially arcuate or curved portion which projects outwardly relative to the abutment. A corresponding shape memory element such as a wire made from, e.g., nickel-titanium alloy, shape memory polymers, etc., may be secured to each arcuate or curved portion at a sleeve attachment and extend through the portion and into the lower abutment shaft where each wire passes through a corresponding wire channel for attachment within the abutment at attachment.

Each wire may have a length which allows the arcuate or curved portion to remain in a radially curved shape with the wires in an un-tensioned state such that the portion secures the sleeve and abutment to the coping and crown. In the event that the crown requires removal, replacement, or repositioning upon the abutment assembly, energy may be applied or removed from the shape memory wires positioned within the crown. As energy is applied or removed (e.g., as described hereinabove), a phase change is initiated such that each shape memory wire contracts and imparts tension causing the sleeve to reconfigure to a low profile configuration. With the curved portions retracted relative to the coping, crown may be readily removed from the assembly. When the energy is removed, the wires may cool and re-initiate a phase change such that their lengths increase to their initial lengths and the sleeve reconfigure into their resting profile.

Another variation of an abutment assembly may utilize a laterally-oriented spring design. Each element or strip may be attached to a corresponding biasing element, e.g., spring, which extends laterally between an abutment attachment along the lower or upper abutment shaft and biasing element attachment located along an inner surface of the arcuate portion of element or strip. Biasing element may be fabricated from any variety of materials, e.g. stainless steel, titanium, etc. Another variation of an abutment assembly may utilize a post spring design. In this variation, a biasing element, e.g., spring, may be longitudinally positioned to extend over both the lower abutment shaft and upper abutment shaft.

In yet another variation, the abutment assembly may optionally comprise an inner sleeve and outer sleeve extending between and coupled to lower and upper abutment. Inner sleeve may be comprised of, e.g., a slotted sleeve made of plastic or metal such as stainless steel or shape memory material which functions as a biasing spring element. Each longitudinal element or strip of the inner sleeve may define a radially curved or arcuate portion which bows outwardly from the abutment assembly and outer sleeve (positioned annularly relative to inner sleeve) may also define a curved or arcuate portion which also bows outwardly in a manner corresponding to the curved or arcuate portion of the inner sleeve.

With this constant radial force, the outer sleeve may remain locked against the coping and crown. When the assembly is actuated (e.g., heated), the curved or arcuate portion of the outer sleeve may straighten and push inwardly against the curved or arcuate portion of the inner sleeve to then allow for the removal or adjustment of the crown relative to the abutment assembly.

In another variation similar to the double-sleeve design but utilizing an inner sleeve having a circumferential bump or portion, an inner sleeve may be positioned annularly within the elements and similarly secured to both lower and upper abutment portions. The circumferential bump or portion may protrude radially against the inner surface of the shape memory elements and provide a biasing force which urges the shape memory elements to maintain their curved configuration for securement against the coping and crown. When actuated, each of the shape memory elements may straighten and push radially into each of the bumps or portions to release the abutment from the coping and allow for the removal or adjustment of crown.

In yet another variation, a polymeric spring or biasing element (such as a spring, rubber, or polyurethane, etc.) may provide for a radial biasing force between the abutment shaft and circumferentially positioned shape memory sleeve to secure the crown to the abutment. In this variation, the biasing element may generally comprise a ring-shaped member which is securely positioned along the abutment shaft such that an outer surface along a circumference of the biasing element may press upon an inner surface of shape memory sleeve. The sleeve may further define one or more slotted locking flaps which curve radially outward from a corresponding flap pivot positioned along an upper portion of the sleeve away from the abutment shaft.

Another variation of the polymeric biasing element with the flaps may comprise one or more insulating rings or sleeves (e.g., made from a plastic) may be positioned between an outer surface of the abutment shaft and an inner surface of the sleeve to provide for an electrically insulating feature between the two.

In yet another variation, a shape memory shape memory sleeve may be formed and shaped, e.g., with a mandrel, to form a tapered configuration which may be secured to an abutment shaft tapered in a corresponding manner. The tapered sleeve may be slotted to form several locking flaps which protrude from the tapered sleeve in an alternating manner to form a self-locking sleeve design. In this example, at least one or more locking flaps may protrude radially from the sleeve such that the flaps extend radially from a lower portion of the sleeve where the diameter of the sleeve is relatively larger. At least one or more additional locking flaps may extend radially from an upper portion of sleeve where the diameter of the sleeve is relatively smaller. The radially extending portions of each flap may be configured in an alternative pattern, although other configurations may be accomplished. Accordingly, the coping which may be tapered in a corresponding manner may be secured upon the tapered sleeve in a self-locking manner where the locking flaps projecting radially from a lower portion may lock to tapered coping via locking under cut and the locking flaps projecting radially from an upper portion may lock to the tapered abutment via locking under cut.

Another variation of an abutment assembly may have a taper cut sleeve feature where the abutment shaft itself may be comprised of a straight member rather than a tapered member. The shape memory sleeve may itself be tapered with one or more locking flaps extending radially outward to lock against the coping and/or crown. The shape memory sleeve may be tapered by grinding a sleeve having an initial cylindrical shape down to a tapered configuration with the flaps defined along a longitudinal direction.

Yet another example may utilize a shape memory sleeve positioned upon an angled abutment assembly to position the sleeve and crown at an angle relative to the implant portion. In this variation, the angled abutment may generally comprise an abutment interface which is secured into contact against the implant via a retaining screw which may be inserted through a channel defined within the abutment. A lower portion of the abutment adjacent to abutment interface may be aligned, e.g., in parallel with a longitudinal axis of implant to define an implant longitudinal axis. An upper portion of the abutment may thus form a portion which is angled relative to the abutment interface such that the abutment defines an abutment longitudinal axis. The upper portion of the angled abutment may thus be configured with an angle which may vary through a range, Θ, depending upon the desired angle of the crown relative to the implant.

As previously described, an upper portion of angled abutment may be secured to the implant such that the sleeve is angled relative to the implant. In this variation, the abutment assembly may be formed of a two-part assembly having the upper portion which may be secured to a separate lower angled abutment shim. While the upper portion may be comprised of an abutment which is non-angled, the angled abutment shim may form an interface which is secured to the implant via the retaining screw and an interface for securement to the upper portion which may be formed to have any number of angles. Accordingly, different shims of differing angles may be secured between the implant and upper portion to accommodate various orientations of the crown relative to the implant.

Another variation of an abutment assembly may have a rounded abutment which allows for adjustability over a range of angles once an implant has already been implanted into the patient. The sleeve may be secured to a rounded abutment having a rounded abutment interface which defines a guide slot through which retaining screw may be positioned for securement to the implant. The guide slot may form a singular slot or multiple directional slots which allows the rounded abutment to be directionally guided relative to retaining screw and implant. Thus, once the rounded abutment and sleeve has been desirably positioned and angled relative to the implant, the retaining screw may be secured to lock the rounded abutment to the implant. If readjustment is desired, the screw may be un-tightened to release the rounded abutment to be readjusted relative to the implant after which the screw may then be re-tightened.

Although particular shape memory sleeves are illustrated with the angled abutment variations, this is intended for illustrative purposes and is not intended to be limiting. Accordingly, any of the variations of sleeves or strips or elements may be used in combination with any of the angled abutment designs as shown and described herein.

In yet another variation which may be utilized with any of the abutment designs described herein, a shape memory sleeve having a non-circular cross-sectional circumference, e.g., elliptical, may be utilized for preventing rotation of the crown relative to the implant. Any number of non-circular shapes may be utilized with the abutment shaft and sleeve, e.g., triangular, rectangular, etc.

In yet another example of an alternative abutment assembly, a shape memory abutment may comprise an assembly having two or more split securement members. The shape memory abutment may be heat-treated with the split securement members extended. When assembled, the abutment may be chilled to its shape memory condition and split securement members may be crimped together and inserted into the threaded receiving channel of the implant. As the temperature of the abutment rises, the split securement members may expand and lock with the internal thread of the implant.

BRIEF DESCRIPTION OF THE DRAWINGS

FIGS. 18A and 18B show cross-sectional side views of another variation of an abutment assembly utilizing a post spring design.

FIG. 18C shows a perspective view of the post spring abutment assembly.

FIG. 22A shows a perspective view of the sleeve positioned upon the abutment with the flaps biased outwardly by the spring element.

FIG. 22B shows a perspective view of the spring element positioned upon the abutment with the sleeve removed for clarity.

FIG. 22C shows a cross-sectional side view of the two-piece abutment and the spring element locking the sleeve flaps against the crown.

FIGS. 27A to 27C illustrate an example for forming and positioning a self-locking sleeve upon an abutment.

FIGS. 32A to 32D illustrate an example of a how an angled abutment assembly may be secured.

FIG. 36A shows a cross-sectional side view of an example of a seal which may be utilized between the abutment-coping interface.

FIG. 36B shows a view of an example of the seal of FIG. 36A.

FIGS. 36C and 36D show partial cross-sectional perspective and detail views of an example of a seal interspaced between the abutment-coping interface.

FIGS. 37A and 37B show examples of alternative shape memory abutments which may comprise a split assembly.

FIGS. 38A and 38B illustrate partial cross-sectional side views of an example of how a split abutment may be positioned within an implant fixture.

FIGS. 39A and 39B illustrate partial cross-sectional side views of another example of how a split abutment may be positioned at an angle within an implant fixture.

FIG. 42A shows an example of a decayed tooth.

FIG. 42B shows a cross-sectional side view of a decayed tooth formed to have an abutment for securing a crown.

DETAILED DESCRIPTION OF THE INVENTION

In positioning and securing an oral appliance, such as a crown or bridge, within the mouth of a patient, the retaining assemblies described herein allow not only for secure attachment but also for adjustment of the crown or bridge along the patient's dentition. The assemblies described also provide for mechanisms and methods to facilitate the entire removal of the crown or bridge from the abutment. In utilizing the abutment assemblies described herein, any number of typical anchoring implants may be bored into the bones within the mouth of the patient to provide for the structural support of the abutment assembly. Moreover, the implants and abutment assemblies described herein may be utilized in any number of locations within the mouth of the patient, for instance, along the maxilla or mandible or other locations within the body which may benefit from an adjustable abutment assembly as described herein.

Figures 1A, 1B, 1C, 1D:
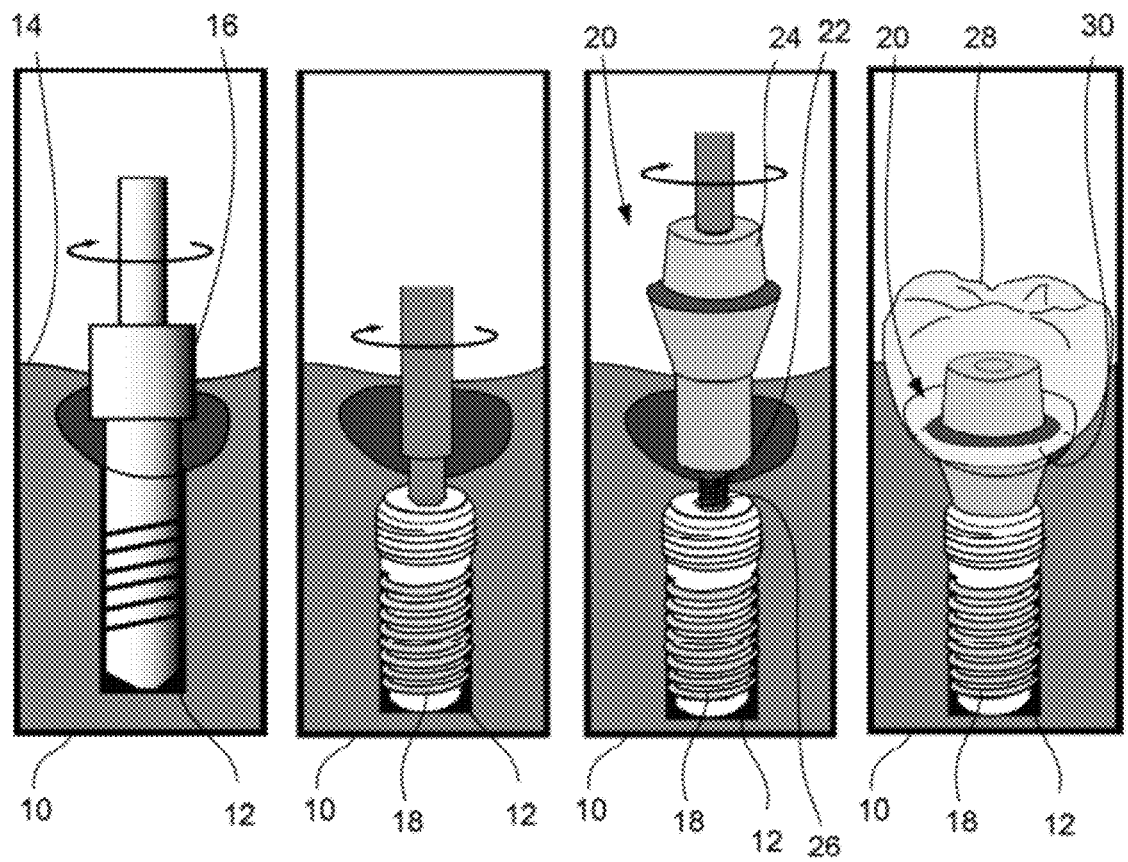
FIGS. 1A to 1D illustrate partial cross-sectional profiles of an example of placing an implant within a jawbone of a patient and attaching a crown thereto.
Figure 2B:
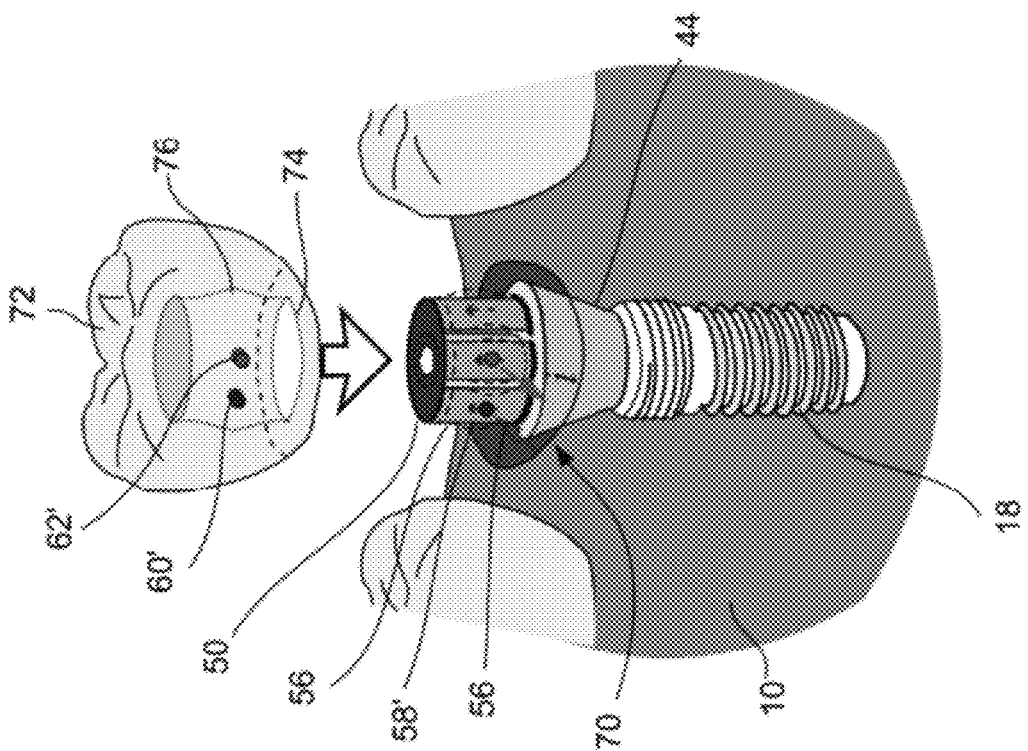
FIG. 2B illustrates a perspective view where energy may be applied to one or more shape memory compression plates or elements positioned along the abutment retaining assembly to configure the elements into a low-profile shape such that a crown may be received upon the abutment.
Figure 2A:
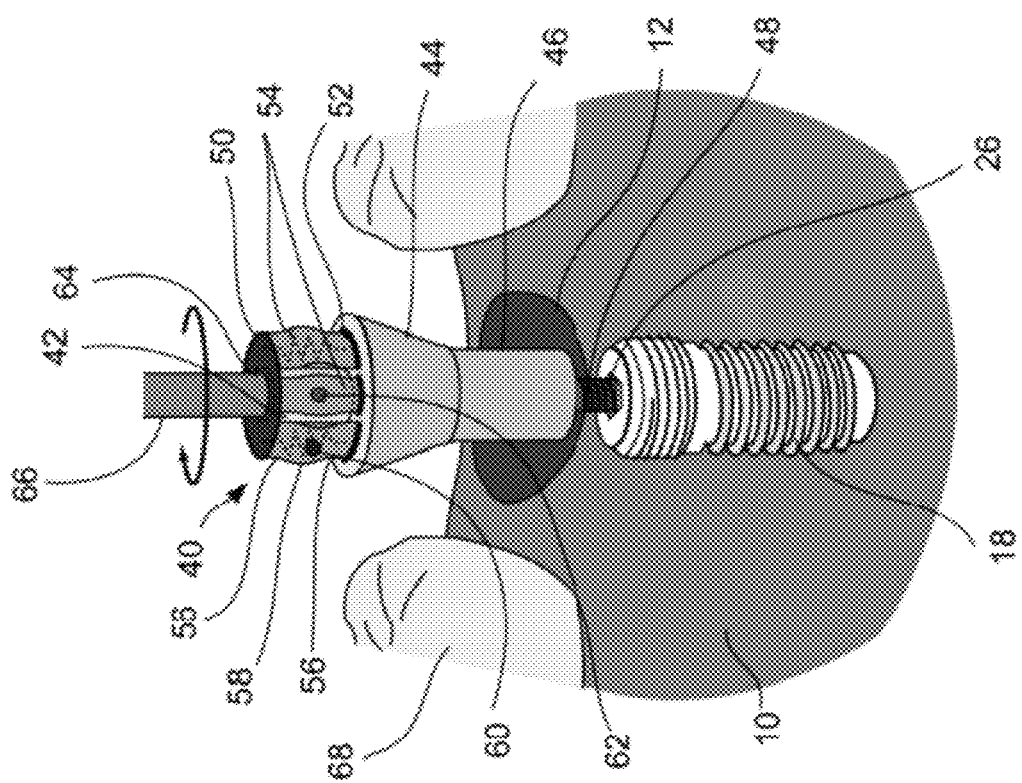
FIG. 2A illustrates a perspective view of attaching one variation of an abutment retaining assembly to a conventional implant.

Turning now to FIG. 2A, one example of an abutment retaining assembly 40 is illustrated as having a projecting abutment portion 42 which extends from a first or upper abutment portion 44, which is optionally tapered, to a second or lower abutment portion 46. A threaded pin 48 may extend from the lower abutment portion 46 for attachment to implant 18, which may be bored into the underlying bone 10 to serve as an anchor, and as previously described, which may be adjacent to another crown or pre-existing tooth or teeth 68. Portions of the abutment retaining assembly 40 may be fabricated from any number of biocompatible materials, e.g., gold alloys, stainless steel, nickel-titanium alloys, etc., and may be sized for positioning along the patient's dentition. For instance, the assembly 40 may have a diameter ranging from, e.g., 2 to 6 mm, with a length ranging from, e.g., 5 to 15 mm. These dimensions are exemplary and are not intended to be limiting.

With the projecting abutment portion 42 extending from the upper abutment portion 44, an upper retaining plate 50 may be positioned atop the projecting abutment portion 42 to which one or more compression plates or elements 54 are attached. The compression plates or elements 54 may extend along the projection abutment portion 42 while secured between upper retaining plate 50 and lower retaining portions 52 along the upper abutment portion 44. The upper retaining plate 50, as well as projecting abutment portion 42, may define an opening 64, which may be optionally keyed, for receiving an engagement instrument 66 which may be inserted temporarily within opening 64 and used to secure abutment assembly 40 to the anchored implant 18, e.g., by rotating abutment assembly 40 so as to screw threaded pin 48 into implant 18.

The compression plates or elements 54 may be sized to extend longitudinally along projecting abutment portion 42 and may number from one element to as many as practicable depending upon their size, e.g., six elements, which are spaced circumferentially about portion 42 in a uniform manner. Each of the plates are illustrated as having a length with one or more straightened portions 56 with at least one curved or arcuate portion 58 along the length of the element 54 which projects radially when each of the one or more elements 54 are positioned adjacent to one another over portion 42, as illustrated.

In one example, each of the elements 54 may range in length from, e.g., about 5 to 10 mm, with a thickness of e.g., about 0.5 to 1.5 mm. Moreover, the curved or arcuate portion 58 may have a radius which defines a height of, e.g., about 1 to 2 mm, relative to the thickness of the element 54 such that when element 54 is reconfigured into a straightened configuration, element 54 may extend an additional, e.g., 1.5 to 3 mm in length. These dimensions are provided as exemplary values and are not intended to be limiting. Variations in dimensions may be utilized as practicable.

The one or more compression plates or elements 54 may be fabricated from various shape memory materials, e.g., Nitinol, such that the curved or arcuate portion 58 may be pre-formed along the element 54. A phase change may be initiated in the element 54 upon the application of energy, such as heat or electrical energy, to transition the element 54 between its martensitic and austenitic phase such that the arcuate portion 58 may self-flatten with respect to the length of the element 54. As illustrated in FIG. 2B, current or energy 70, such as an electrical current i, may be applied to the one or more elements 54 via an input lead contact 60 and return lead contact 62. If more than a single element 54 is utilized, each of the elements 54 may be electrically coupled to one another to allow for each of the elements 54 to be energized or heated. The lead contacts 60, 62 may be positioned along a single element or different elements so long the elements are in electrical communication. As the energy is applied to the one or more elements 54, the phase change may be initiated such that the arcuate portions 58 of elements 54 reconfigure from their curved shape to a straightened shape, as shown in the figure.

With the arcuate portions 58 reconfigured into straightened portions 58', upper retaining plate 50 may be moved longitudinally with respect to upper abutment portion 44 while the elements 54 remain attached to their lower retaining portions 52. The resulting outer diameter of the elements 54 upon the abutment may be reduced from, e.g., about 6 mm to about 4 mm, to thus allow for the placement of a crown 72 upon the abutment assembly. Crown 72 may define a crown opening 74 which is slightly larger in diameter than the abutment assembly in its straightened configuration so that as crown 72 is lowered upon the abutment assembly, crown 72 may be tightly fitted thereupon. A portion of crown opening 74 may further define a widened diameter 76 formed by, e.g., an undercut, which is correspondingly sized to receive the arcuate portions 58 of elements 54 in their widened diameter, as described below. Moreover, crown 72 may further define corresponding input lead contact 60' and corresponding return lead contact 62' which are positioned along crown 72 such that the corresponding contacts 60', 62' come into electrical communication with their respective contacts 60, 62 to allow for the transfer of energy directly through the crown and into the elements 54 when the crown is secured to the abutment. To guide the crown 72 upon the abutment assembly, the opening 74 of crown 72 may be optionally keyed or shaped in a predetermined manner which corresponds with a configuration of the abutment such that advancement of the crown 72 upon the abutment may be achieved in a specified orientation, if so desired.

Figure 2C:
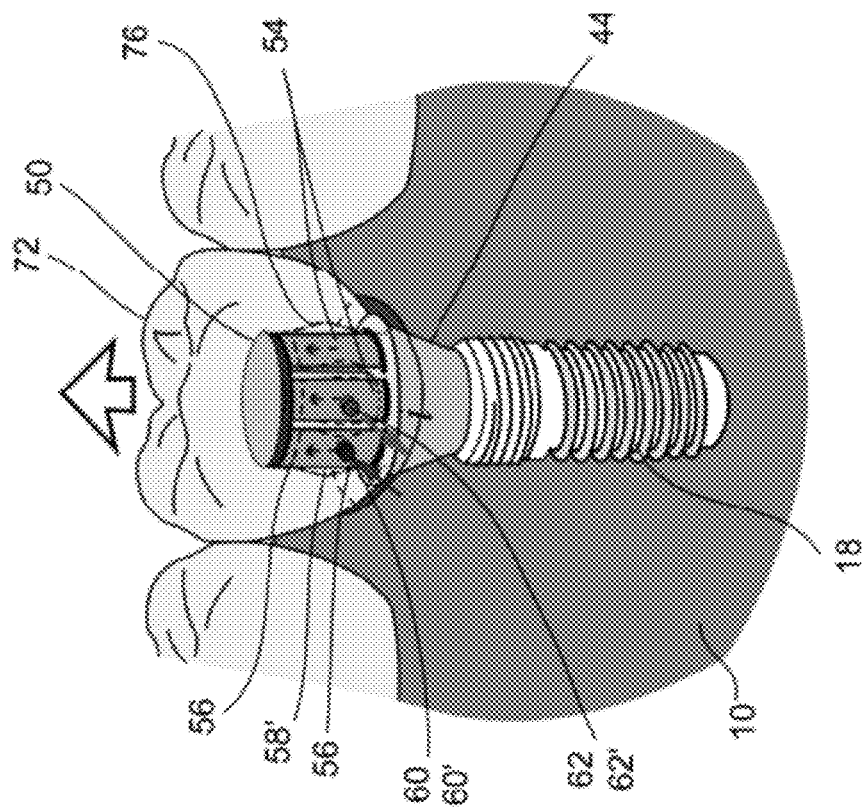
FIG. 2C illustrates a perspective view where the shape memory elements may be reconfigured into their expanded configuration to secure the crown upon the abutment.

Once crown 72 has been desirably positioned upon the abutment assembly, the energy may be removed or ceased such that straightened arcuate portions 58' of elements 54 reconfigure into their arcuate shape. As the arcuate portions 58 reform, the elements 54 may shorten in length thus retracting upper retaining plate 50 and radially expanding the arcuate portions 58 into the widened diameter 76 of crown 72, as shown in FIG. 2C. The reconfigured arcuate portions 58 compress the elements 54 against the widened diameter 76 thereby effectively preventing relative movement between the crown 72 and the elements 54 and locking the crown 72 into position along the abutment. The compressive force which may be generated between the elements 54 and the crown interior may range, e.g., between 10 N to 10 kN, to effectively lock the crown 72 into position.

Figure 2D:
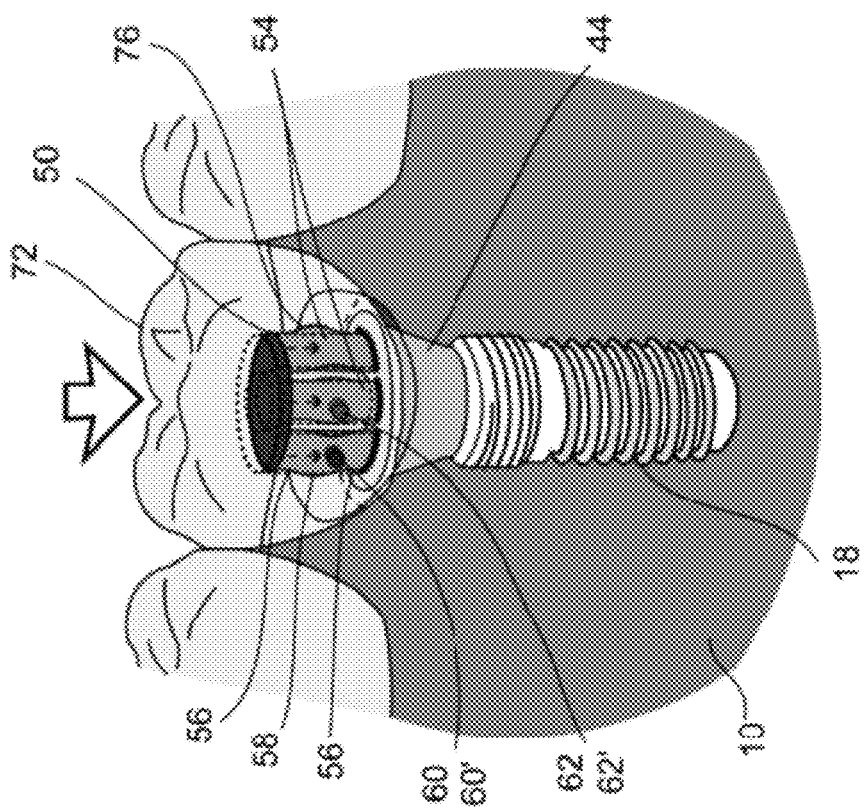
FIG. 2D illustrates a perspective view showing how energy may be reapplied to the elements through the crown to yet again configure the elements into a low-profile shape to allow for the repositioning or removal of the crown from the abutment.

In the event that crown 72 requires removal, replacement, or repositioning upon the abutment, energy may again be applied to the elements 54 positioned within the crown 72 through corresponding contacts 60', 62' which are in electrical communication with their respective contacts 60, 62, as shown in FIG. 2D. As the arcuate portions 58 are reconfigured back into their straightened low-profile configurations 58', the compression against the interior of widened diameter 76 may be released and crown 72 may be adjusted or repositioned upon the abutment or simply pulled entirely off the abutment assembly. A substitute crown may be replaced upon the abutment, if so desired.

Figure 3:
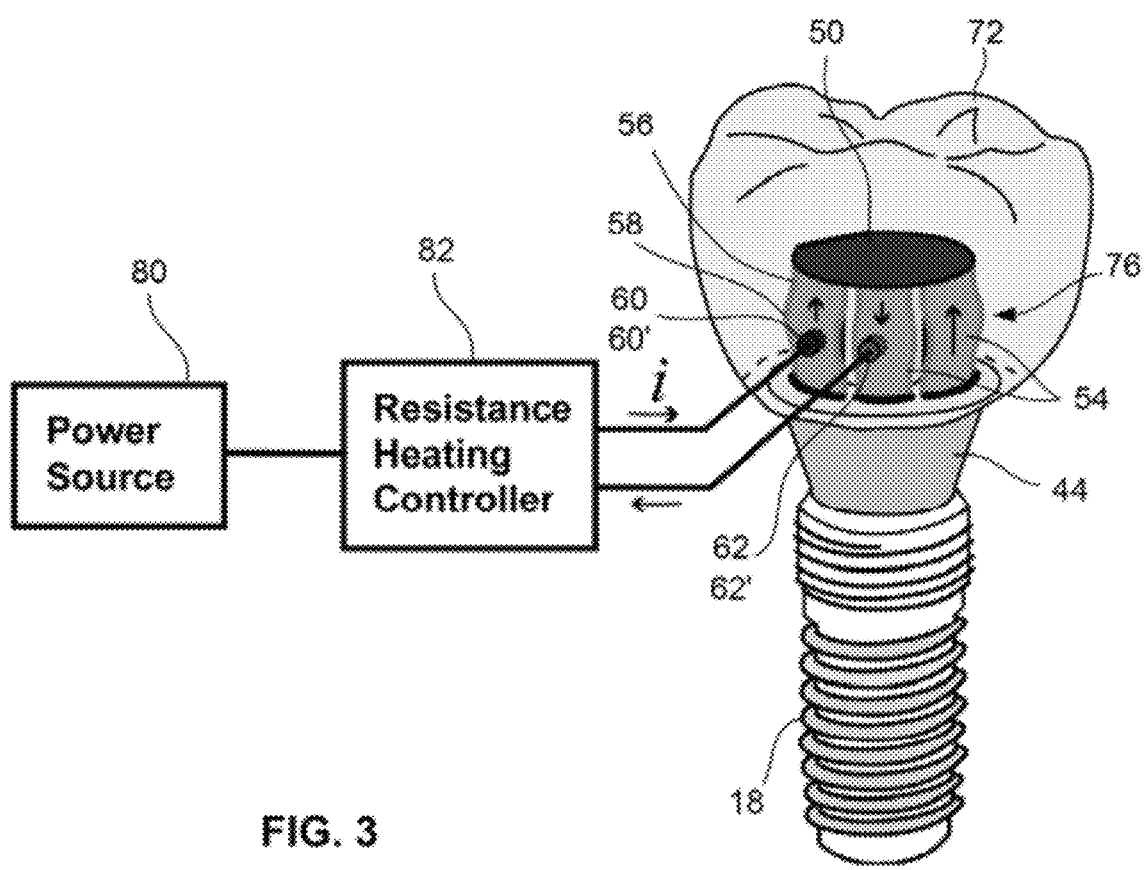
FIG. 3 illustrates an example of how energy may be applied via a power source and controller to the one or more elements.

In delivering the energy to the one or more elements 54 for initiating the phase change in the shape memory material, FIG. 3 illustrates one example which delivers a current to elements 54. A power source 80 may be electrically coupled to a controller 82, e.g., resistance heating controller, to control the current flow to the one or more elements 54 either directly through contacts 60, 62 or through corresponding contacts 60', 62' if delivered through crown 72. In either case, as the controller 82 is utilized to control the amount of current, the one or more elements 54 may rise in temperature due to resistance heating. The power source 80 may comprise any number of power supplies, e.g., an AC outlet or batteries, and the power source 80 and controller 82 may be configured into various form factors. For example, the heating assembly may be configured into a hand-held unit which is portable by the user or it may be configured into a larger non-portable unit. Because the size, configuration, and thermal conductivity of the elements 54 may be varied, the amount of power applied and the heating time may be varied accordingly. For instance, the power supplied may range from between, e.g., about 10 to 150 Watts, while the heating time for applying the power may range from, e.g., 0.1 to 2 seconds or longer.

Figure 4:
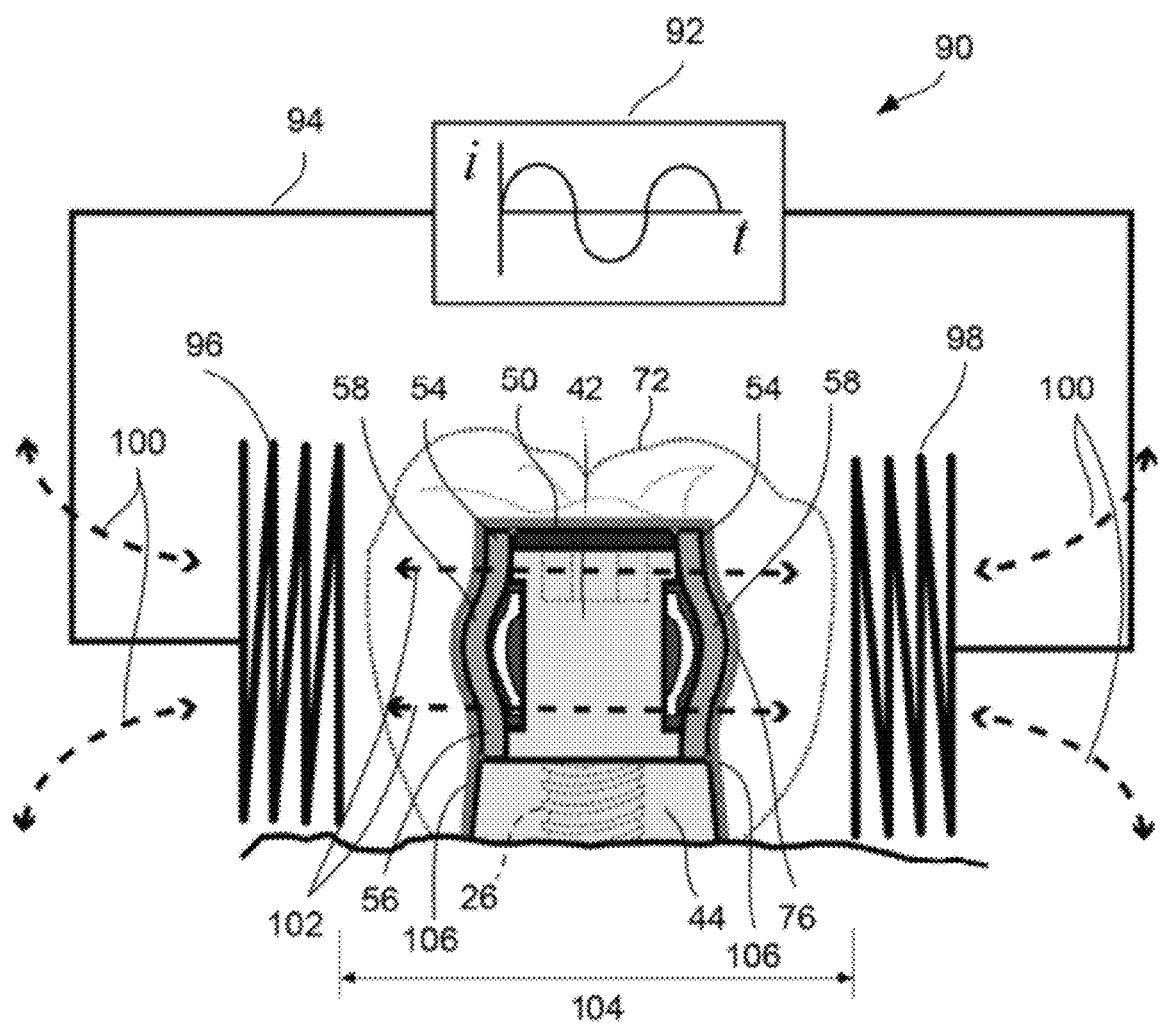
FIG. 4 illustrates schematically another example of how an alternating magnetic field may be applied to the one or more elements by inductively transferring energy to reconfigure the shape of the elements.

Yet another example for a power source for reconfiguring the one or more elements 54 is illustrated schematically in FIG. 4. Because this particular variation may utilize inductive heating, the elements 54 may be heated without any direct contact between the power source and the elements 54. As shown, an inductive heating assembly 90 may be regulated with a controller-like variable output oscillator circuit 92 which sends an alternating current i through conductor 94 to one or more coils 96, 98 which then generates an alternating magnetic field 100 between the coils 96, 98, which may be set apart in apposition and at a distance from one another. The distance between the coils 96, 98 may define a receiving channel 104 which is sized to be positioned adjacent to or in proximity to the crown 72 and/or one or more elements 54 such that when the elements 54 are to be reconfigured, the heating assembly 90 may be positioned upon the abutment assembly and/or crown 72 within the user's mouth.

With the abutment assembly and/or crown 72 positioned within receiving channel 104, the alternating magnetic field 100 may be created between coils 96, 98 to form eddy currents 102 in the one or more elements 54. These eddy currents 102, which may also be described as the movement of electrons in the material, causes the material to heat up due to electrical resistance and thus activates the shape memory material to initiate their shape change. The frequency of the alternating current i and the magnetic field can be set between, e.g., 1 kHz and 1 MHz, depending on the size and configuration of the one or more elements 54 and the targeted activation time. Moreover, the power consumption may range between about, e.g., 10 W to 5 kW. As described above, the heating assembly 90 may be configured, e.g., as a portable hand-held unit or as a larger non-portable unit. Additional details and examples of an inductive heating assembly are further shown in U.S. Pat. No. 6,710,314, which is incorporated herein by reference in its entirety.

Additionally in this and other examples, a sealant 106, such as a biodegradable silicone material, may be placed within the crown cavity to at least partially encompass or encase the abutment assembly to create a water-tight seal. This sealant 106 may completely encase the abutment assembly or it may seal just around a portion of the assembly, such as upper abutment portion 44.

Figure 5:
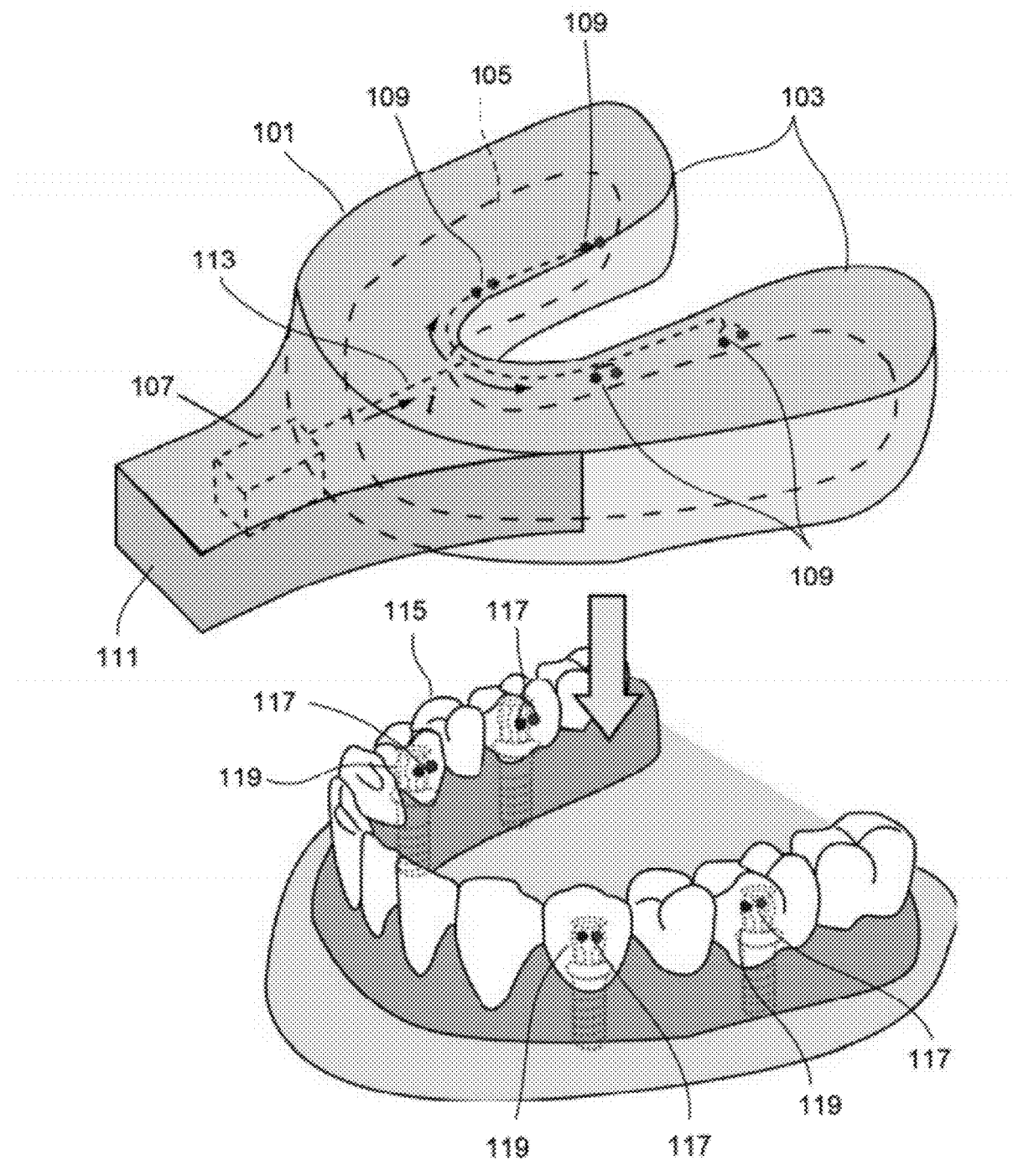
FIG. 5 illustrates a housing configured into a mouthpiece for applying energy to the compression elements.

In applying the energy (either resistive or inductive heating) to the one or more compression elements, one variation of a housing 101 configured into the form of a mouthpiece which may be inserted temporarily into the mouth of a patient is shown in the perspective assembly view of FIG. 5. Housing 101 may generally comprise two biteplates 103 which extend from a handle 111 and which define a receiving cavity 105 for receiving within or placement against a dental prosthesis such as an overdenture, crown, etc. Other variations may comprise a single biteplate or a partial biteplate depending upon the dental prosthesis to be secured. Moreover, handle 111, which generally extends from the mouth of the patient, may be removed or omitted entirely.

In either variation, one or more contacts 109 may be defined along the receiving cavity 105 and are in electrical communication with a power supply 107 through electrical conductor 113, which may be routed through the housing 101 to each of the respective contacts 109. In use, with one or more anchoring assemblies 119 secured within the patient's mouth, the dental prosthesis 115 (or prostheses) may either be positioned directly upon the respective anchoring assembly 119 or the dental prosthesis 115 may be positioned within receiving cavity 105 of housing 101. The housing 101 may then be positioned within the patient's mouth such that the respective dental prosthesis 115 is either placed upon a corresponding anchoring assembly 119 and/or such that the one or more contacts 109 positioned within housing 101 is aligned with a corresponding contact 117 positioned along the dental prosthesis. In either case, once the respective contacts 109, 117 are aligned, power supply 107 may be activated to actuate the compression plates to reconfigure and secure the dental prosthesis 115 to the one or more anchoring assemblies 119. Once the dental prosthesis 115 is fully secured, housing 101 may be removed from the patient's mouth. Housing 101 may be reinserted into the patient's mouth to reverse the securement process for readjusting or entirely removing the prostheses from the anchoring assemblies 119, if so desired. Moreover, housing 101 may be optionally used by the patient for inserting and/or removing prostheses such as overdentures on a daily basis or it may also be used by a practitioner for securing and/or removing any number of dental prostheses.

Figure 6B:
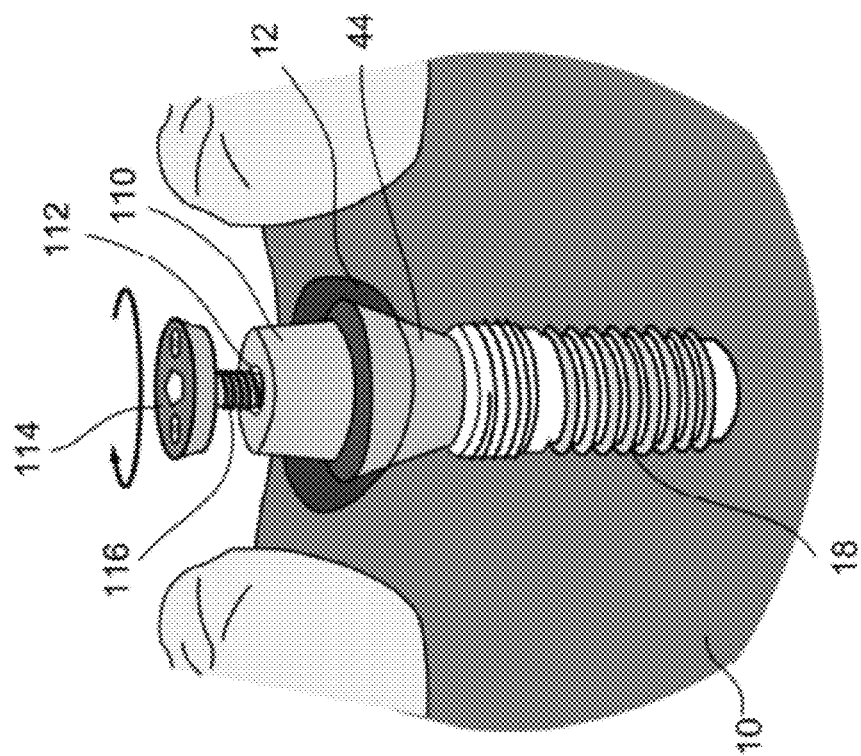
FIG. 6B illustrates a reconfigurable ferromagnetic shape memory alloy (FSMA) plate which may be secured to the abutment.
Figure 6A:
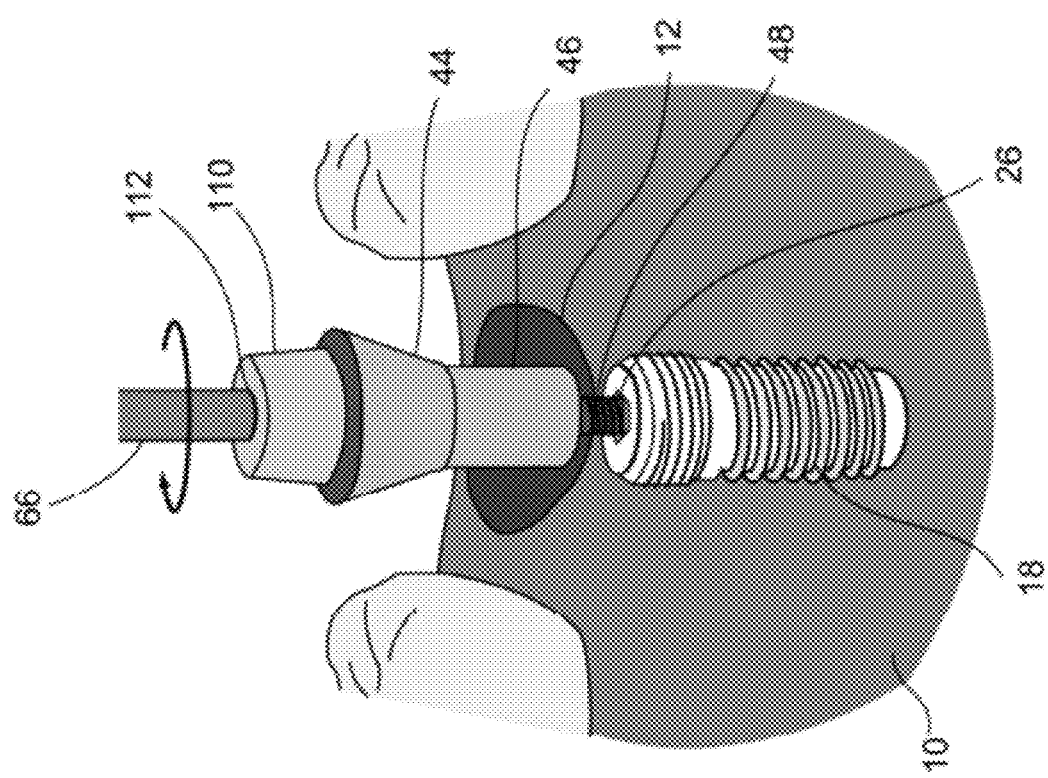
FIG. 6A illustrates an example of another variation for securing a crown where an abutment retaining assembly is secured to an implant.

In yet another variation of a dental retaining assembly, FIG. 6A illustrates an example of an assembly which may utilize a ferromagnetic shape memory alloy (FSMA), which are ferromagnetic materials which generally exhibit relatively large changes in shape and size when exposed to a magnetic field. In this variation, an abutment assembly having a projecting abutment portion 110 extending from an upper abutment portion 44 may be connected to an implant 18 via a threaded pin 26, as previously described. With the abutment secured to implant 18, a circular FSMA plate 114 having a tapered circumferential edge may be attached to the abutment opening 112 via a threaded retaining pin 116, which may be optionally keyed with respect to opening 112, as shown in FIG. 6B. Although illustrated as a circular element, FSMA plate 114 may be configured into various shapes or sizes depending upon the coupling mechanism to the crown.

Figure 6D:
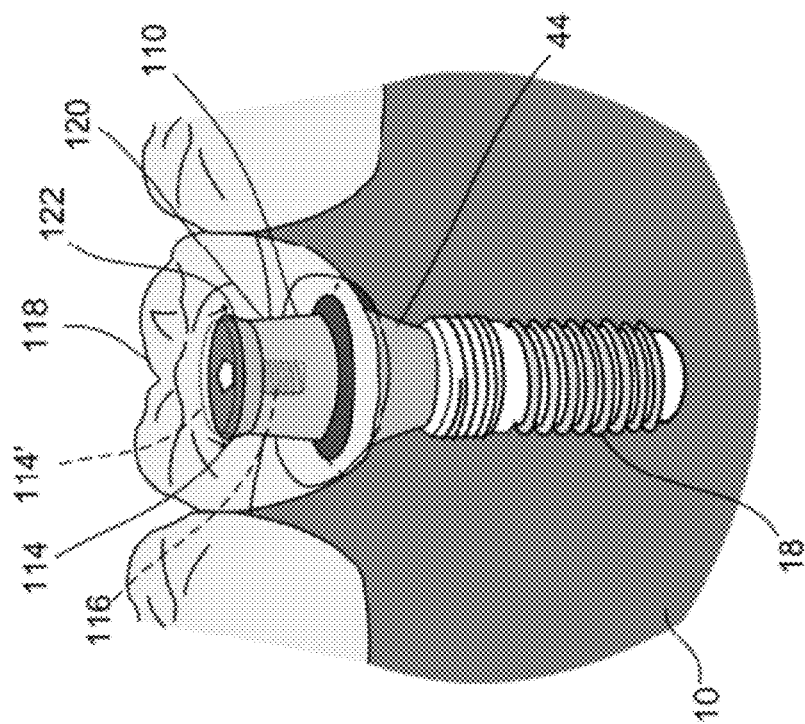
FIG. 6D illustrates the positioning of the crown upon the FSMA plate and the reconfiguration of the FSMA plate into its expanded profile to secure the crown thereto.
Figure 6C:
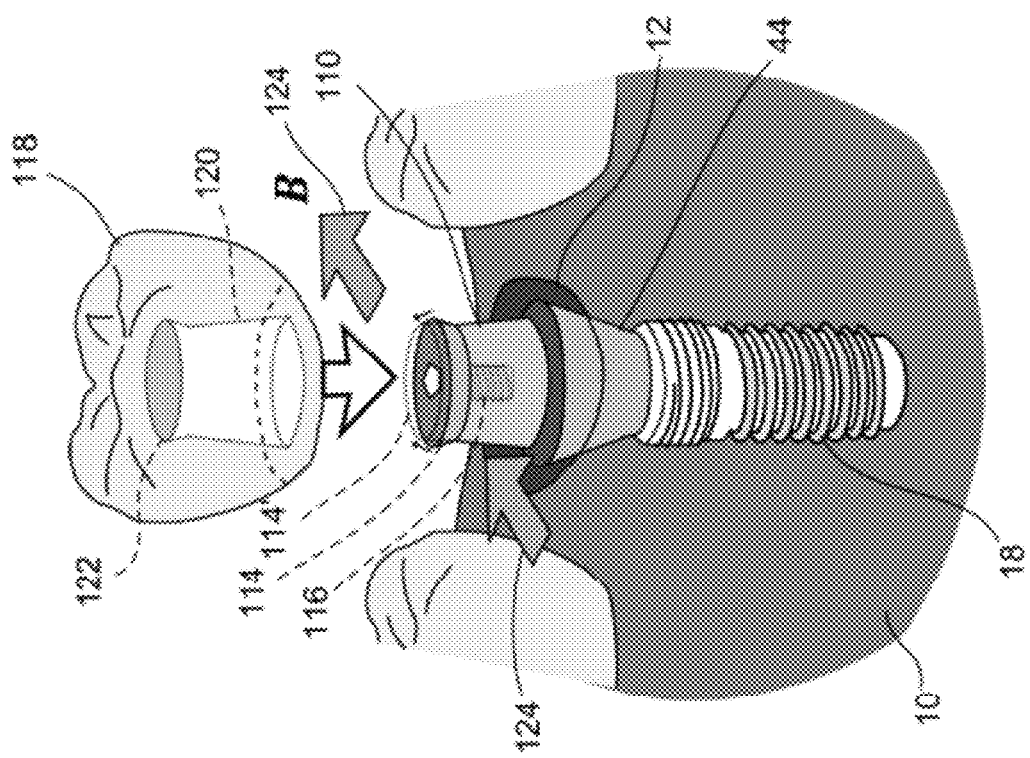
FIG. 6C illustrates a magnetic field applied to the FSMA plate to configure its shape into a low-profile to receive a crown.

The FSMA plate 114 may be configured to have a tapered circumferential edge but when exposed to a magnetic field 124, as shown in FIG. 6C, the plate 114 may become reconfigured such that the FSMA plate 114' maintains a straightened cylindrical shape from its tapered configuration. As the magnetic field 124 is maintained, crown 118 defining a crown opening 120 with a widened diameter 122 formed by, e.g., an undercut, may be positioned upon the actuated FSMA plate 114' such that a position of FSMA plate 114' corresponds to the position of widened diameter 122. With the crown 118 desirably positioned upon the abutment, the magnetic field 124 may be removed or terminated such that the plate 114 reconfigures into its tapered configuration within the widened diameter 122 and compresses crown 118 into securement upon the abutment, as shown in FIG. 6D. Also as described above, crown 118 may be configured to keyed to be positioned upon the abutment in a predetermined orientation, if so desired.

Figure 7A:
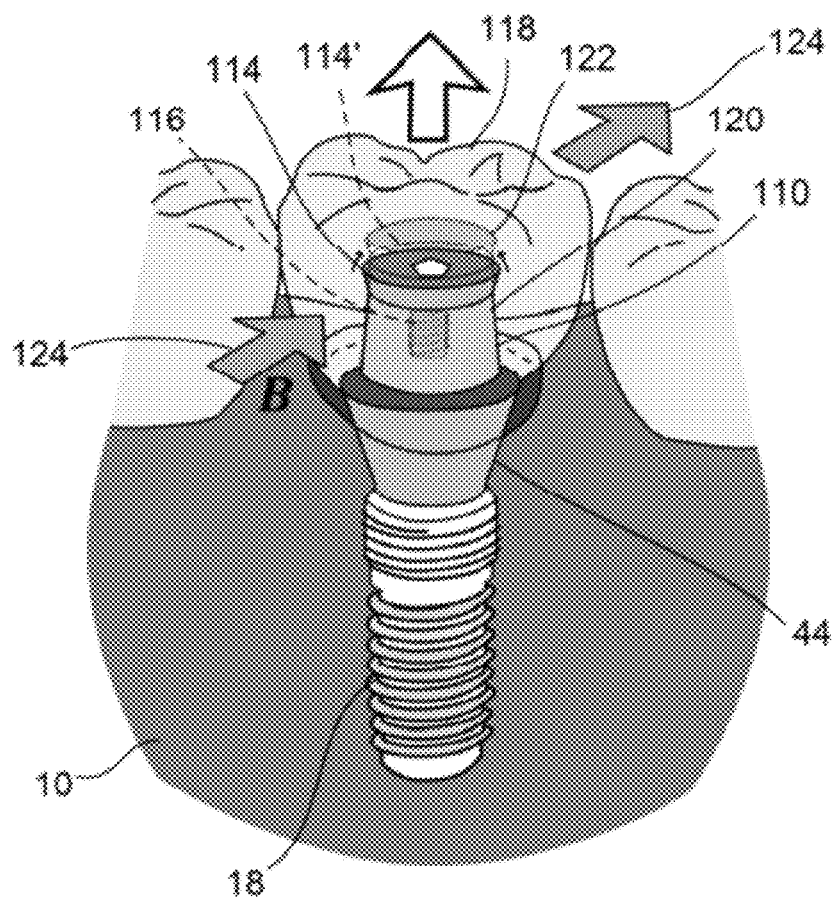
FIG. 7A illustrates the removal of the crown from the FSMA plate by application of a magnetic field to reconfigure the shape of the plate and allowing for the release of the crown.
Figure 7B:
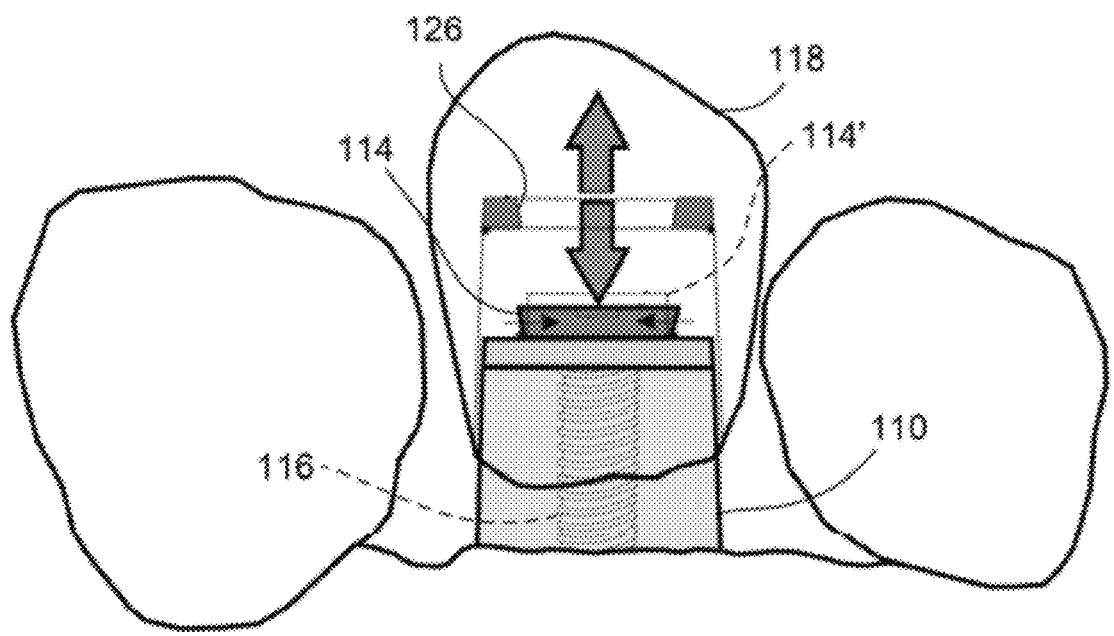
FIG. 7B illustrates a partial cross-sectional side view showing the reconfiguration of the FSMA plate and the release of the crown.

As shown in FIG. 7A, in the event that the crown 118 needs to be repositioned upon the abutment, readjusted, or removed entirely, the magnetic field 124 may be reapplied upon the crown 118 such that FSMA plate 114 reconfigures again from its tapered configuration to its straightened cylindrical configuration. FIG. 7B illustrates a partial cross-sectional side view of the FSMA plate 114 reconfigurable between its tapered configuration and its straightened configuration 114'. Also shown is another variation of the widened diameter utilizing a locking ring 126, which may be alternatively configured to define an undercut through which FSMA plate 114 may freely slide when straightened yet which interlocks against when the FSMA plate 114 is in its tapered configuration.

Figure 8:
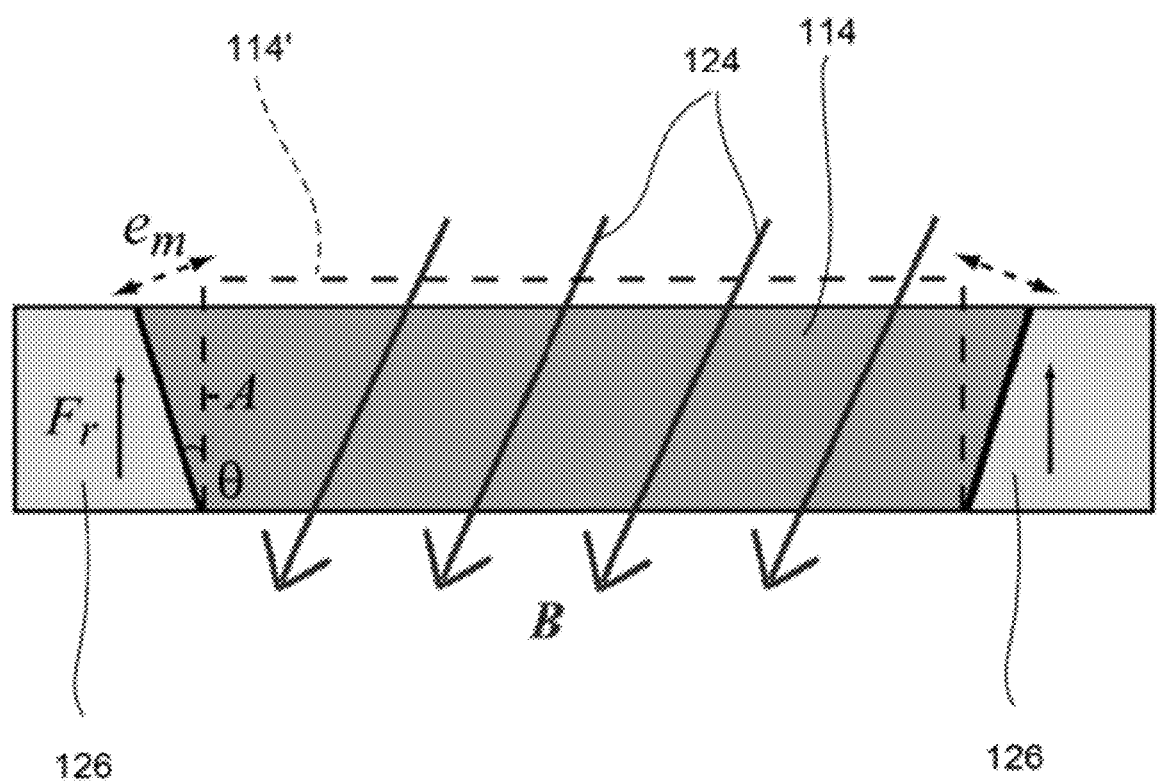
FIG. 8 illustrates a representative partial side view of an FSMA plate engaged against a widened diameter of the crown for securing the crown in position.

FIG. 8 illustrates a detail view of the locking interaction between the FSMA plate and the ring 126. With the FSMA plate 114' in its straightened configuration while under the magnetic field 124, plate 114' may freely slide into position through the ring 126. However, upon removal of the magnetic field 124, the FSMA plate 114' may reconfigure into its tapered configuration 114 such that the FSMA plate 114 is secured against the ring 126 to prevent movement of the crown relative to the plate 114. The plate 114 may be keyed relative to the ring 126 such that the crown is fitted upon the abutment in a predetermined orientation, if so desired.

In determining the amount of retention force retention force before yield $F_r$ between the plate 114 and the ring 126, the effective stress $\sigma_0$ may be initially calculated utilizing the following equation (1) while assuming that the FSMA is isotopic in nature.

$$\sigma_0 = \frac{1}{\sqrt{2}} \sqrt{\sigma_n^2 + 6\sigma_t^2} \tag{1}$$

where $\sigma_n$ represents the normal stress and $\sigma_t$ represents the tangential stress values. Expanding the formula (1) in terms of $\sigma_0$ and $\Theta$ which represents the undercut angle, the force may be calculated utilizing the following equation (2).

$$F_R = \frac{2\sqrt{2}A}{\sqrt{(5\cos^2 2\theta + 12\cos 2\theta + 7)}} \sigma_0 \tag{2}$$

where A represents the nominal cross-sectional area of the plate 114 against the ring 126, $\Theta$ represents the undercut angle, and $\sigma_0$ represents the effective stress. Thus assuming $\cos 2\theta \approx 1$, the equation (2) for calculating the retention force may be simply reduced to the following equation (3).

$$F_R = 0.577 A \sigma_0 \tag{3}$$

Figure 9:
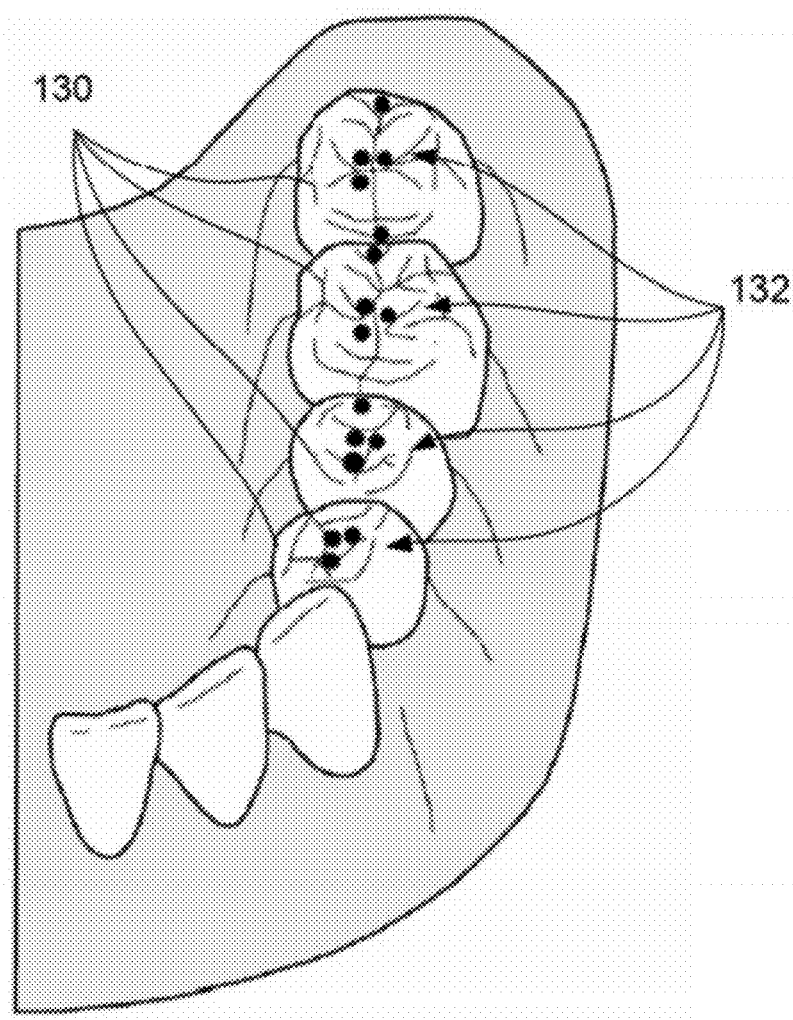
FIG. 9 shows a perspective view of one or more crowns or bridges which have been coupled to implants by utilizing the one or more elements to show how the crowns or bridges may be positioned along a patient's dentition to align the occlusal contact points for patient comfort and safety.

Because of the adjustable nature of the retention assemblies described herein, the crowns or bridges secured to the abutment assemblies may be adjusted in vivo to ensure that the dentition, once secured, aligns properly. As indicated in the perspective view of FIG. 9, multiple anchored crowns 130 as shown which have been secured to the patient. The resulting occlusal contact points 132, which are those areas along the occlusal surface which contact the opposed tooth or teeth as the jaw is articulated, may thus be adjusted utilizing the mechanisms and methods described to ensure proper alignment for patient comfort, safety, and reliability of the crowns.

Figure 10:
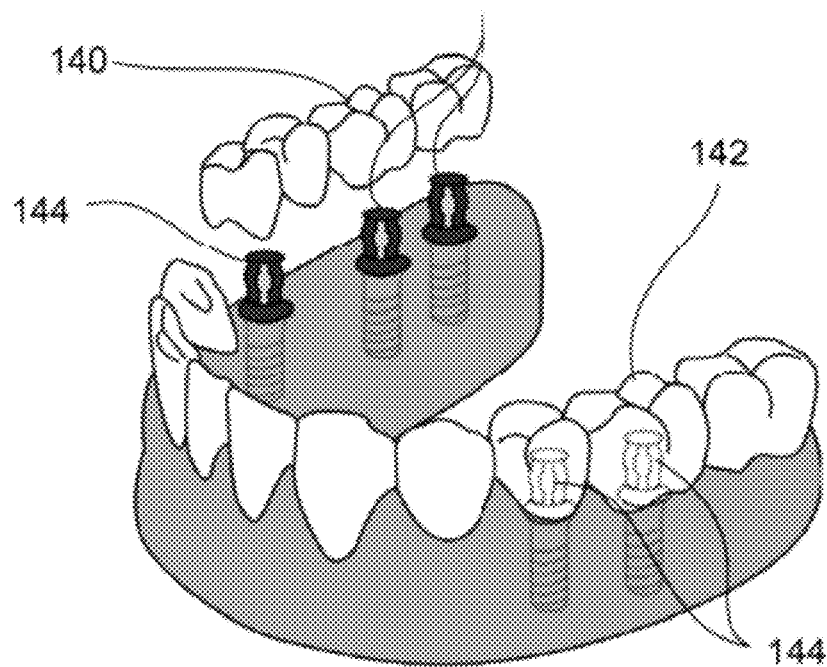
FIG. 10 shows a perspective view of multiple implants and abutment assemblies utilizing the reconfigurable plates or elements herein to secure individual crowns or bridges to a patient's bone.
Figure 11:
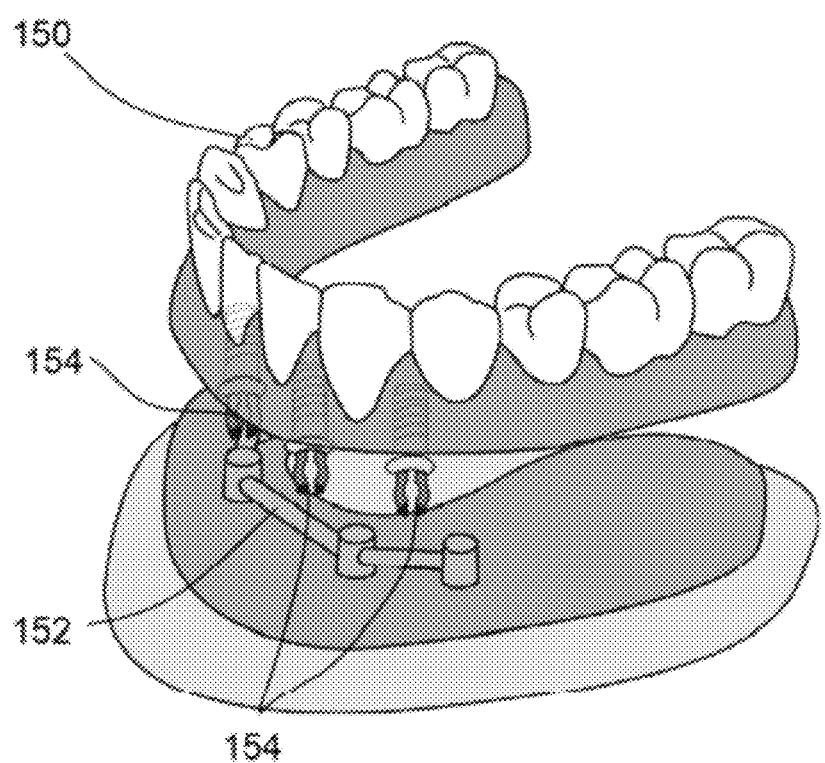
FIG. 11 shows a perspective view of another example where an implanted cross-bar may be utilized to secure an overdenture to the patient's bone via the reconfigurable plates or elements.

Although the previous examples have illustrated a single crown placed upon a single corresponding abutment assembly, alternative variations may be utilized. For instance, FIG. 10 illustrates an example where multiple implanted anchoring assemblies 144 may be secured to the patient to allow for the securement of one or more partial bridges 140, 142 utilizing the mechanisms and methods described herein. Accordingly, one or more anchoring assemblies 144 may be used to secure one or more partial bridges. In another example, FIG. 11 shows another variation where an overdenture 150 may be secured to the patient utilizing a cross-bar 152 configuration implanted into the patient's bone. The overdenture 150 itself may incorporate one or more anchoring assemblies 154 which extend away from the overdenture 150 for coupling to the cross-bar 152. The anchoring assemblies 154 may similarly utilize the one or more elements for securing the overdenture 150 within the patient mouth as they may be configured to operate in a similar manner as those previously described. For instance, rather than transitioning from an extended to a compressed configuration for compression against the interior of the dental prosthesis, anchoring assemblies 154 may transition from to an extended configuration to a compressed configuration which compresses over and/or upon the cross-bar 152 to secure the overdenture 150 thereto.

Figure 12:
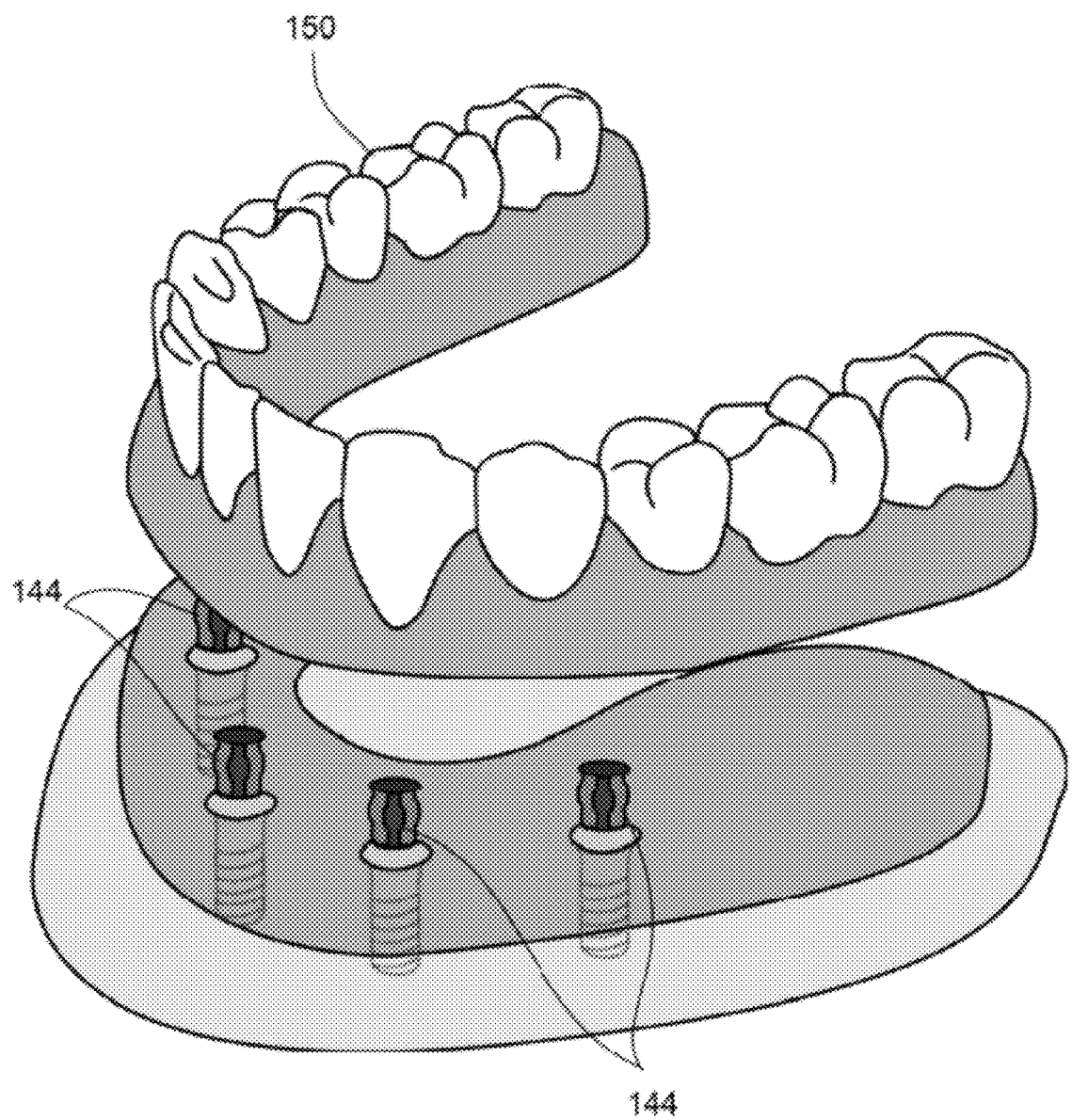
FIG. 12 shows a perspective view of yet another example where one or more anchoring assemblies may be used to secure a dental prosthesis, such as an overdenture, to the patient's mouth.

In yet another example, as shown in the perspective view of FIG. 12, one or more anchoring assemblies 144 may be secured to the patient's mouth for coupling to a dental prosthesis such as an overdenture 150. In this example, the overdenture 150 may define one or more receiving channels corresponding to the one or more anchoring assemblies 144 such that reconfiguration of the compression plates along anchoring assemblies 144 may compress and secure against an interior surface of each respective receiving channel in a manner as described above to secure the overdenture 150 within the patient's mouth. Removal of overdenture 150 may be effected utilizing any of the variations described herein to allow for daily removal of overdenture 150, if so desired.

Figure 13:
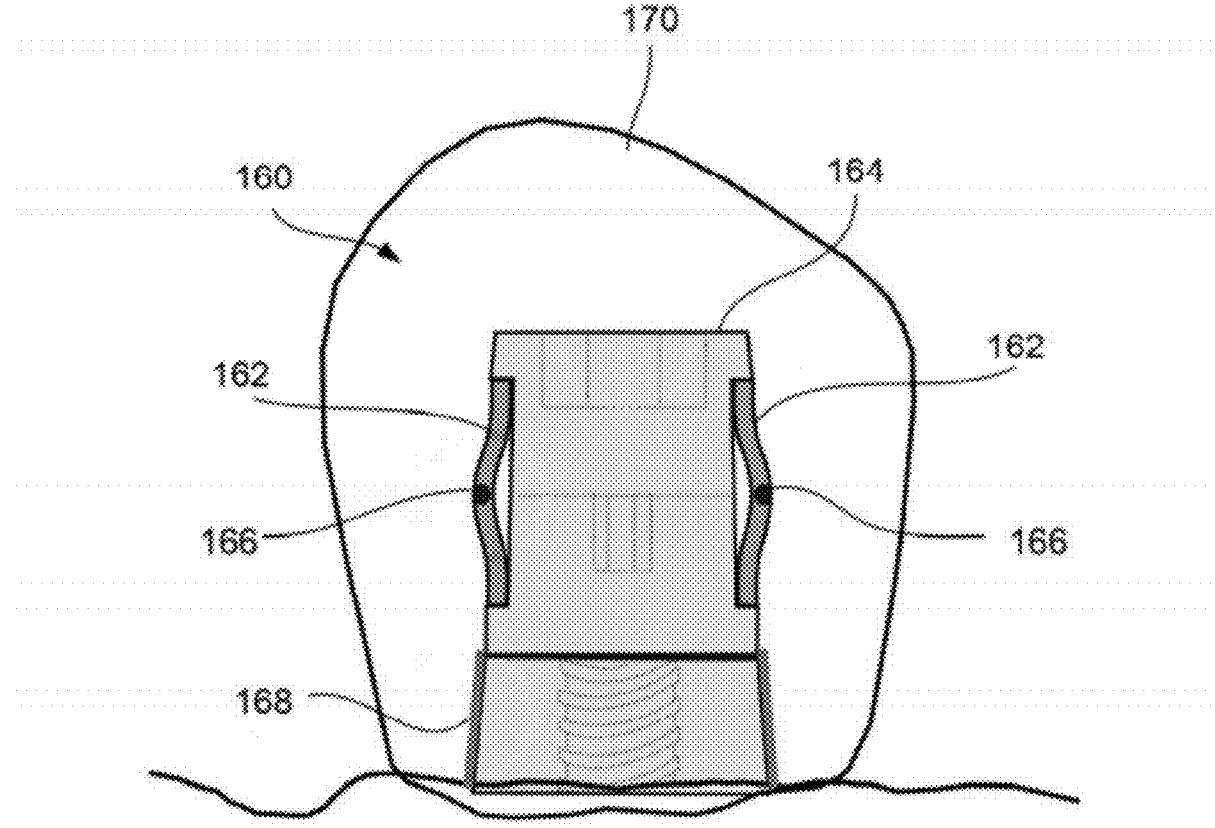
FIG. 13 shows yet another example of an anchoring assembly utilizing compression plates comprised of biased spring elements which are reconfigured by a shape memory wire.

Another variation of the anchoring assembly is illustrated in the side view of FIG. 13, which shows an anchoring assembly 160 utilizing compression plates which are comprised of biased elements 162, e.g., leaf springs, which are prefabricated to be biased in an outwardly radial direction relative to the abutment assembly 164 to which they are mounted. The biased elements 162 may be fabricated into individual plates from a material such as spring stainless steel which are formed to have a curved or arcuate portion rather than from a shape memory material, as previously described. Thus, when the elements 162 are positioned within or along the abutment assembly 164, the curved or arcuate portions may extend radially and function as a biased spring element.

Each of the elements 162 may define a channel or opening through which a separate shape memory wire 166, such as a wire made from a nickel-titanium alloy, may pass through.

Shape memory wire 166 may be stretched relatively taut through elements 162 such that when wire 166 is energized, as previously described, the wire 166 may shorten in length to compress the curved or arcuate portions of elements 162 into a flattened configuration against abutment assembly 164 to allow for the placement or positioning of a dental prosthesis, such as a crown 170, over abutment assembly 164. Once crown 170 has been desirably positioned, energy may be removed from wire 166 to allow for its re-lengthening which in turn may allow for elements 162 to relax back into its curved or arcuate shape such that elements 162 compress against the interior surface of crown 170 thus locking or securing crown 170 into position upon the anchoring assembly 160. As previously described, a sealant 168 may also be optionally positioned upon the crown interior for forming a water-tight seal against the anchoring assembly 160 to prevent the entry of food and liquids into the crown interior.

Alternatively, crown retention mechanisms which utilize various shape memory elements or sleeves may be utilized to secure one or more crowns and/or allow for selective removal or readjustment of the crowns relative to the implant. Such retention mechanisms may utilize one or more shape memory materials as further described herein.

Figure 14A:
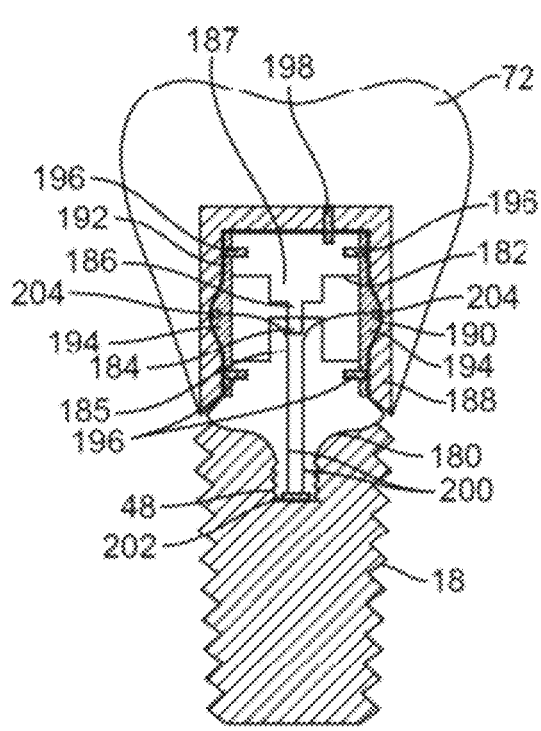
FIGS. 14A and 14B show cross-sectional side views of another example of an abutment retaining assembly utilizing shape memory wire design.
Figure 14B:
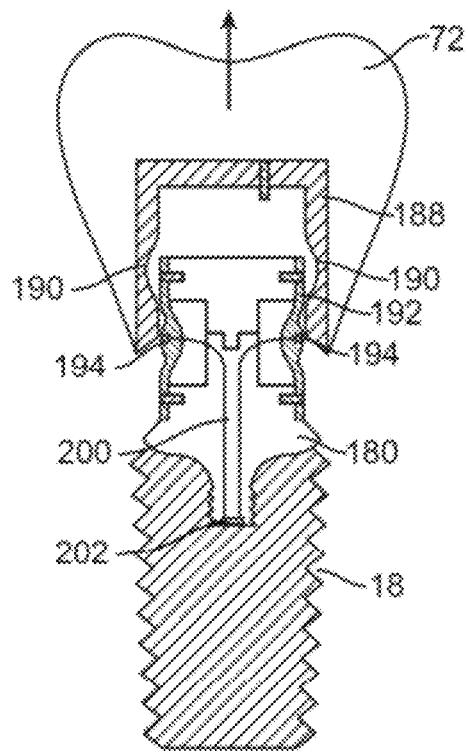

FIGS. 14A and 14B show cross-sectional side views of another example of an abutment retaining assembly utilizing a shape memory wire design. In this variation, the abutment may be comprised of a two-piece assembly having a first portion formed as a lower abutment 180 which may be secured to implant 18 via threaded pin 48. A portion of the lower abutment 180 may protrude into a lower abutment shaft 185 which defines a receiving cavity 184. The second portion of the abutment assembly may be formed as an upper abutment 182 which extends in an upper abutment shaft 187 towards the lower abutment 180. Portions of both lower and upper abutment 180, 182 may be fabricated from any number of biocompatible materials, e.g., gold alloys, stainless steel, nickel-titanium alloys, etc.

A guide shaft 186 extending from the upper abutment shaft 187 may be matingly received within the receiving cavity 184 such that as the upper abutment 182 is translated relative to the lower abutment 180, the guide shaft 186 may be guided within receiving cavity 184 to ensure a controlled translation between the abutment portions 180, 182.

In this example, the abutment assembly may have an internal sleeve 192 which comprises one or more segments which extend between an upper and lower portion which are secured to respective portions of the lower and upper abutment 180, 182 via, e.g., one or more pins 196. The internal sleeve 192 may be comprised of individual segments or from a slotted sleeve made from, e.g., stainless steel, plastic, nickel-titanium alloy, etc. Each of the segments which extend between the lower and upper abutment 180, 182 may have a radially arcuate or curved portion 194 which projects outwardly relative to the abutment. A corresponding shape memory element 200 such as a wire made from, e.g., nickel-titanium alloy, shape memory polymers, etc., may be secured to each arcuate or curved portion 194 at a sleeve attachment 204 and extend through the portion 194 and into the lower abutment shaft 185 where each wire 200 passes through a corresponding wire channel 206 for attachment within the abutment at attachment 202.

As previously described, the abutment assembly may be received within crown 72 which may further incorporate a coping insert 188. The abutment assembly may include a shaft that fits into an opening within implant 72 and functions as an anchor within implant 72. Coping 188 may define an arcuate receiving portion 190 which matches a profile of curved portion 194 of internal sleeve 192 with a widened diameter for locking with curved portion 194. Additionally, coping 188 may also include an anti-rotation pin 198 coupling coping 188 to crown 72 to prevent crown 72 from rotating with respect to the abutment assembly.

Each wire 200 may have a length which allows the arcuate or curved portion 194 to remain in a radially curved shape with the wires 200 in an un-tensioned state such that portion 194 secures the sleeve 192 and abutment to the coping 188 and crown 72, as shown in FIG. 14A. In the event that crown 72 requires removal, replacement, or repositioning upon the abutment assembly, energy may be applied or removed from the shape memory wires 200 positioned within crown 72. As energy is applied or removed (e.g., as described hereinabove), a phase change is initiated such that each shape memory wire 200 contracts and imparts tension causing sleeve 192 to reconfigure to a low profile configuration, as shown in FIG. 14B. With the curved portions 194 retracted relative to the coping 188, crown 72 may be readily removed from the assembly. When the energy is removed, the wires 200 may cool and re-initiate a phase change such that their lengths increase to their initial lengths and sleeve 192 reconfigure into their resting profile.

Figure 15:
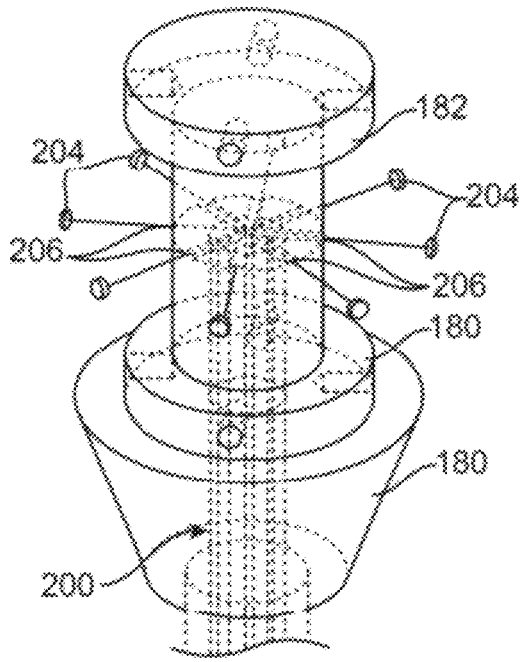
FIG. 15 shows a perspective view of several shape memory wires routed through the abutment.

FIG. 15 shows a perspective view of several shape memory wires 200 routed through the abutment 180 with the sleeve 192 removed for clarity. In this example, eight shape memory wires 200 are shown extending radially through corresponding wire channels 206 for attachment to a corresponding arcuate portion 194. However, fewer or greater numbers of wires 200 and alternative configurations may be utilized.

Figure 16A:
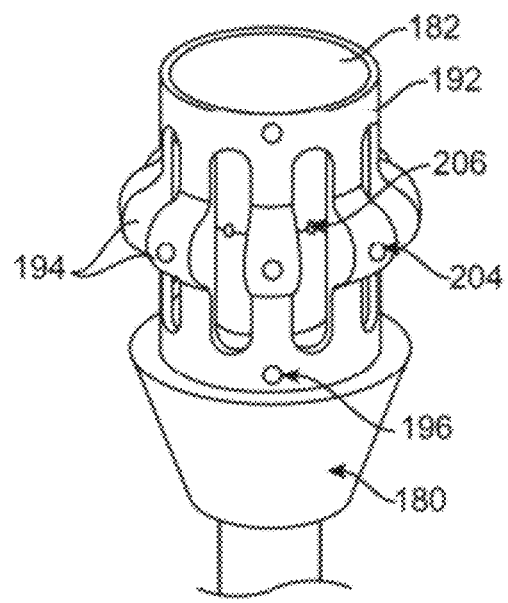
FIG. 16A shows a perspective view of the abutment assembly with the shape memory wires integrated into the shape memory component anchors.
Figure 16B:
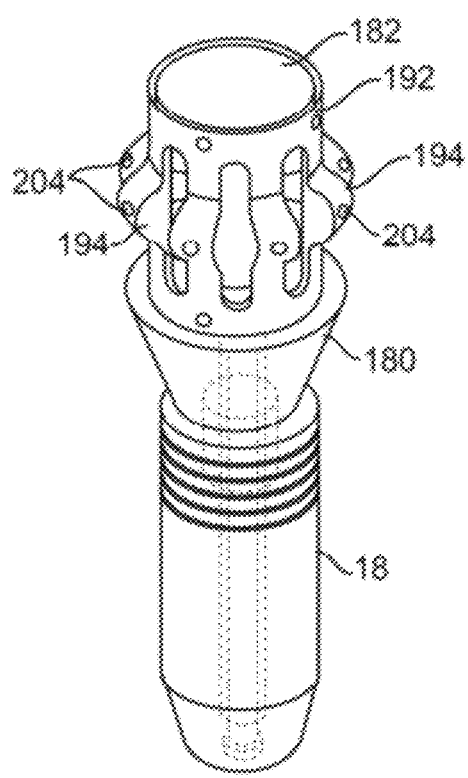
FIG. 16B shows another perspective view of the abutment assembly illustrating the positioning of the shape memory wires relative to the component anchors.

FIG. 16A shows a perspective view of the abutment assembly with the shape memory wires 200 integrated into the arcuate portions 194. FIG. 16B shows yet another perspective view of the abutment assembly illustrating the positioning of the shape memory wires 200 relative to the internal sleeve 102 and arcuate portions 194.

Figure 17A:
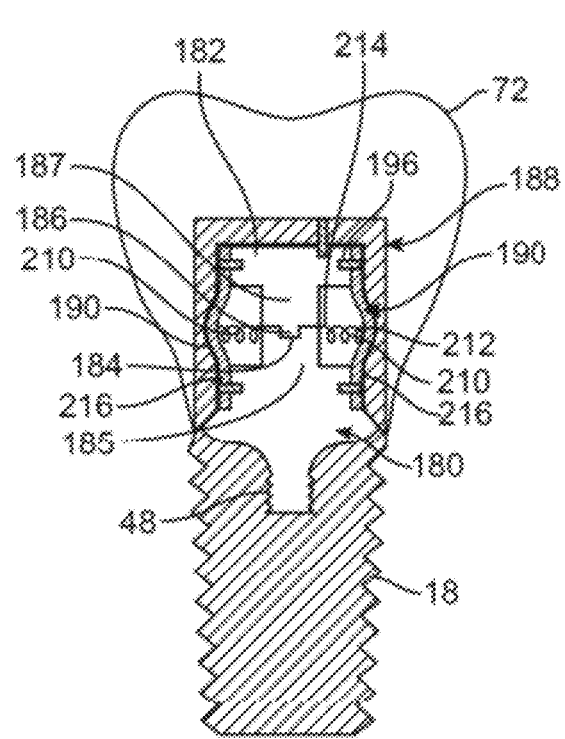
FIGS. 17A and 17B show cross-sectional side views of another variation of an abutment assembly utilizing a laterally-oriented spring design.
Figure 17B:
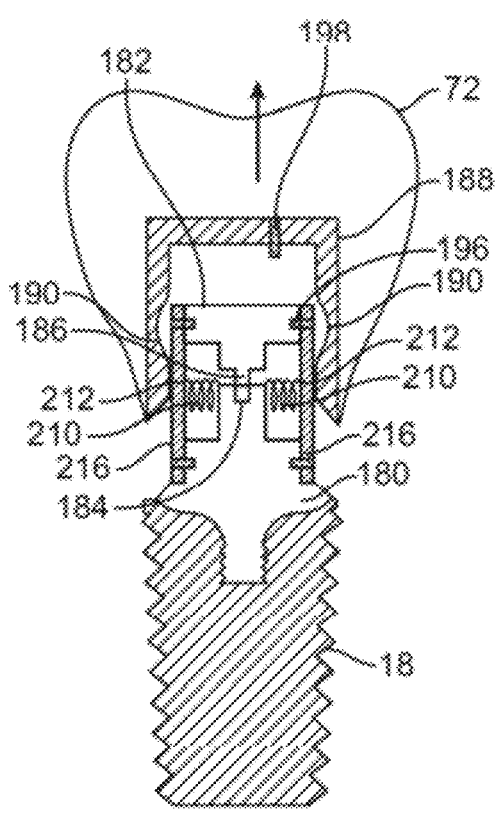

FIGS. 17A and 17B show cross-sectional side views of another variation of an abutment assembly utilizing a laterally-oriented spring design. The abutment assembly may be comprised of a lower and upper abutment 180, 182 as previously described with one or more shape memory elements or strips 216 secured to the abutment via pins 196. Each element or strip 216 may be predisposed to form a curved or arcuate portion 194 in its relaxed configuration which extends radially into securement against a curved receiving portion 190 defined along coping 188. Each element or strip 216 may be attached to a corresponding biasing element 210, e.g., spring, which extends laterally between an abutment attachment 214 along lower abutment shaft 185 and biasing element attachment 212 located along an inner surface of the arcuate portion 194 of element or strip 216. Biasing element 210 may be fabricated from any variety of materials, e.g. stainless steel, titanium, etc.

In its relaxed and un-actuated configuration, each of the biasing elements 210 may compress outwardly in a radial direction against each respective element or strip 216 to ensure securement of the arcuate portion 194 against the inner surface of coping 188. When heated or otherwise actuated, each of the elements or strips 216 may straighten to compress inwardly against each corresponding biasing element 210 to then allow for removal or adjustment of the coping 188 and crown 72 relative to the abutment assembly.

Figure 17C:
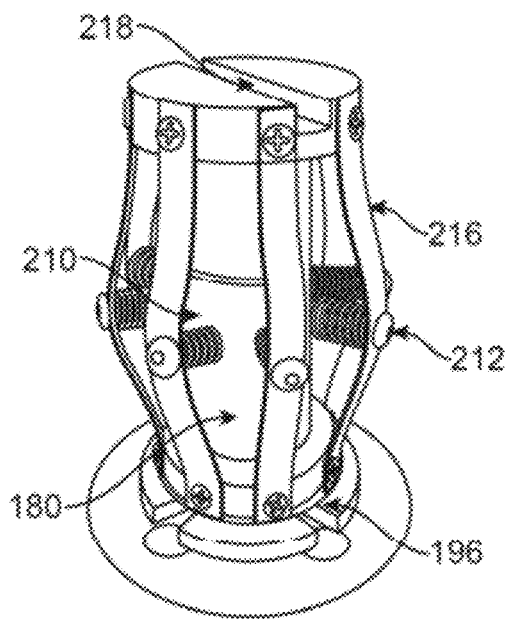
FIG. 17C shows a perspective view of an example of the laterally-oriented spring design.

FIG. 17C shows a perspective view of an example of the laterally-oriented spring design. As shown, each of the elements or strips 216 may be seen in their relaxed configuration with each respective biasing element 210 pushing radially outwardly against each respective strip 216. A slot or groove 218 may also be seen defined along an upper surface of the abutment assembly for securement with pin 198 protruding from coping 188 to ensure anti-rotation of the crown relative to the abutment assembly when secured.

FIGS. 18A and 18B show cross-sectional side views of another variation of an abutment assembly utilizing a post spring design. In this variation, a two-part lower and upper abutment 180, 182 assembly may utilize a biasing element 220, e.g., spring, longitudinally positioned to extend over both lower abutment shaft 185 and upper abutment shaft 187. As described above, biasing element 220 may be fabricated from a variety of materials, Biasing element 210 may be fabricated from any variety of materials, e.g. stainless steel, titanium, etc. Biasing element 220 may be attached to each respective abutment 180, 182 such that when the shape memory elements or strips 216 are in their cold or un-actuated configuration, the strips 216 may remain radially extended and secured to coping 188 and crown 72 and biasing element 220 may be biased to pull each abutment portion 180, 182 towards one another ensure the strips 216 remain in their radially extended configuration for securement within coping 188. However, when shape memory elements or strips 216 are actuated, they may straighten to allow for removal or adjustment of the crown 72 from the abutment assembly, as shown in FIG. 18B.

FIG. 18C shows a perspective view of the post spring abutment assembly illustrating each of the elements or strips 216 in their relaxed and radially extended configuration. As shown, biasing element 220 may be seen in extending in a tensioned state between lower and upper abutment 180, 182. Slot or groove 218 defined along an upper surface of upper abutment 182 may also be seen for locking against pin 198 extending from coping 188 to prevent or inhibit rotation between the abutment assembly and crown 72.

Figure 19A:
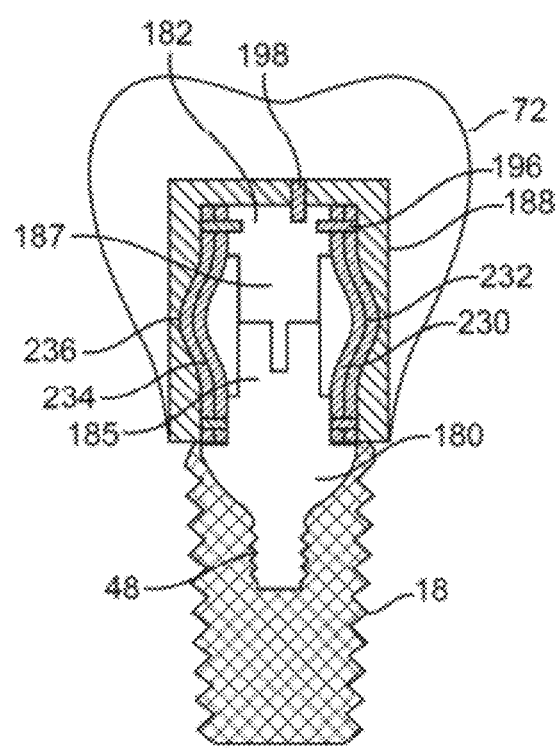
FIGS. 19A and 19B show cross-sectional side views of an abutment assembly utilizing a double-sleeve design.
Figure 19B:
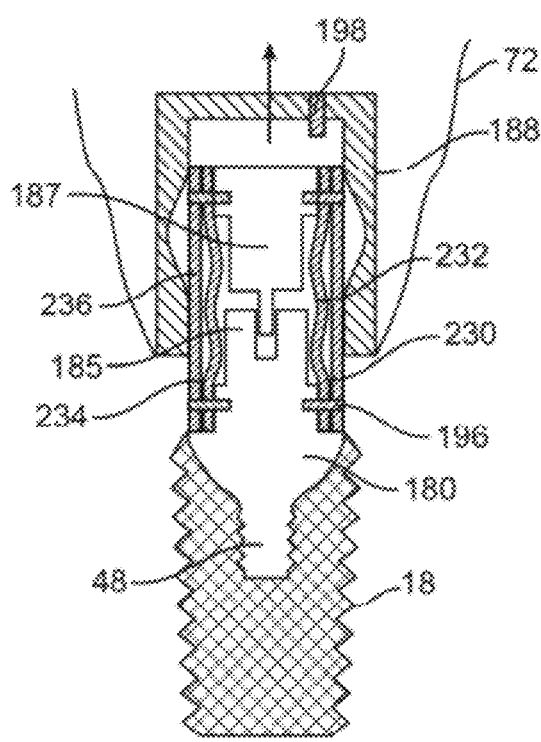

In yet another variation, the abutment assembly may optionally comprise an inner sleeve 230 and outer sleeve 234 extending between and coupled to lower and upper abutment 180, 182, as shown in the cross-sectional side views of FIGS. 19A and 19B. Inner sleeve 230 may be comprised of, e.g., a slotted sleeve made of plastic or metal such as stainless steel or shape memory material which functions as a biasing spring element. The inner sleeve 230 may be contained within and annularly positioned relative to outer sleeve 234 and both inner and outer sleeve 230, 234 may be secured to each lower and upper abutment 180, 182, respectively. Each longitudinal element or strip of inner sleeve 230 may define a radially curved or arcuate portion 232 which bows outwardly from the abutment assembly and outer sleeve 234 (positioned annularly relative to inner sleeve 230) may also define a curved or arcuate portion 236 which also bows outwardly in a manner corresponding to the curved or arcuate portion 232 of inner sleeve 230.

Figure 19C:
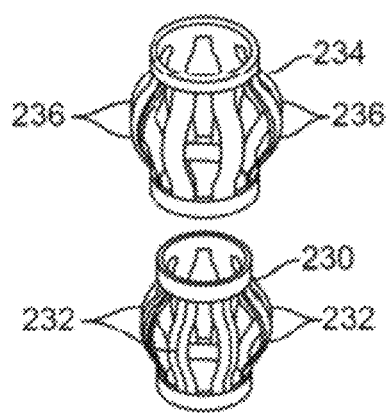
FIG. 19C shows a perspective view of an exploded assembly of the double-sleeve abutment assembly.
Figure 19C:
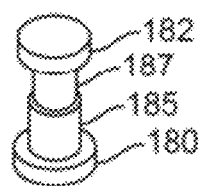
Figure 19C:
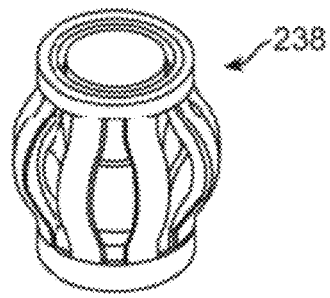

The curved or arcuate portion 232 of inner sleeve 230 may maintain a radially outward bias against the curved or arcuate portion 236 of outer sleeve 234, which may be comprised of a shape memory element, as described previously. With this constant radial force, outer sleeve 234 may remain locked against coping 188 and crown 72. When the assembly is actuated (e.g., heated), the curved or arcuate portion 236 of outer sleeve 234 may straighten and push inwardly against the curved or arcuate portion 232 of inner sleeve 230 to then allow for the removal or adjustment of crown 72 relative to the abutment assembly. FIG. 19C shows a perspective view of an exploded and assembled double-sleeve abutment assembly 238 illustrating the positioning of each feature. Although eight elements are illustrated extending between the collars of both inner and outer sleeves 230, 234 the number of elements may be adjusted for either or both sleeves 230, 234 to correspond with one another or they may number independently from one another.

Figure 20A:
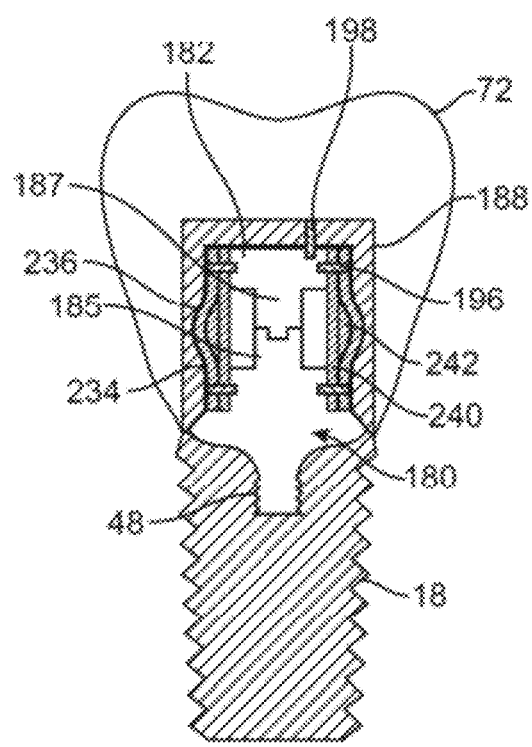
FIGS. 20A and 20B show cross-sectional side views of another variation similar to the double-sleeve design but utilizing an internal sleeve having a circumferential bump or protrusion.
Figure 20B:
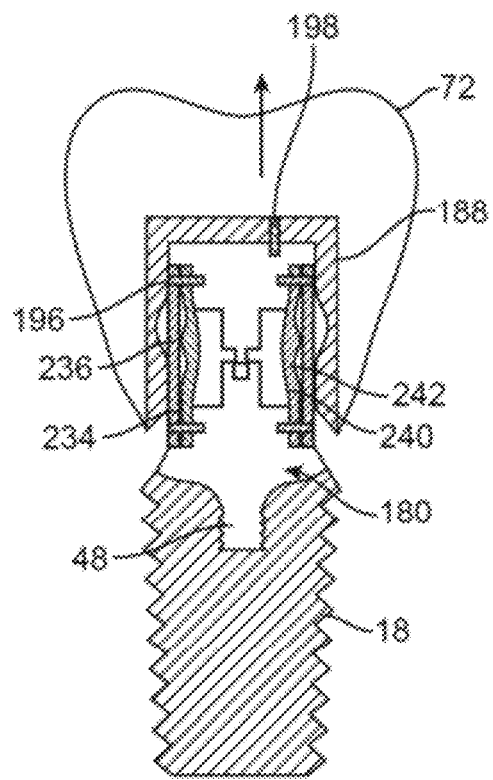
Figure 20C:
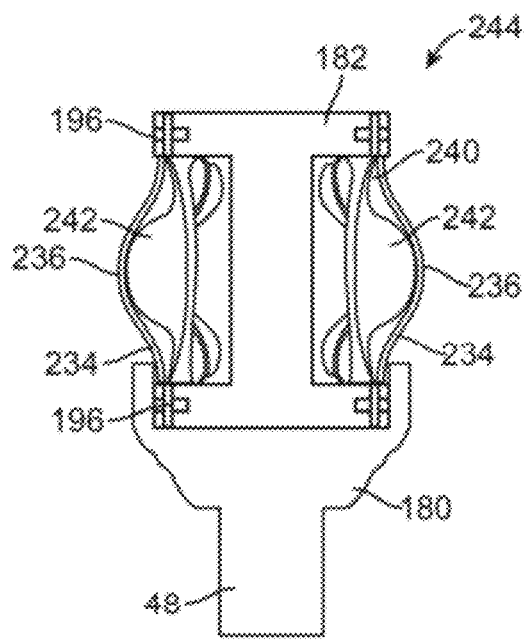
FIG. 20C shows a cross-sectional side view of another variation.

FIGS. 20A and 20B show cross-sectional side views of another variation similar to the double-sleeve design but utilizing an inner sleeve 240 having a circumferential bump or portion 242. As described above, one or more shape memory elements 234 may be secured to and extend with a curved or arcuate portion 236 between lower and upper abutment portions 180, 182. An inner sleeve 240 may be positioned annularly within the elements 234 and similarly secured to both lower and upper abutment portions 180, 182. The circumferential bump or portion 242 may protrude radially against the inner surface of the shape memory elements 234 and provide a biasing force which urges the shape memory elements 234 to maintain their curved configuration for securement against coping 188 and crown 72. When actuated, each of the shape memory elements 234 may straighten and push radially into each of the bumps or portions 242, as shown in FIG. 20B, to release the abutment from the coping 188 and allow for the removal or adjustment of crown 72. FIG. 20C shows another cross-sectional side view of the abutment assembly 244 illustrating the bumps or portions 242 contacted against each respective shape memory elements 234.

Figure 21A:
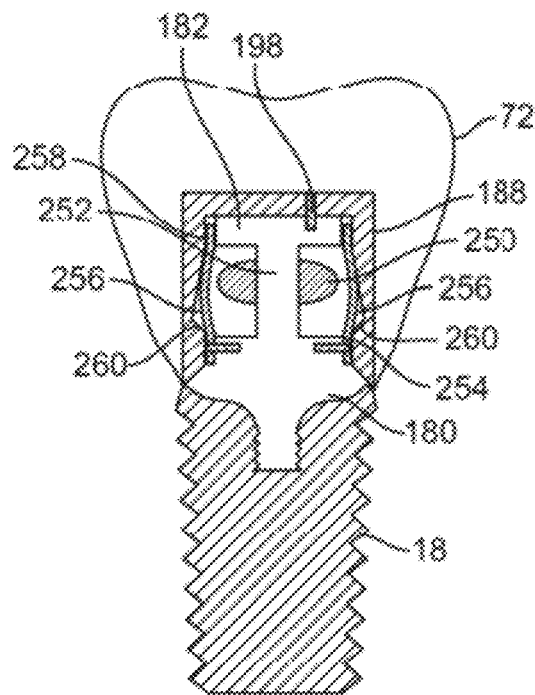
FIGS. 21A and 21B show cross-sectional side views of another variation of an abutment assembly having a polymeric spring or biasing element, such as polyurethane.
Figure 21B:
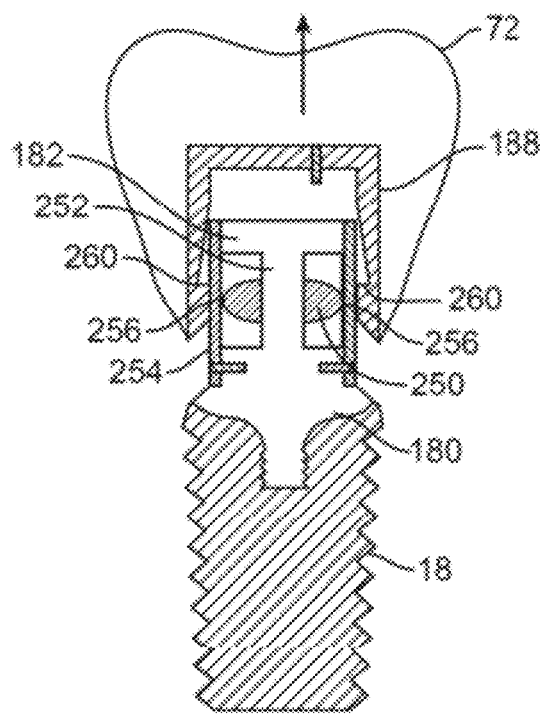

In yet another variation, FIGS. 21A and 21B show cross-sectional side views of another variation of an abutment assembly having a polymeric spring or biasing element 250 (such as a spring, rubber, or polyurethane, etc.) which provides for a radial biasing force between the abutment shaft 252 and circumferentially positioned shape memory sleeve 254 to secure the crown 72 to the abutment. In this variation, biasing element 250 may generally comprise a ring-shaped member which is securely positioned along the abutment shaft 252 such that an outer surface along a circumference of the biasing element 250 may press upon an inner surface of shape memory sleeve 254. In this variation, sleeve 254 may comprise a shape memory material which is formed in a tubular shape which is secured to both lower and upper abutment portions 180, 182 via one or more pins 196. Sleeve 254 may further define one or more slotted locking flaps 256 which curve radially outward from a corresponding flap pivot 258 positioned along an upper portion of the sleeve 254 away from the abutment shaft 252.

Sleeve 254 may be configured to have its locking flaps 256 remain in a radially extended configuration in its un-actuated state such that the flaps 256 may extend into contact against a corresponding securement edge 260 defined along an inner surface of coping 188 which prevents the removal or adjustment of crown 72 when engaged. Biasing element 250, due to its elasticity, may push outwardly against an inner surface of each flap 256 to ensure radial deflection and a locking engagement between the flap 256 and securement edge 260. When actuated, flaps 256 may straighten relative to the abutment shaft 252 while pushing against biasing element 250 to disengage from the securement edge 260 and thus allow for removal or adjustment of crown 72 from the abutment assembly, as shown in FIG. 21B.

Figure 21C:
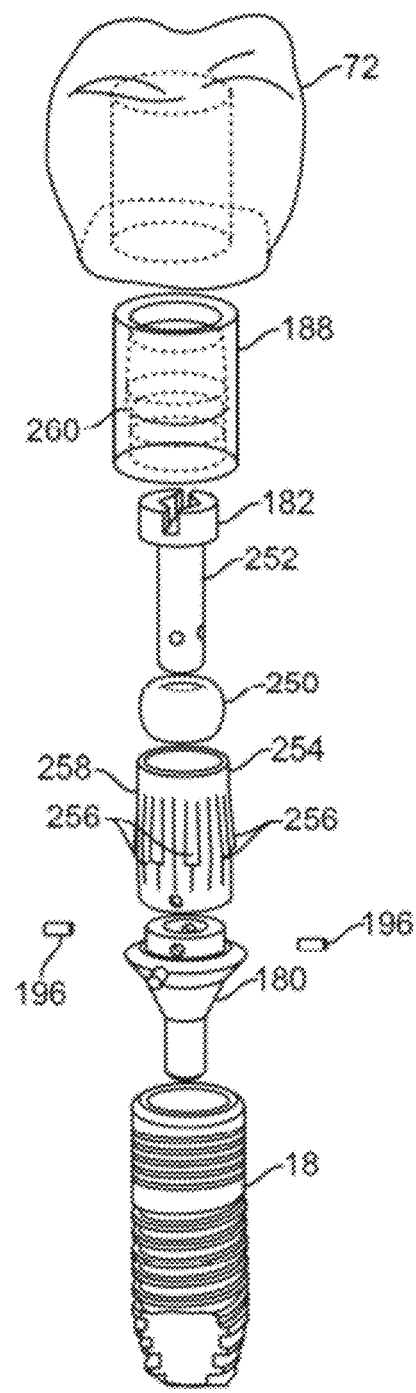
FIG. 21C shows a perspective view of an exploded assembly of the polymeric spring abutment assembly.

FIG. 21C shows a perspective view of an exploded assembly of the polymeric biasing element abutment assembly. As shown, each of the elements from crown 72 and coping 188 to the abutment shaft 252 and biasing element 250 for positioning within sleeve 254 may be seen. FIG. 22A shows a perspective view of the sleeve 254 secured upon the abutment shaft with the flaps 256 biased outwardly, in part, by the spring element. FIG. 22B shows a perspective view of the biasing element 250 positioned upon the abutment shaft 252 with the sleeve 254 removed for clarity and FIG. 22C shows a cross-sectional side view of the two-piece abutment and the biasing element 250 urging an inner surface of flaps 256 against the coping 188 and crown 72.

Figure 23:
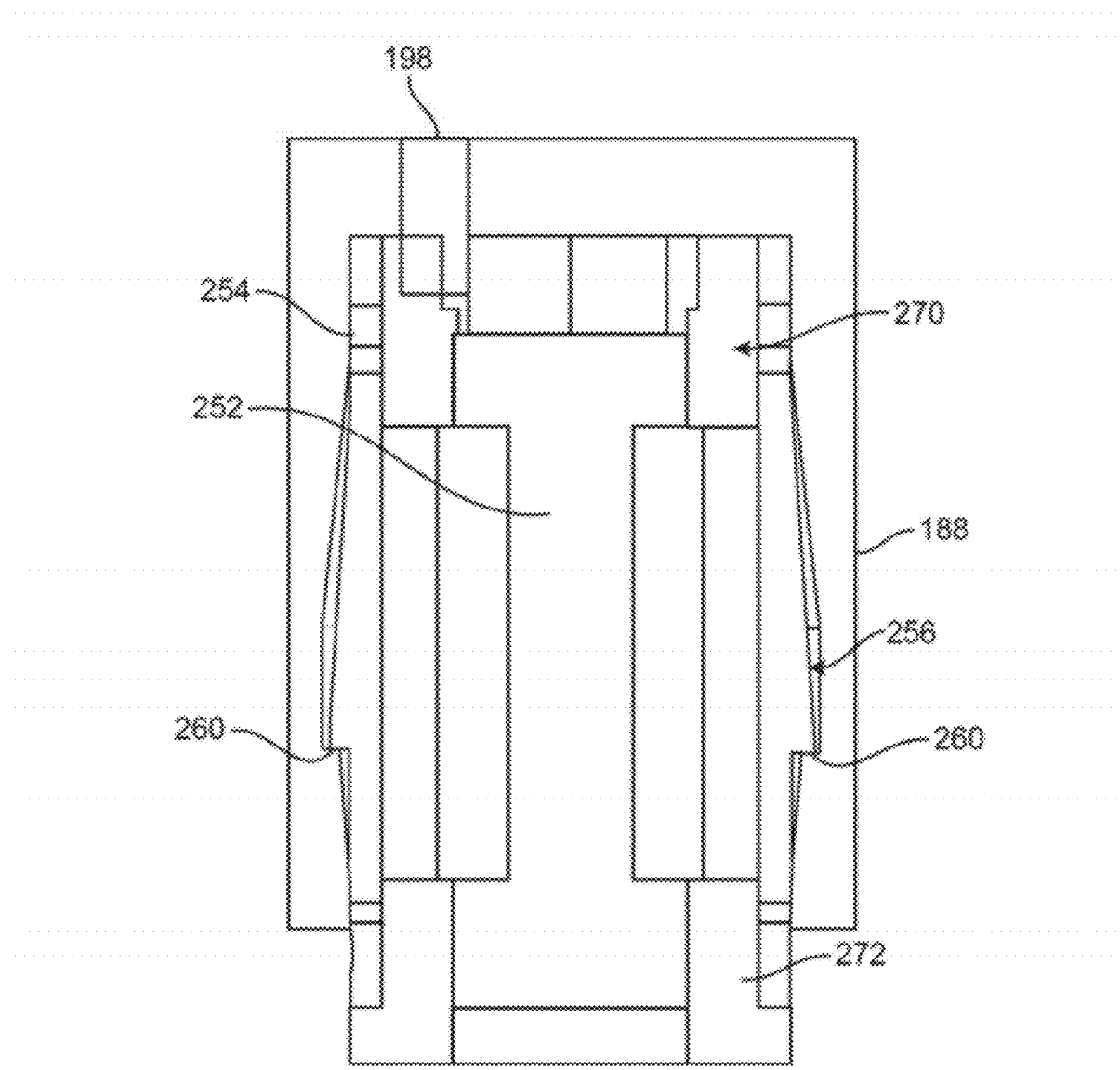
FIG. 23 shows a cross-sectional side view of another variation of the polymeric spring element utilizing an electrically insulating feature.

FIG. 23 shows a cross-sectional side view of another variation of the polymeric biasing element with the flaps 256 of sleeve 254 radially protruded and locked against securement edge 260 of coping 188. In this variation, one or more insulating rings or sleeves (e.g., made from a plastic) may be positioned between an outer surface of the abutment shaft 252 and an inner surface of sleeve 254 to provide for an electrically insulating feature between the two. This example illustrates a first insulating sleeve 270 and a second insulating sleeve 272 positioned between the abutment shaft 252 and sleeve 254 along an upper and lower portion of the sleeve 254. The features of one or more insulating sleeves may be optionally utilized with any of the designs disclosed herein.

Figure 24A:
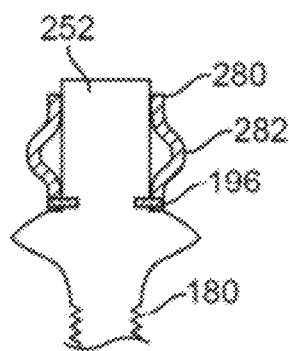
FIGS. 24A to 24C illustrate cross-sectional side views of another variation utilizing a sleeve which is set to reduce in diameter when chilled.
Figure 24B:
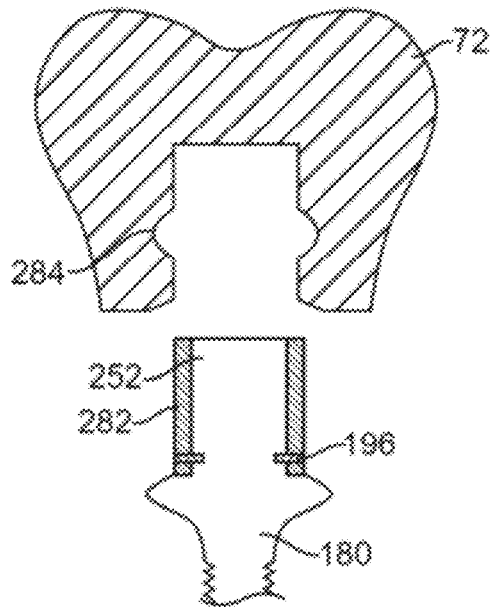
Figure 24C:
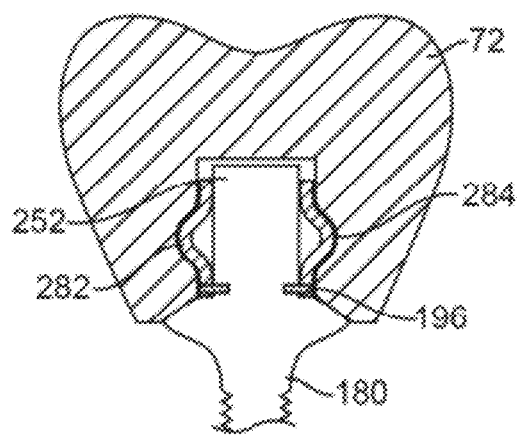

In yet another variation, FIGS. 24A to 24C illustrate cross-sectional side views of a shape memory sleeve 280 which defines an arcuate or curved portion 282 for securement within a corresponding receiving portion 284 defined within a coping or within crown 72. In this example, sleeve 280 may be configured to reduce in diameter when chilled instead of when heated. Shape memory sleeve 280 may thus be heat treated and shaped with curved portions 282 such that sleeve 280 bulges when at a normal body temperature. Sleeve 280 may be first chilled between an activation temperature to soften the sleeve 280, which may then be crimped to a straightened cylindrical shape to allow for placement of crown 72, as shown in FIG. 24B. When sleeve 280 reaches body temperature, it may reconfigure into its curved configuration and lock securely against the crown 72, as shown in FIG. 24C. To remove or adjust crown 72, the sleeve 280 (and/or crown 72) may be chilled below its activation temperature to soften the material and thus allow for relative movement between sleeve 280 and crown 72.

Figure 25A:
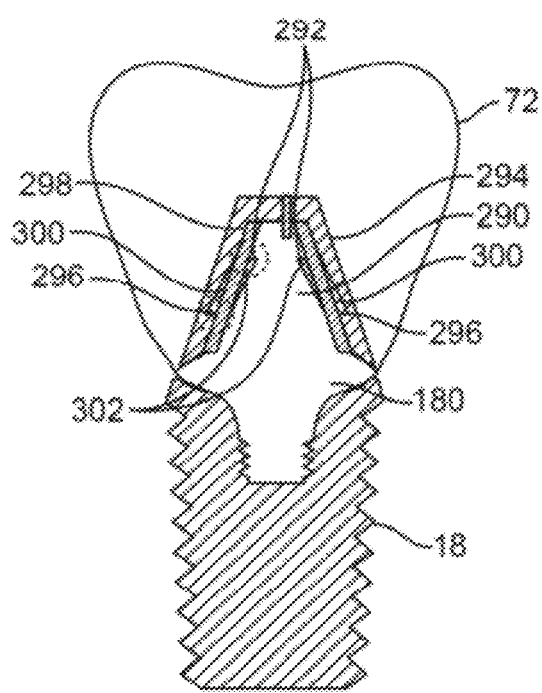
FIGS. 25A and 25B show cross-sectional side views of a variation of the abutment assembly having a self-locking sleeve design.
Figure 25B:
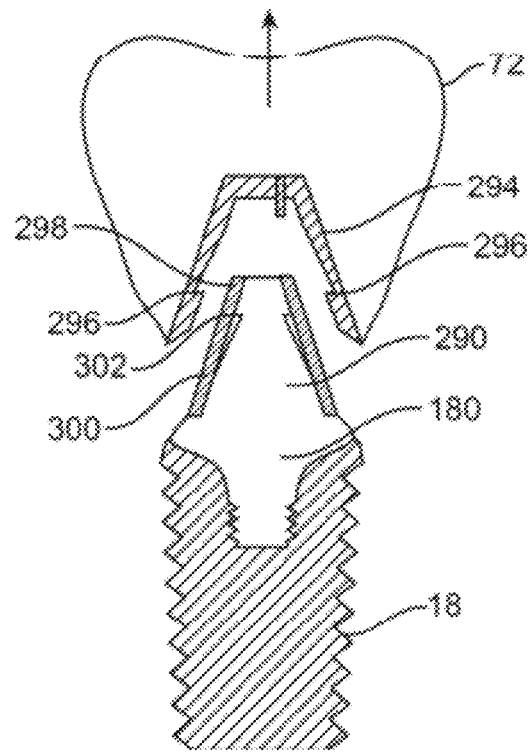
Figure 25C:
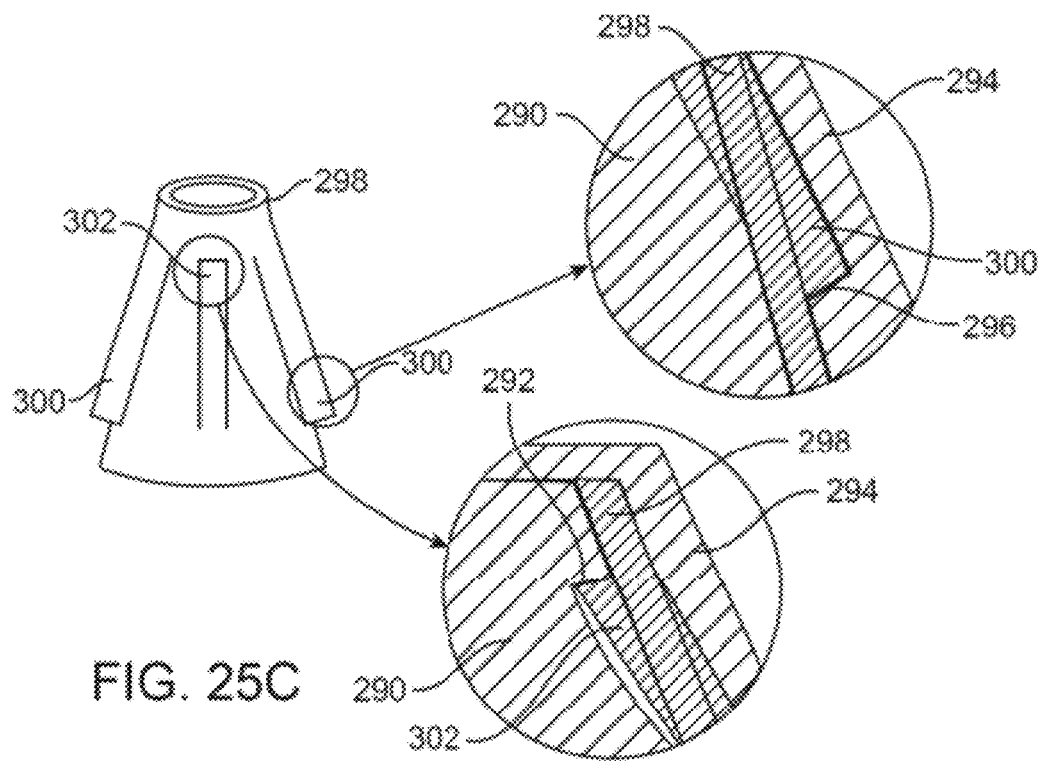
FIG. 25C shows a perspective view of the self-locking sleeve and detail cross-sectional side views of the sleeve relative to the coping and abutment.

In yet another variation, a shape memory shape memory sleeve 298 may be formed and shaped, e.g., with a mandrel, to form a tapered configuration which may be secured to an abutment shaft 290 tapered in a corresponding manner. As shown FIGS. 25A and 25B, which illustrate cross-sectional side views of an abutment assembly having the tapered design, the tapered sleeve 298 may be slotted to form several locking flaps which protrude from the tapered sleeve 298 in an alternating manner to form a self-locking sleeve design. In this example, at least one or more locking flaps 300 may protrude radially from sleeve 298 such that the flaps 300 extend radially from a lower portion of the sleeve 298 where the diameter of the sleeve 298 is relatively larger. At least one or more additional locking flaps 302 may extend radially from an upper portion of sleeve 298 where the diameter of the sleeve 298 is relatively smaller. The radially extending portions of each flap 300, 302 may be configured in an alternative pattern, as shown in the perspective view of FIG. 25C, although other configurations may be accomplished. Accordingly, coping 294 which may be tapered in a corresponding manner may be secured upon the tapered sleeve 298 in a self-locking manner where locking flaps 300 projecting radially from a lower portion may lock to tapered coping 294 via locking under cut 296 and locking flaps 302 projecting radially from an upper portion may lock to tapered abutment 290 via locking under cut 292.

Tapered sleeve 298 may be heat treated to retain its shape memory condition with all flaps 300, 302 collapsed. Flaps 300, 302 may be extended manually after heat treatment prior to placement of tapered sleeve 298 onto tapered abutment 290. With sleeve 298 locked upon tapered abutment 290 via flaps 292 extended inwardly, crown 72 and coping 294 may be positioned upon sleeve 298 and locked via flaps 300 extended outwardly. To remove or adjust crown 72 from the abutment assembly, the flaps 300 may be actuated to release from undercut 296 defined along coping 294. Because sleeve 298 is self-locking to tapered abutment 290, retaining pins may be optionally used or omitted entirely from the assembly for securing sleeve 298 to abutment 290.

Figure 26A:
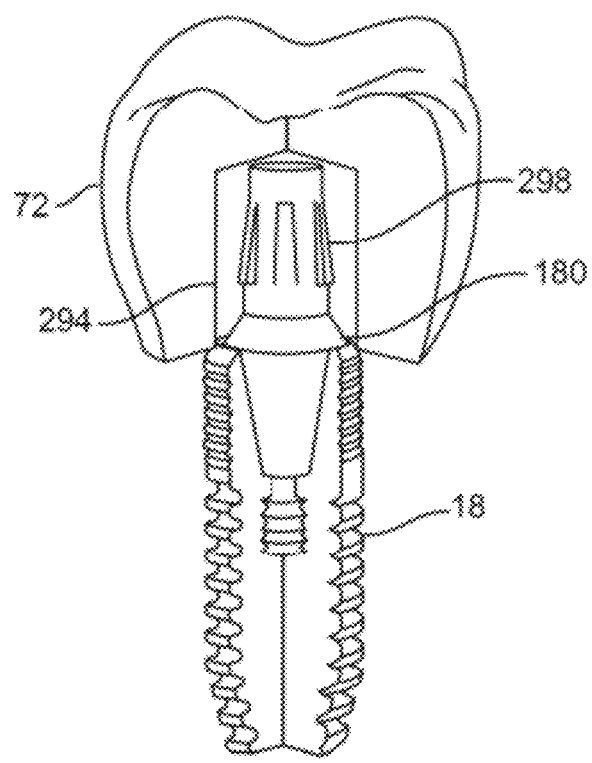
FIGS. 26A and 26B show perspective views illustrating the crown secured upon the self-locking sleeve and details of the anti-rotation mechanism.
Figure 26B:
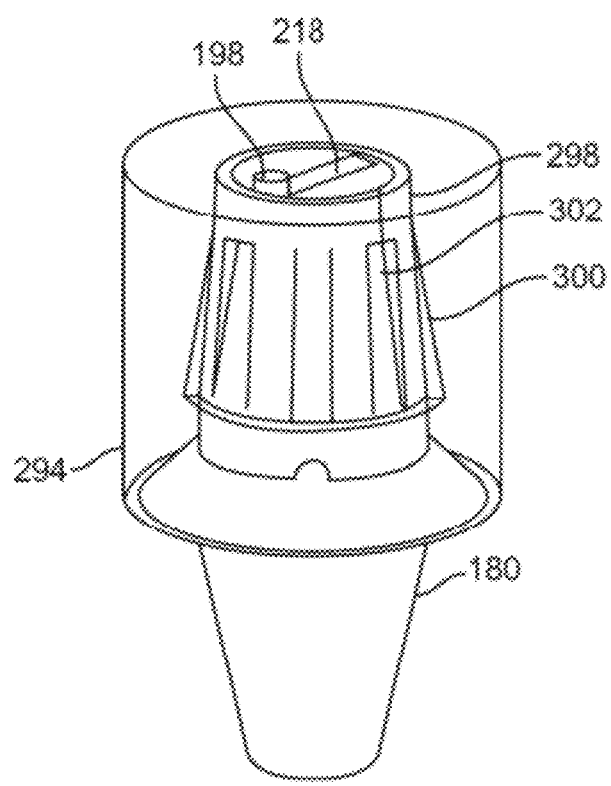

FIGS. 26A and 26B show perspective views illustrating the crown 72 secured upon the self-locking sleeve 298 and details of the pin 198 engaged within anti-rotation slot 218. FIGS. 27A to 27C illustrate an example for forming and positioning the self-locking sleeve 298 upon tapered abutment 290. As illustrated, an initial shape memory sleeve 298' may be formed initially to have multiple flaps extending in alternating directions. The sleeve 298' may further have gap portions 304 formed, e.g., at four locations, spaced from one another along a first end of sleeve 298' which is to be reduced in diameter to create the tapered shape. The portions of sleeve 298' between gap portions 304 may be approximated to reduce the overall diameter by shape memory sleeve 298'' after forming. Each of the individual flaps 300, 302 may then be reconfigured to protrude radially from the surface of sleeve 298 to form the self-locking features. With the sleeve 298 formed, it may then be positioned upon the tapered abutment 290 and secured, as described above. With sleeve 298 secured, crown 72 may then be positioned over the abutment and secured sleeve 298 to lock the crown 72 accordingly.

Figure 27D:
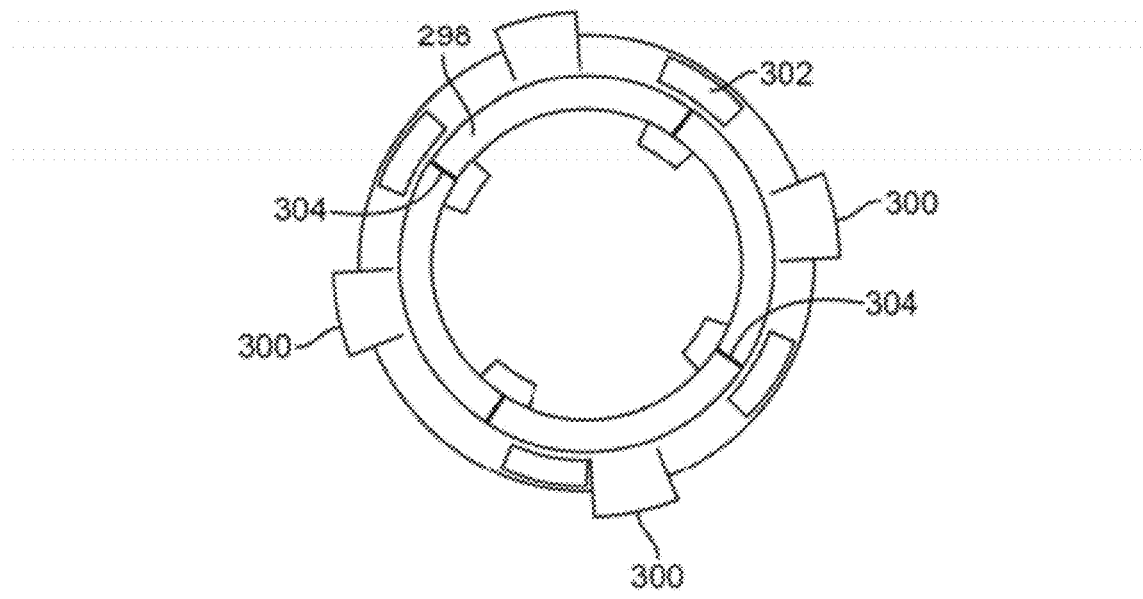
FIGS. 27D and 27E show top and perspective views of the self-locking sleeve flaps.
Figure 27E:
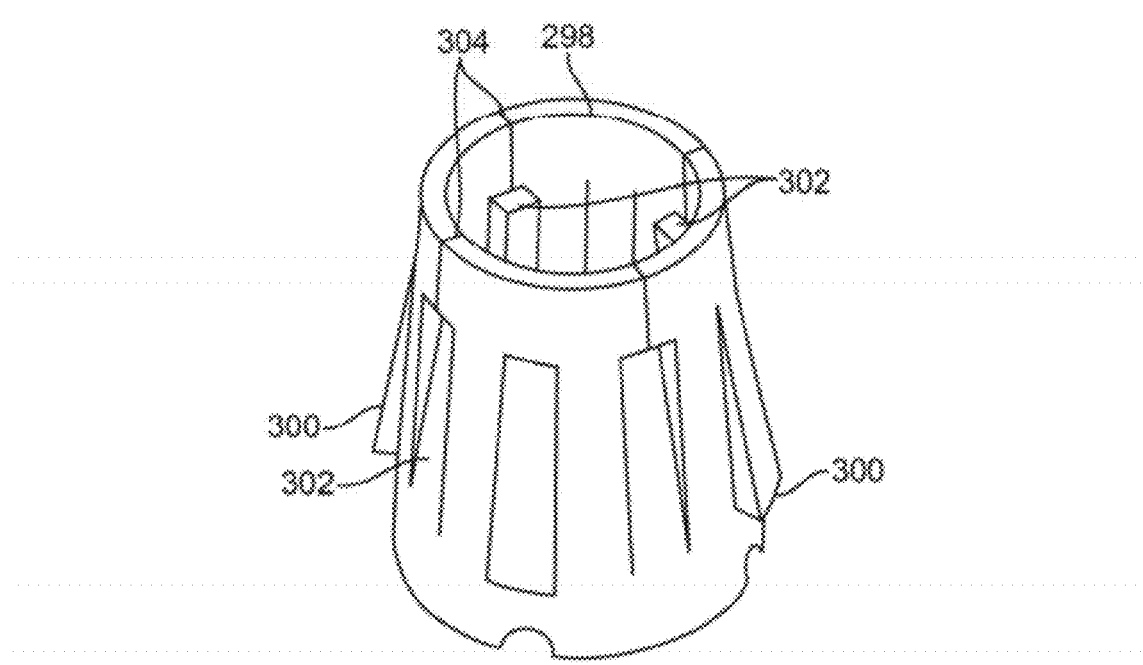

FIGS. 27D and 27E show top and perspective views of the tapered self-locking sleeve 298 and the alternating flaps 300, 302 extending both inwardly and outwardly. As illustrated, although four flaps 302 are shown to extend inwardly and four alternating flaps 300 are shown to extend outwardly, the number of flaps 300, 302 may be varied and the positioning of the flaps relative to one another may also be varied depending upon the desired locking results.

Figure 28A:
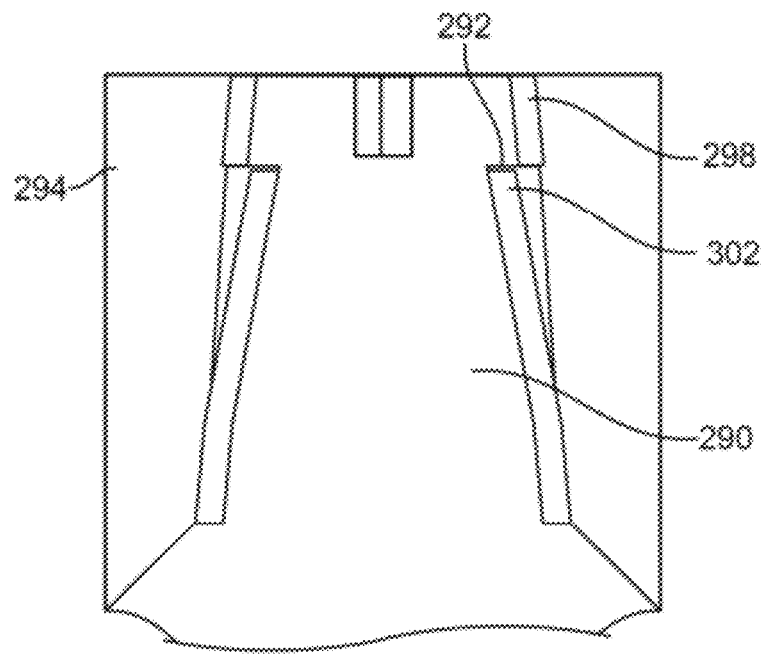
FIGS. 28A and 28B show cross-sectional side views of the self-locking sleeve secured upon the abutment and secured to the crown as well.
Figure 28B:
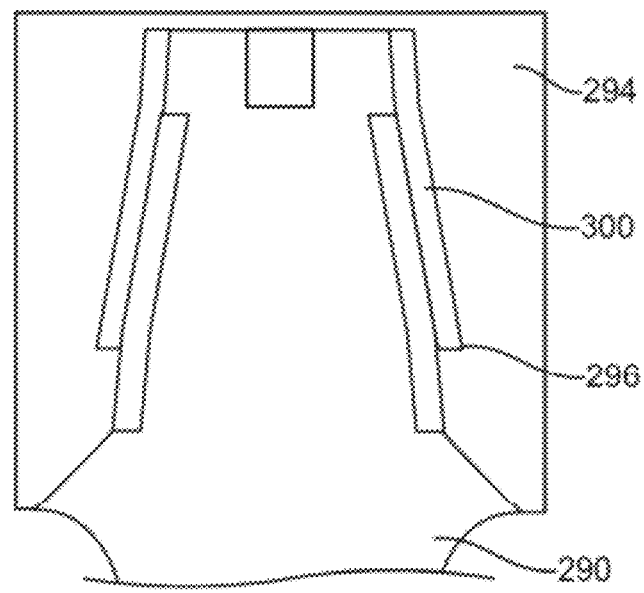

FIGS. 28A and 28B show cross-sectional side views of the self-locking sleeve 298 secured upon the abutment 290 and secured to the coping 294 as well. The side view of FIG. 28A illustrates an example of how inwardly projecting flaps 302 may lock upon the abutment shaft 290 while FIG. 28B illustrates another cross-sectional view of how the outwardly projecting flaps 300 may lock to the coping 294.

Figure 29A:
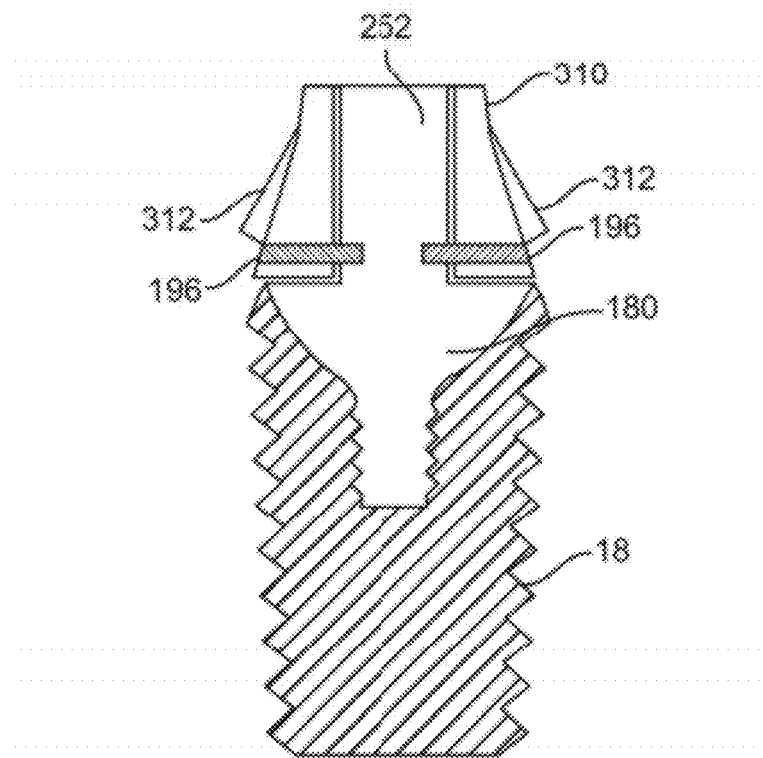
FIGS. 29A and 29B show cross-sectional side and perspective views of another variation of an abutment assembly having a taper cut sleeve feature.
Figure 29B:
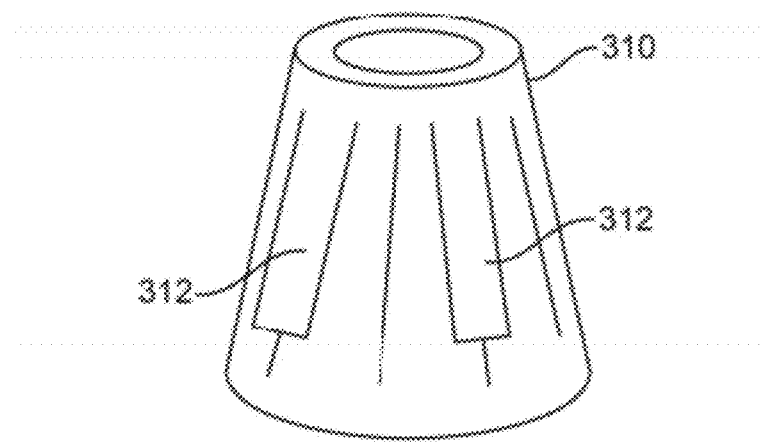

FIGS. 29A and 29B show cross-sectional side and perspective views of another variation of an abutment assembly having a taper cut sleeve feature. In this variation, the abutment shaft 252 itself may be comprised of a straight member rather than a tapered member, as described above. The shape memory sleeve 310 may itself be tapered with one or more locking flaps 312 extending radially outward to lock against the coping and/or crown 72. The shape memory sleeve 310 may be tapered by grinding a sleeve having an initial cylindrical shape down to a tapered configuration with the flaps 312 defined along a longitudinal direction. Accordingly, a lower portion of the sleeve 310 may have a thickness which is larger relative to a thickness of an upper portion of the sleeve 310, as shown in FIG. 29A. Sleeve 310 may be affixed to abutment shaft 252 via one or more pins 196, as previously described.

Figure 30A:
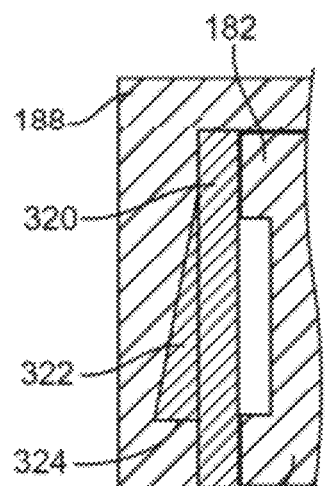
FIG. 30A shows a cross-sectional side view of a variation of a sleeve locking mechanism having a sleeve with flaps for securement to the coping.
Figure 30B:
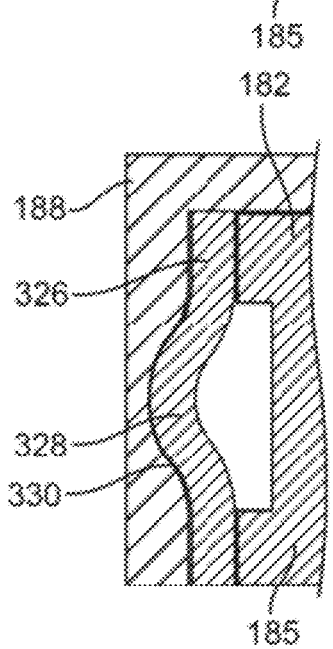
FIG. 30B shows a cross-sectional side view of another variation of a sleeve having a curved portion for securement to the coping.
Figure 30C:
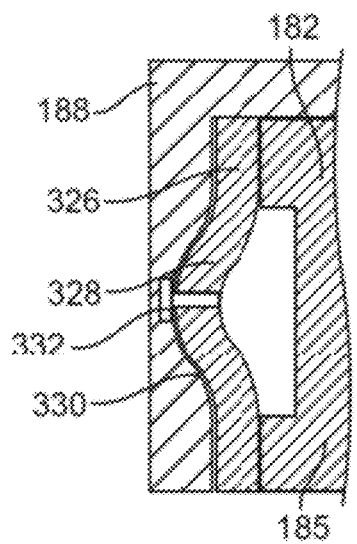
FIG. 30C shows a cross-sectional side view of another variation of a sleeve having a curved portion which may be pinned for securement to the coping.

As described above, FIG. 30A illustrates a cross-sectional side view of one variation of a shape memory sleeve 320 locking mechanism having a sleeve with locking flap 322 for securement via locking undercut 324 to the coping 188. FIG. 30B shows a cross-sectional side view of another variation of a shape memory sleeve 326 having a curved or arcuate portion 328 for securement to the coping. FIG. 30C shows a cross-sectional side view of another variation of a curved or arcuate portion 328 having a curved or arcuate receiving section 330 which may be pinned via pin 332 for securement to a curved or arcuate portion 328. These and any of the locking mechanisms and configurations described herein may be combined between any of the variations, as practicable.

Figure 31A:
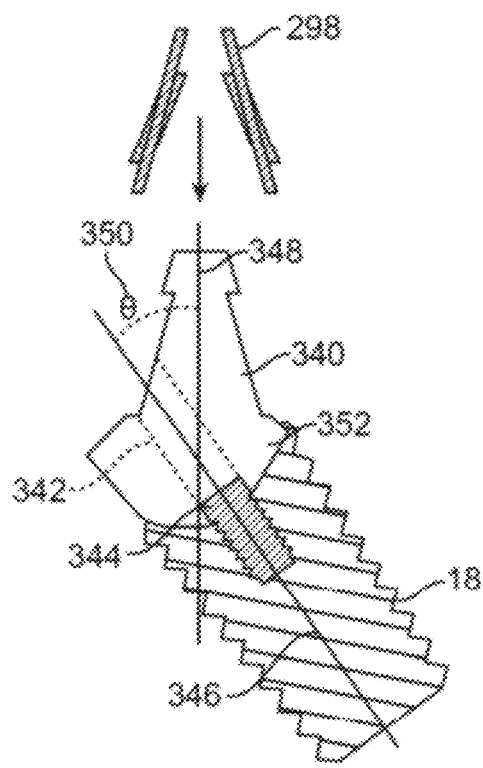
FIGS. 31A and 31B show cross-sectional side views of another example of a sleeve which may be positioned upon an angled abutment assembly.
Figure 31B:
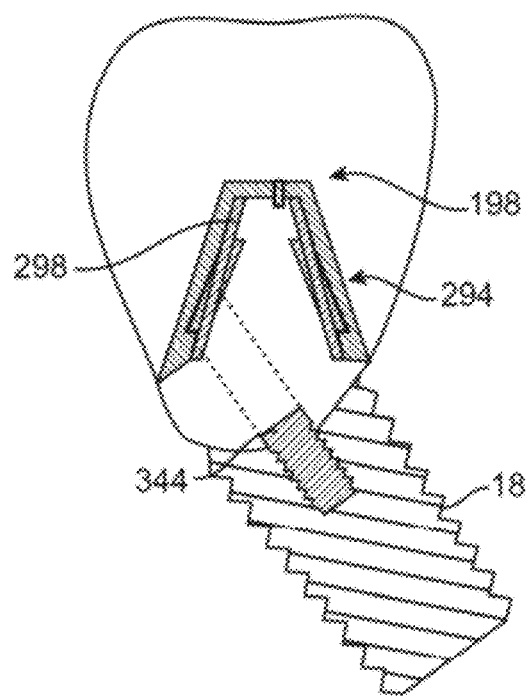

FIGS. 31A and 31B show cross-sectional side views of yet another example of a shape memory sleeve 298 which may be positioned upon an angled abutment assembly to position the sleeve 298 and crown 72 at an angle relative to the implant 18 portion. As mentioned, although the shape memory sleeve 298 is illustrated and described as the self-locking sleeve 298 variation, this is shown for illustrative purposes and any of the other shape memory sleeves 298 or elements or strips described herein may be utilized with this angled abutment assembly, as so desired.

Figure 31C:
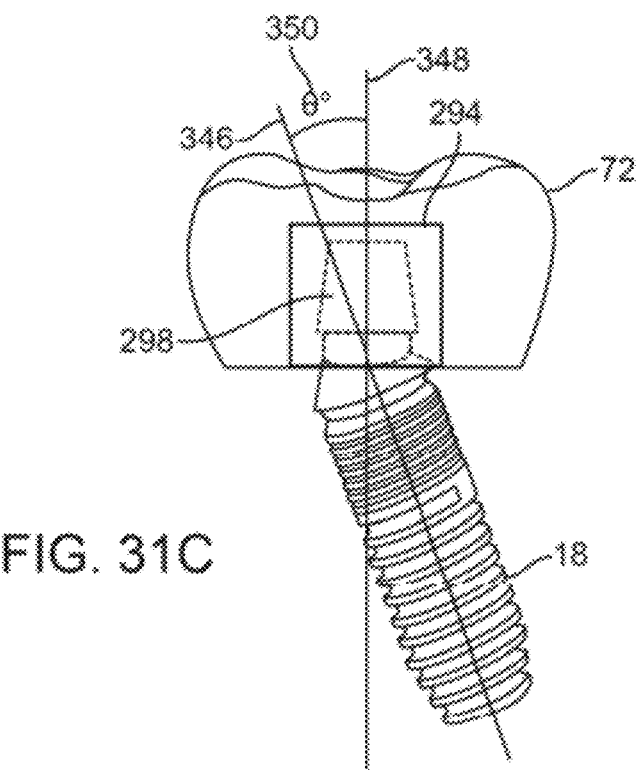
FIG. 31C shows a side view of a crown secured upon an angled abutment assembly positioned at a pre-set angle.

In this variation, angled abutment 340 may generally comprise an abutment interface 352 which is secured into contact against the implant 18 via retaining screw 344 which may be inserted through channel 342 defined within abutment 340. A lower portion of the abutment adjacent to abutment interface 352 may be aligned, e.g., in parallel with a longitudinal axis of implant 18 to define an implant longitudinal axis 346. An upper portion of abutment 340 may thus form a portion which is angled relative to abutment interface 352 such that abutment 340 defines an abutment longitudinal axis 348 which forms an angle 350, e.g., Θ. The upper portion of angled abutment 340 may thus be configured with an angle which may vary through a range, Θ, depending upon the desired angle of the crown 72 relative to the implant 18, as shown in FIG. 31B. FIG. 31C shows a side view of a crown secured upon an angled abutment assembly positioned at a pre-set angle 350, Θ.

FIGS. 32A to 32D illustrate an example of a how an angled abutment assembly may be secured. As shown in FIG. 32A, angled abutment 340 may be positioned within implant 18 and once desirably positioned relative to implant 18, retaining screw 344 may be inserted through channel 342 and tightened to implant 18 thus securing abutment 340 to implant 18, as shown in FIGS. 32B and 32C. The shape memory sleeve 298 may then be secured to the angled abutment 340, as shown in FIG. 32D, to further secure a crown upon the sleeve 298 such that the crown is angled relative to the implant 18.

Figure 33:
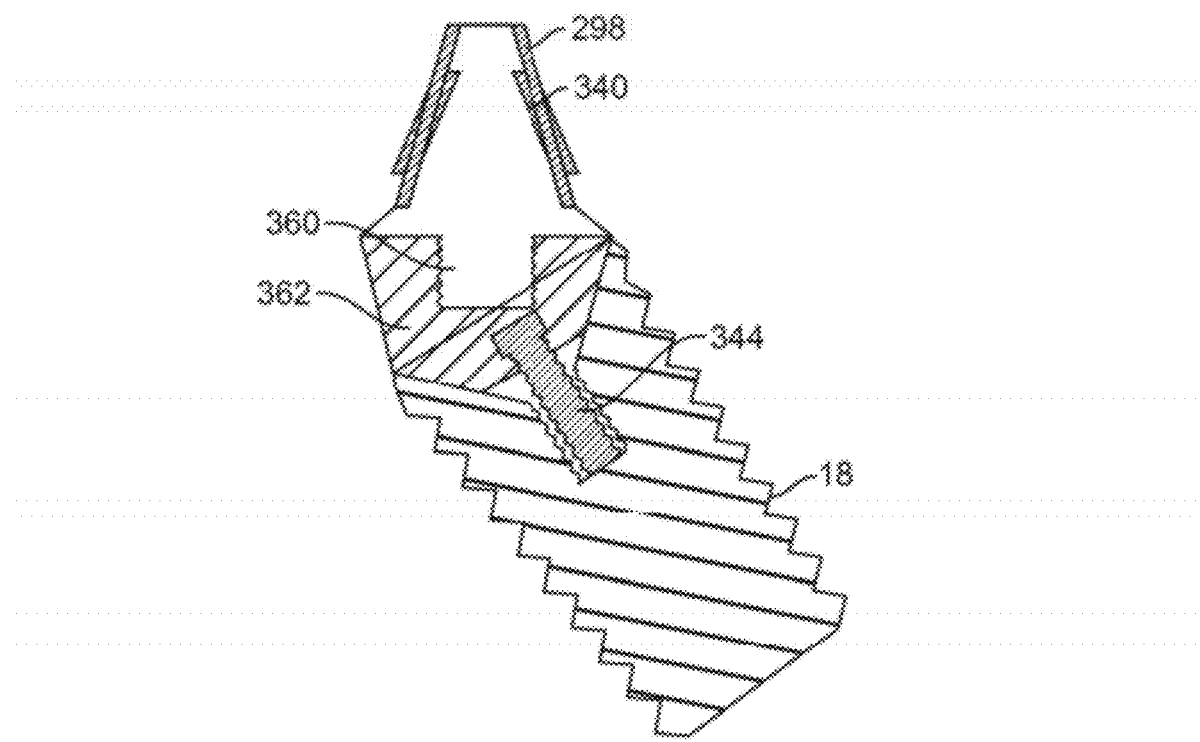
FIG. 33 shows a cross-sectional side view of another variation of an angled abutment assembly having an abutment shim.

FIG. 33 shows a cross-sectional side view of another variation of an angled abutment assembly having an abutment shim. As previously described, an upper portion of angled abutment 340 may be secured to implant 18 such that sleeve 298 is angled relative to the implant 18. In this variation, the abutment assembly may be formed of a two-part assembly having the upper portion 340 which may be secured to a separate lower angled abutment shim 362. While the upper portion 340 may be comprised of an abutment which is non-angled, angled abutment shim 362 may form an interface which is secured to implant 18 via retaining screw 344 and an interface for securement to upper portion 340 which may be formed to have any number of angles. Accordingly, different shims of differing angles may be secured between implant 18 and upper portion 340 to accommodate various orientations of the crown relative to the implant 18 (which may have already be implanted in the patient) depending upon the desired results.

Figure 34A:
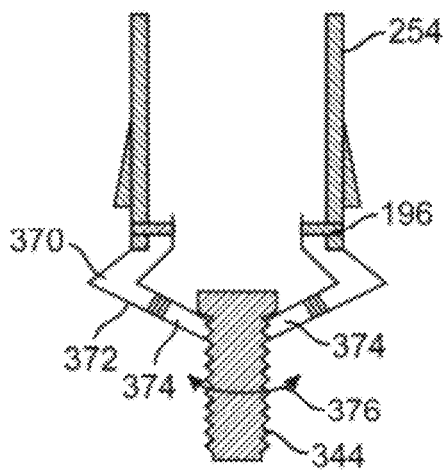
FIG. 34A to 34C show partial cross-sectional side and top views of an abutment assembly having a rounded abutment which allows for adjustability.
Figure 34B:
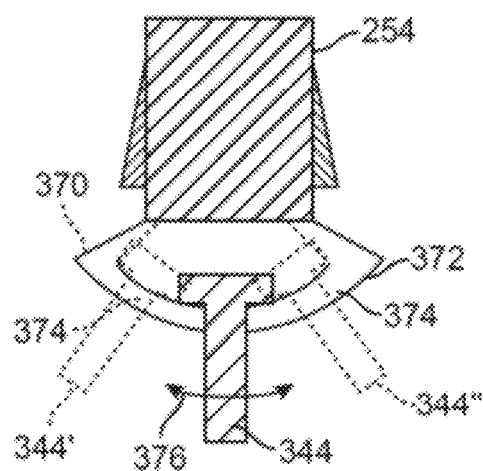
Figure 34C:
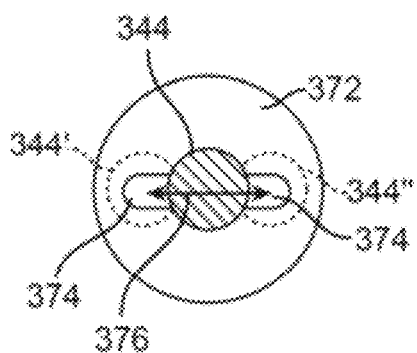

FIG. 34A to 34C show partial cross-sectional side and top views of another variation of an abutment assembly having a rounded abutment which allows for adjustability over a range of angles once an implant 18 has already been implanted into the patient. As shown, sleeve 254 may be secured to a rounded abutment 370 having a rounded abutment interface 372 which defines a guide slot 374 through which retaining screw 344 may be positioned for securement to the implant 18. Implant 18 may also form an implant socket interface 378 which interfaces with rounded abutment interface 372, e.g., like a ball-socket interface.

Figure 34D:
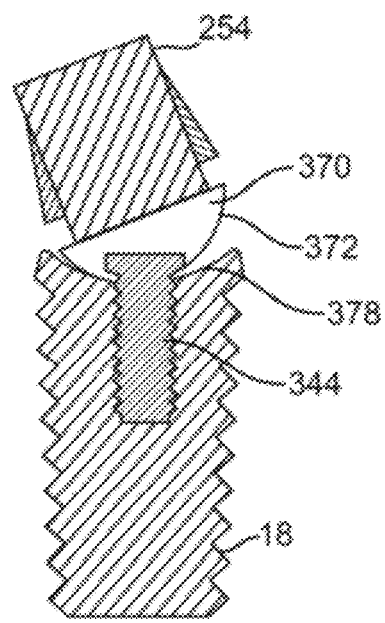
FIG. 34D shows a cross-sectional side view of an assembled abutment assembly having the rounded abutment.

Guide slot 374 may form a singular slot or multiple directional slots which allows rounded abutment 370 to be directionally guided relative to retaining screw 344 and implant 18, as indicated by direction of movement 376. Thus, once rounded abutment 370 and sleeve 254 has been desirably positioned and angled relative to implant 18, as indicated by the alternative positioning of retaining screw 344' and 344'' relative to rounded abutment 370 (as shown in FIGS. 34B and 34C), retaining screw 344 may be secured to lock rounded abutment 370 to implant 18 (as shown in FIG. 34D). If readjustment is desired, screw 344 may be un-tightened to release rounded abutment 370 to be readjusted relative to implant 18 after which screw 344 may then be re-tightened.

Although particular shape memory sleeves are illustrated with the angled abutment variations, this is intended for illustrative purposes and is not intended to be limiting. Accordingly, any of the variations of sleeves or strips or elements may be used in combination with any of the angled abutment designs as shown and described herein.

Figure 35A:
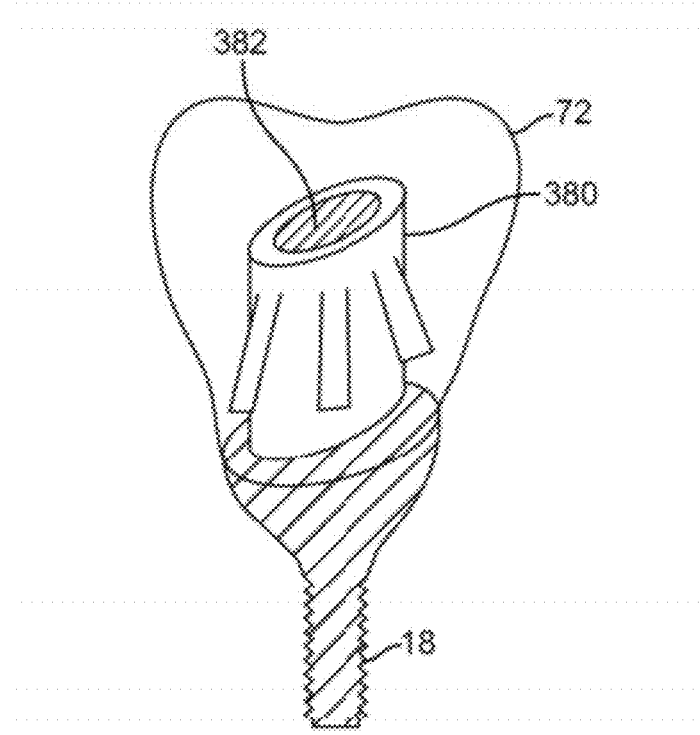
FIGS. 35A and 35B show partial cross-sectional side and top views of another variation of a sleeve having a non-circular shape, e.g., elliptical, for preventing rotation.
Figure 35B:
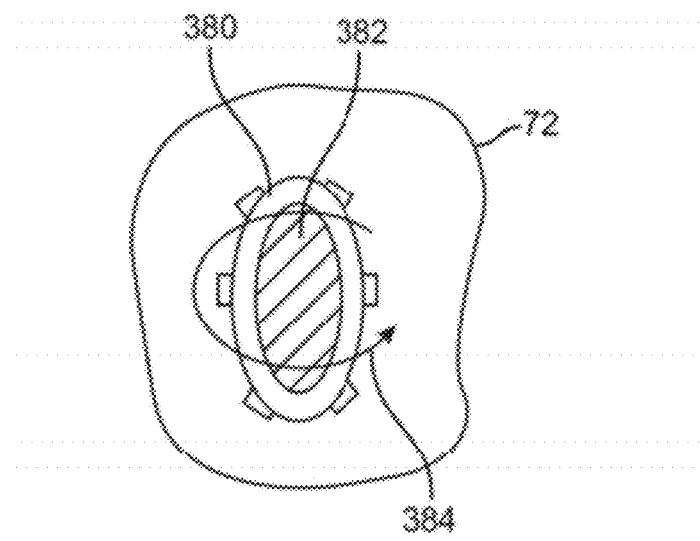

In yet another variation which may be utilized with any of the abutment designs described herein, FIGS. 35A and 35B show partial cross-sectional side and top views of a shape memory sleeve 380 having a non-circular cross-sectional circumference, e.g., elliptical, for preventing rotation of the crown 72 relative to the implant 18. As shown, the non-circular sleeve 380 may be secured to a correspondingly non-circular abutment shaft 382. Because of the keyed nature of the securement between sleeve 380 and shaft 382 (and the resulting coping within crown 72), crown 72 may thus be inhibited from rotating relative to the implant 18, as indicated by the inhibited direction of rotation 384. Although illustrated with an elliptical cross-sectional shape, any number of non-circular shapes may be utilized with abutment shaft 382 and sleeve 380, e.g., triangular, rectangular, etc. Alternatively, projections which protrude from sleeve 380 and/or shaft 382 which act as keyed guides may be used instead or in addition.

FIG. 36A shows a cross-sectional side view of another example of a feature which may be utilized with any of the abutment designs described herein. In this example, a seal 390 may be utilized between the abutment interface 392 and coping 294. Seal 390, as shown the top view of FIG. 36B, may be formed to have any variety of configurations to conform to the abutment and/or coping. FIGS. 36C and 36D show partial cross-sectional perspective and detail views of an example of seal 390 interspaced between the abutment-coping interface. Moreover, seal 390 may be fabricated from any number of biocompatible materials, e.g., silicon, polyurethane, etc.

In yet another example of an alternative abutment assembly, FIGS. 37A and 37B show examples of a shape memory abutment 400 which may comprise an assembly having two or more split securement members 402. Shape memory abutment 400 may be heat-treated with the split securement members 402 extended. When assembled, abutment 400 may be chilled to its shape memory condition and split securement members 402 may crimped together (as indicated by the direction of crimping 406) and inserted into the threaded receiving channel 410 of implant 18, as shown in FIG. 38A. As the temperature of abutment 400 rises, the split securement members 402 may expand (as indicated by the direction of release 408) and lock with the internal thread of the implant 18, as shown in FIG. 38B.

In an alternative of the split securement members 402, the members may be fabricated from a plastic or non-shape memory material but instead have a shape memory band 404 wrapped or otherwise secured over the members 402. In this manner, the shape memory band 404 may be activated to close the members 402 relative to one another, as shown in FIG. 37B.

FIGS. 39A and 39B illustrate partial cross-sectional side views of another example of how a split abutment may be positioned at an angle within an implant fixture. When positioning the split securement members 402 within receiving channel 410, abutment 400 may be maintained at an angle relative to implant 18 when members 402 are in their low-profile configuration. When members 402 are reconfigured into secure contact within channel 410, abutment 400 may be secured at an angle relative to implant 18 for subsequently positioning the crown at the angle.

Figure 40A:
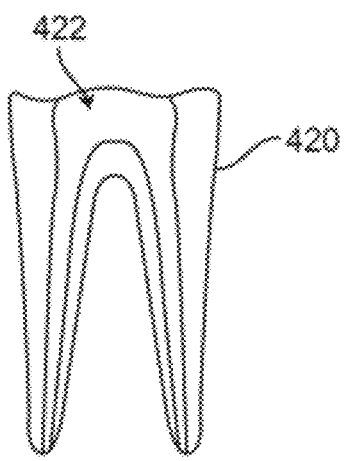
FIG. 40A shows a cross-sectional side view of a pre-existing root with the pulp removed.
Figure 40B:
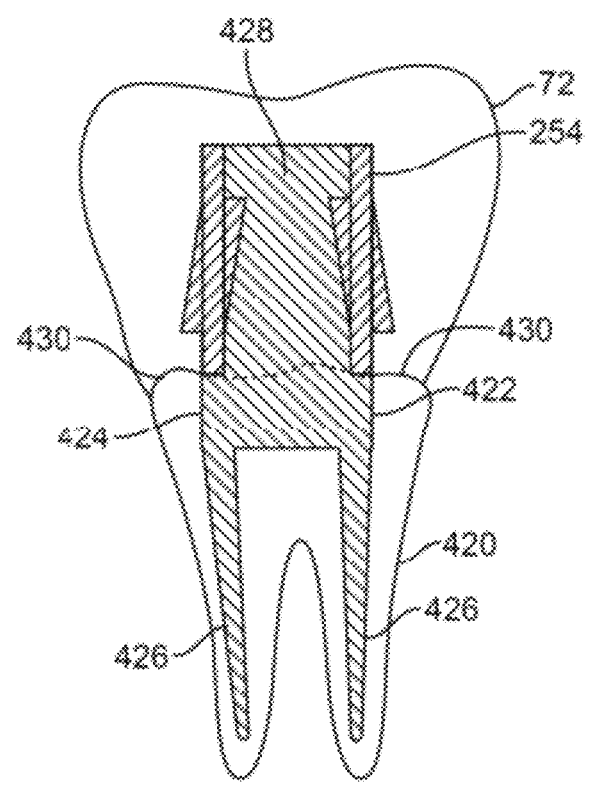
FIG. 40B shows a cross-sectional side view of an abutment assembly secured within the pulp chamber.

In other variations where a pre-existing tooth or root exists, rather than implanting an anchoring implant the existing root may be utilized as an anchor for an abutment assembly. As shown in the partial cross-sectional side view of FIG. 40A, a pre-existing root 420 may be seen where the pulp has been removed (e.g., in a root canal procedure) leaving a pulp chamber 422. The abutment assembly utilized may comprise an abutment 428 which extends from an abutment base 424 which may also have one or more endodontic posts 426 which may be inserted securely into the pulp chamber 422, as shown in FIG. 40B. The pulp chamber 422 may accordingly be cleaned and/or drilled or shaped to remove any infected matter. The one or more posts 426 extending from the abutment base 424 may then be positioned within the pulp chamber 422 and an adhesive (such as a dental cement) may be poured into the pulp chamber 422 to fill any gaps and to ensure a secure fit.

Once the abutment 428 has been desirably secured within the pulp chamber 422, any of the shape memory sleeves 254 described herein (and as practicable) may be secured onto the abutment 428 and the crown 72 may be fitted upon the sleeve 254.

To further ensure a secure fitting of the crown 72, the contacting portion of the remaining root or tooth may be formed into a contacting surface 430 which fits adjacent to the crown 72 in a suitable receiving manner. Although two posts 426 are illustrated in this example, a single post or multiple additional posts may be utilized as desired. Moreover, the abutment assembly may be formed of any number of biocompatible materials, e.g., gold alloys, stainless steel, nickel-titanium alloys, etc. Additionally, the abutment 428 may be formed either as a singular integral member with the base 424 or they may be formed from separate components and coupled to one another.

Figure 41:
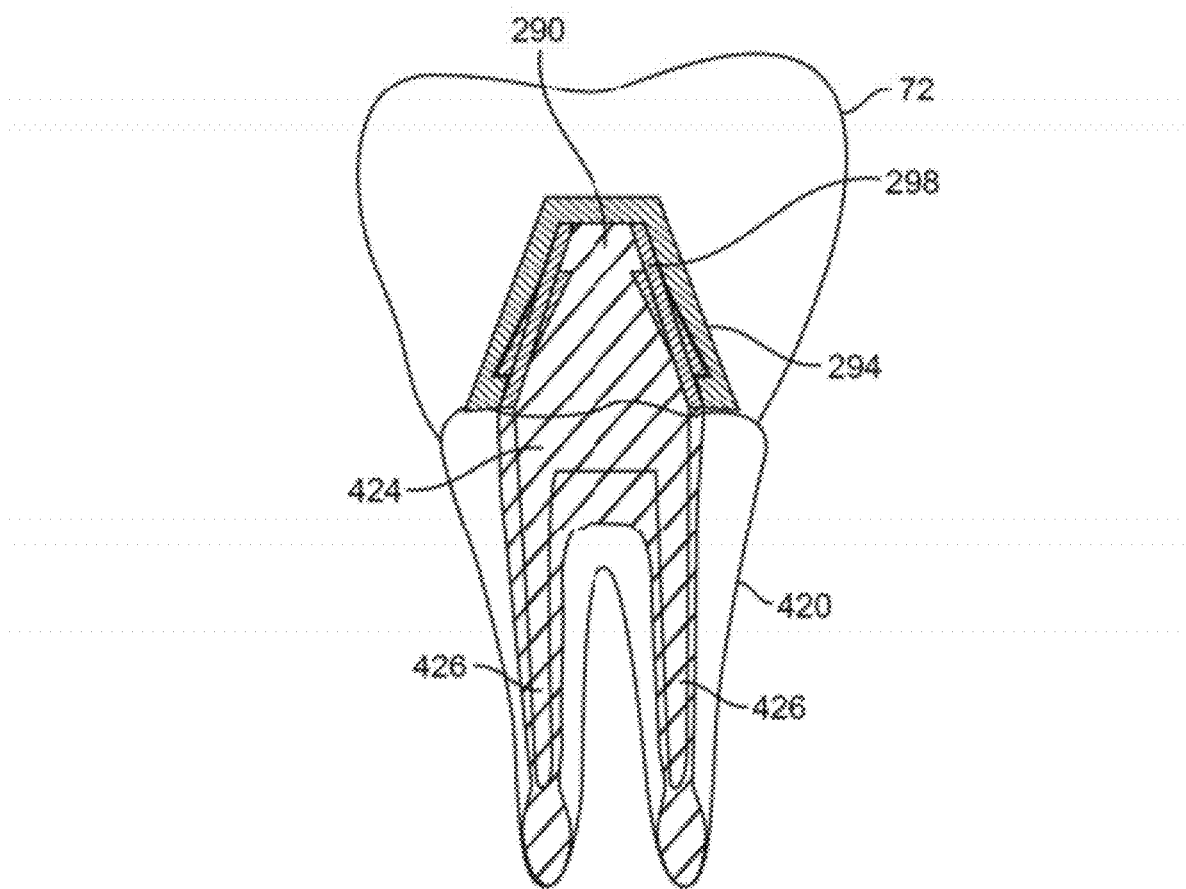
FIG. 41 shows a cross-sectional side view of an abutment assembly secured within the pulp chamber and having a tapered abutment.

FIG. 41 shows a cross-sectional side view of another variation of an abutment assembly which may be secured within a pulp chamber of an existing tooth or teeth. In this example, the abutment assembly may be formed with a tapered abutment 290 extending from the abutment base 424. Accordingly, a tapered shape memory sleeve 298 may be secured upon the tapered abutment 290 with a crown 72 having a correspondingly tapered coping 294 for securement upon the abutment 290, as previously described.

In yet another example, a pre-existing tooth or teeth which may not need to be removed entirely may itself be utilized as an abutment. For instance, as shown in FIG. 42A, a decayed tooth 442 having a root 420 and existing pulp 440 may be prepared by cutting or forming the dentin and enamel into the shape of an abutment 444. In this example, tooth 442 may be cut to form an abutment having undercuts for receiving a self locking sleeve 298. With the abutment shape formed into the tooth 442 itself, a shape memory sleeve 298 may be secured upon the formed tooth abutment 444 and the crown 72 having a corresponding coping 294 may be then secured upon the tooth abutment 444 in a manner as described herein and as shown in FIG. 42B.

In the event that crown 72 requires removal, replacement, or repositioning upon the tooth abutment 444, energy may be applied or removed from shape memory sleeve 298 as previously described. Moreover, although this example is shown with a tapered abutment shape and tapered sleeve, any of the sleeve and abutment designs (as practicable) as described herein may be utilized with this particular variation.

Figure 43A:
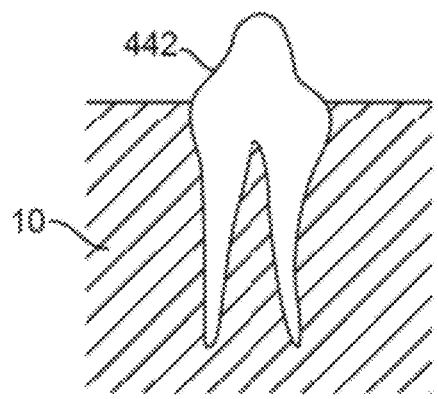
FIGS. 43A to 43C show cross-sectional side views of another variation where a separate abutment may be adhered directly onto a decayed tooth for receiving a sleeve and removable crown.
Figure 43B:
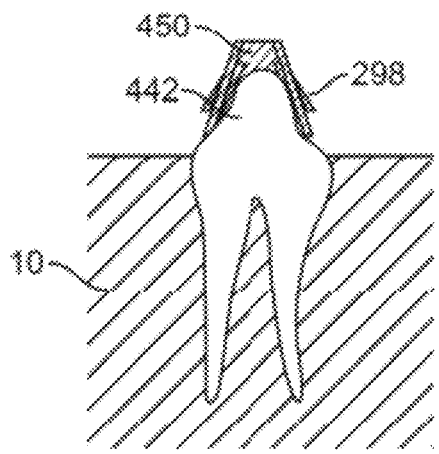
Figure 43C:
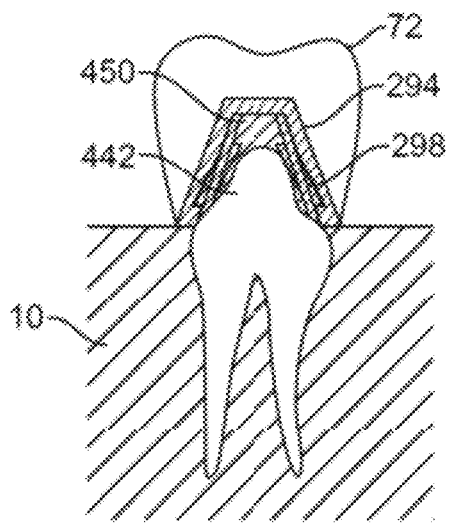

FIGS. 43A to 43C show another variation where a decayed tooth may be prepared for having an abutment secured directly upon the decayed tooth 442. Rather than shaping the remaining decayed tooth 442, a portion of an abutment 450 may be shaped for placement directly upon the exposed tooth 442 by any number of securement mechanisms such as cement. While the cavity of the shaped abutment 450 may be fitted for securement onto the tooth 442, the outer surface of the abutment 450 may be configured to receive a self-locking sleeve 298 as previously described. Accordingly, the abutment 450 may instead be securely adhered directly upon the tooth 442 while the crown 72 may be removably secured onto the sleeve 298 which itself may be removably secured onto the abutment 450.

Figure 44A:
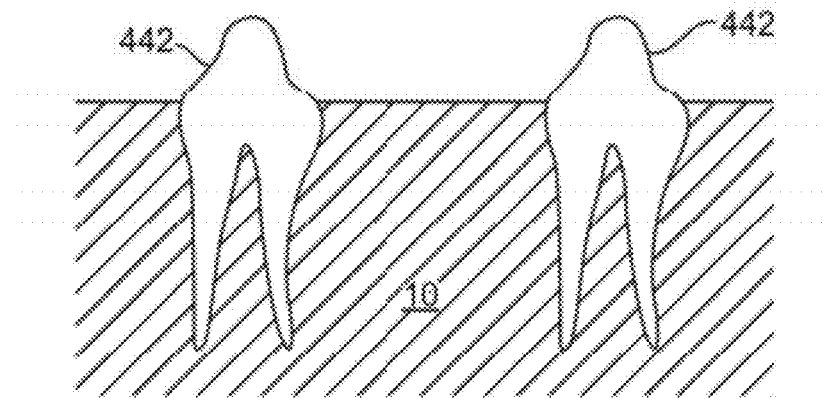
FIGS. 44A to 44C show cross-sectional side views of yet another variation where more than one decayed teeth may be prepared for securement by a corresponding abutment for receiving a removable bridge.
Figure 44B:
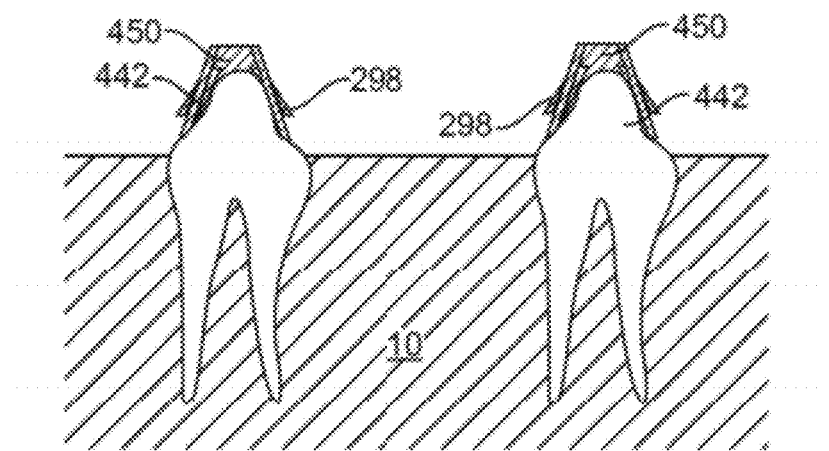
Figure 44C:
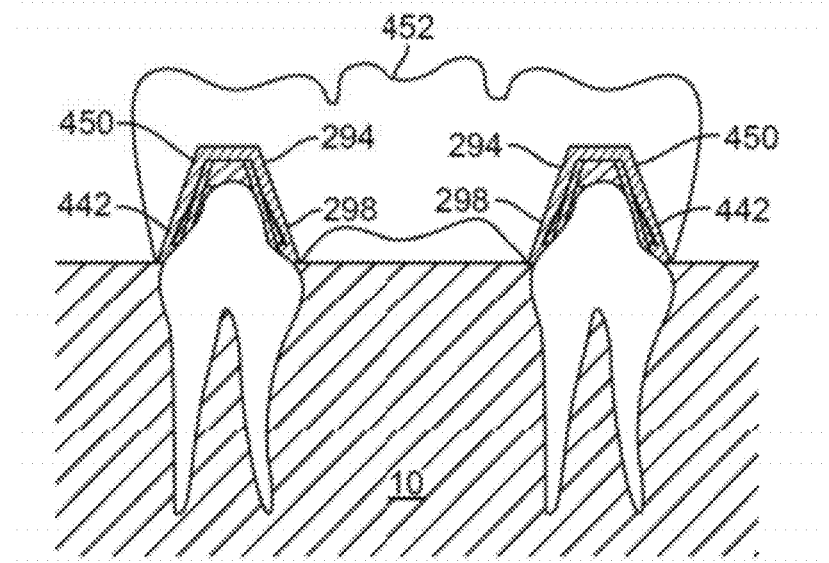

In yet another example, FIGS. 44A to 44C show cross-sectional side views of another variation where multiple decayed teeth 442 may be utilized for securing a respective abutment 450 directly upon each tooth 442. With the abutment 450 secured upon the teeth 442, each abutment 450 may receive a sleeve 298 removably secured onto each abutment 450 such that a prosthesis, e.g., a bridge 452 extending between each of the abutments 450, may be removably secured. To remove or reposition the bridge 452, each of the sleeves 298 may be actuated individually or simultaneously to allow for adjustment of the bridge 452.

The applications of the devices and methods discussed above are not limited to the securement of crowns or bridges but may include any number of further treatment applications where the securement and adjustability of devices within a patient may be utilized. Moreover, such devices and methods may be applied to other treatment sites within the body. Modification of the above-described assemblies and methods for carrying out the invention, combinations between different variations as practicable, and variations of aspects of the invention that are obvious to those of skill in the art are intended to be within the scope of the claims.

What is claimed is:

1. A method of securing an oral appliance, comprising:
   securing an abutment portion onto a pre-existing tooth such that the abutment portion extends from the tooth;
   coupling a sleeve having one or more slap elements which protrude in an alternating manner along the abutment portion such that a portion of the elements extend radially relative to the abutment when the elements are in a locking configuration;
   positioning an oral appliance upon the abutment portion such that the portion of the elements extending radially are secured within a corresponding receiving channel defined along a coping within the oral appliance.

2. The method of claim 1 further comprising actuating the one or more flap elements to retract into a low profile configuration such that the elements are retracted from the receiving channel.

3. The method of claim 2 wherein actuating comprises applying energy to the one or more flap elements.

4. The method of claim 1 further comprising re-actuating the one or more flap elements to reconfigure into the locking configuration.

5. The method of claim 1 wherein securing comprises cementing the abutment portion onto one or more decayed teeth.

6. The method of claim 1 wherein the sleeve comprises one or more flap elements which are comprised of a shape memory.

7. The method of claim 1 further comprising biasing the one or more flap elements to extend radially relative to the abutment via one or more biasing elements positioned along the abutment prior to positioning an oral appliance.

8. The method of claim 1 wherein positioning the oral appliance comprises positioning a crown upon the abutment portion.

\* \* \* \* \*